US011504424B2

(12) United States Patent
Rosa-Calatrava et al.

(10) Patent No.: US 11,504,424 B2
(45) Date of Patent: Nov. 22, 2022

(54) ATTENUATED VIRUS STRAIN AND USE THEREOF AS A VACCINE

(71) Applicants: UNIVERSITE CLAUDE BERNARD LYON 1, Villeurbanne (FR); CENTRE NATIONAL DE LA RECHERCHE SCIENTIFIQUE (CNRS), Paris (FR); ECOLE NORMALE SUPERIEURE DE LYON, Lyons (FR); INSTITUT NATIONAL DE LA SANTE ET DE LA RECHERCHE MEDICALE (INSERM), Paris (FR); UNIVERSITE LAVAL, Quebec (CA)

(72) Inventors: Manuel Rosa-Calatrava, Lyons (FR); Guy Boivin, Quebec (CA); Julia Dubois, Rillieux-la-Pape (FR); Mario Andres Pizzorno, Lyons (FR); Olivier Terrier, Lyons (FR); Marie-Eve Hamelin, Quebec (CA); Marie-Helene Cavanagh, Levis (CA)

(73) Assignees: UNIVERSITE CLAUDE BERNARD LYON 1, Villeurbanne (FR); CENTRE NATIONAL DE LA RECHERCHE SCIENTIFIQUE (CNRS), Paris (FR); ECOLE NORMALE SUPERIEURE DE LYON, Lyons (FR); INSTITUT NATIONAL DE LA SANTE ET DE LA RECHERCHE MEDICALE (INSERM), Paris (FR); UNIVERSITE LAVAL, Quebec (CA)

( * ) Notice: Subject to any disclaimer, the term of this patent is extended or adjusted under 35 U.S.C. 154(b) by 0 days.

(21) Appl. No.: 17/262,263

(22) PCT Filed: Jul. 12, 2019

(86) PCT No.: PCT/FR2019/051759
§ 371 (c)(1),
(2) Date: Jan. 22, 2021

(87) PCT Pub. No.: WO2020/021180
PCT Pub. Date: Jan. 30, 2020

(65) Prior Publication Data
US 2021/0283239 A1    Sep. 16, 2021

(30) Foreign Application Priority Data

Jul. 23, 2018  (FR) ...................................... 1856801
Mar. 21, 2019  (FR) ...................................... 1902934

(51) Int. Cl.
*A61K 39/155* (2006.01)
*A61P 31/14* (2006.01)
*C12N 7/00* (2006.01)
*A61K 39/00* (2006.01)

(52) U.S. Cl.
CPC ............ *A61K 39/155* (2013.01); *A61P 31/14* (2018.01); *C12N 7/00* (2013.01); *A61K 2039/5254* (2013.01)

(58) Field of Classification Search
None
See application file for complete search history.

(56) References Cited

U.S. PATENT DOCUMENTS 8,841,433 B2    9/2014    Fouchier et al.

FOREIGN PATENT DOCUMENTS

WO    2005/014626 A2    2/2005
WO    2007/038862 A2    4/2007

OTHER PUBLICATIONS

Biacchesi, et al., Journal of Virolog vol. 78, Issue 23, Dec. 1, 2004, pp. 12877-12887 (Year: 2004).*
Aerts L, et al., PLoS ONE 10(3): e0120283. https://doi.org/10.1371/journal.pone.0120283 (Year: 2015).*
Barouch—Nature vol. 455 Oct. 2, 2008 doi:10.1038/nature07352 (Year: 2008).*
Weisshaar et al. DNA and CELL Bio vol. 34, pp. 506-510 (Year: 2015).*
Van den Hoogen BG, de Jong JC, Groen J, Kuiken T, de Groot R, Fouchier RA, et al. A newly discovered human pneumovirus isolated from young children with respiratory tract disease. Nat Med. 2001;7(6):719-24.
Peret TC, Boivin G, Li Y, Couillard M, Humphrey C, Osterhaus AD, Erdman DD, Anderson LJ. Characterization of human metapneumoviruses isolated from patients in North America. J Infect Dis. Jun. 1, 2002;185(11):1660-3.
Mazur NI, Higgins D, Nunes MC, Melero JA, Langeduk AC, Horsley N, Buchnolz UJ, Openshaw PJ, MCLellan JS, Englund JA, Mejias A, Karron RA, Simões EA, Knezevic I, Ramilo O, Piedra PA, Chu HY, Falsey AR, Nair H, Kragten-Tabatabaie L, Greenough A, Baraldi E, Papadopoulos NG, Vekemans J, Polack FP, Powell M, Satav A, Walsh EE, Stein RT, Graham BS, Bont LJ; Respiratory Syncytial Virus Network (ReSViNET) Foundation. The respiratory syncytial virus vaccine landscape: lessons from the graveyard and promising candidates. Lancet Infect Dis. Jun. 15, 2018. pii: vol. 18 (10) :e295-e311.

(Continued)

*Primary Examiner* — Janet L Andres
*Assistant Examiner* — Myron G Hill
(74) *Attorney, Agent, or Firm* — Arrigo, Lee, Guttman & Mouta-Bellum LLP

(57) ABSTRACT

The present invention relates to an attenuated virus strain derived from a human metapneumovirus strain comprising the genome sequence represented by sequence SEQ ID NO. 1, said attenuated strain comprising one or more genetic modifications of said sequence SEQ ID NO. 1 attenuating the virulence of said strain.

10 Claims, 19 Drawing Sheets
Specification includes a Sequence Listing.

(56) References Cited

OTHER PUBLICATIONS

Herfst S, de Graaf M, Schrauwen EJ, Sprang L, Hussain K, van den Hoogen BG, Osterhaus AD, Fouchier RA. Generation of temperature-sensitive human metapneumovirus strains that provide protective immunity in hamsters. J Gen Virol. Jul. 2008;89(Pt 7):1553-62.

Wei Y, Zhang Y, Cai H, Mirza AM, Iorio RM, Peeples ME, Niewiesk S, Li J. Roles of the putative integrin-binding motif of the human metapneumovirus fusion (f) protein in cell-cell fusion, viral infectivity, and pathogenesis. J Virol. Apr. 2014;88(8):4338-52.

Yu CM, Li RP, Chen X, Liu P, Zhao XD. Replication and pathogenicity of attenuated human metapneumovirus F mutants in severe combined immunodeficiency mice. Vaccine. Jan. 5, 2012;30(2):231-6.

Liu P, Shu Z, Qin X, Dou Y, Zhao Y, Zhao X. A live attenuated human metapneumovirus vaccine strain provides complete protection against homologous viral infection and cross-protection against heterologous viral infection in BALB/c mice. Clin Vaccine Immunol. Aug. 2013;20(8):1246-54.

Zhang Y, Wei Y, Zhang X, Cai H, Niewiesk S, Li J. Rational design of human metapneumovirus live attenuated vaccine candidates by inhibiting viral mRNA cap methyltransferase. J Virol. Oct. 2014;88(19):11411-29.

Biacchesi S, Skiadopoulos MH, Tran KC, Murphy BR, Collins PL, Buchholz UJ. Recovery of human metapneumovirus from cDNA: optimization of growth in vitro and expression of additional genes. Virology. 2004;321(2):247-59.

Biacchesi S, Skiadopoulos MH, Yang L, Lamirande EW, Tran KC, Murphy BR, Collins PL, Buchholz UJ. Recombinant human Metapneumovirus lacking the small hydrophobic SH and/or attachment G glycoprotein: deletion of G yields a promising vaccine candidate. Journal of Virology. Dec. 2004;78(23):12877-87.

Biacchesi S, Pham QN, Skiadopoulos MH, Murphy BR, Collins PL, Buchholz UJ. Infection of nonhuman primates with recombinant human metapneumovirus lacking the SH, G, or M2-2 protein categorizes each as a nonessential accessory protein and identifies vaccine candidates. Journal of virology. 2005;79(19):12608-13.

Buchholz UJ, Biacchesi S, Pham QN, Tran KC, Yang L, Luongo CL, Skiadopoulos MH, Murphy BR, Collins PL. Deletion of M2 gene open reading frames 1 and 2 of human metapneumovirus: effects on RNA synthesis, attenuation, and immunogenicity. J Virol. Jun. 2005;79(11):6588-97.

Schickli JH, Kaur J, Macphail M, Guzzetta JM, Spaete RR, Tang RS. Deletion of human metapneumovirus M2-2 increases mutation frequency and attenuates growth in hamsters. Virol J. Jun. 3, 2008;5:69.

Pham QN, Biacchesi S, Skiadopoulos MH, Murphy BR, Collins PL, Buchholz UJ. Chimeric recombinant human metapneumoviruses with the nucleoprotein or phosphoprotein open reading frame replaced by that of avian metapneumovirus exhibit improved growth in vitro and attenuation in vivo. J Virol. Dec. 2005;79(24):15114-22.

Tang RS, Schickli JH, MacPhail M, Fernandes F, Bicha L, Spaete J, Fouchier RA, Osterhaus AD, Spaete R, Haller AA. Effects of human metapneumovirus and respiratory syncytial virus antigen insertion in two 3' proximal genome positions of bovine/human parainfluenza virus type 3 on virus replication and immunogenicity. J Virol. Oct. 2003;77(20):10819-28.

Tang RS, Mahmood K, Macphail M, Guzzetta JM, Haller AA, Liu H, Kaur J, Lawlor HA, Stillman EA, Schickli JH, Fouchier RA, Osterhaus AD, Spaete RR. A host-range restricted parainfluenza virus type 3 (PIV3) expressing the human metapneumovirus(hMPV) fusion protein elicits protective immunity in African green monkeys. Vaccine. Feb. 25, 2005;23(14):1657-67.

Russell CJ, Jones BG, Sealy RE, Surman SL, Mason JN, Hayden RT, Tripp RA, Takimoto T, Hurwitz JL. A Sendai Virus recombinant vaccine expressing a gene for truncated human metapneumovirus (hMPV) fusion protein protects cotton rats from hMPV challenge. Virology. Sep. 2017;509:60-66.

Huck B, Scharf G, Neumann-Haefelin D, Puppe W, Weigl J, Falcone V. Novel human metapneumovirus sublineage. Emerg Infect Dis Jan. 2006;12(1):147-50.

Aerts L, Rhéaume C, Carbonneau J, Lavigne S, Couture C, Hamelin MÈBoivin G. Adjuvant effect of the human metapneumovirus (HMPV) matrix protein in HMPV subunit vaccines. J Gen Virol. Apr. 2015;96(Pt 4):767-74.

Dubois J, Cavanagh MH, Terrier O, Hamelin ME, Lina B, Shi R, et al. Mutations in the fusion protein heptad repeat domains of human metapneumovirus impact on the formation of syncytia. The Journal of general virology. 2017;98(6):1174-80.

Aerts L, Cavanagh MH, Dubois J, Carbonneau J, Rheaume C, Lavigne S, et al. Effect of in vitro syncytium formation on the severity of human metapneumovirus disease in a murine model PloS one. 2015;10(3):e0120283.

Hamelin ME, Gagnon C, Prince GA Kiener P, Suzich J, Ulbrandt N, Boivin G. Prophylactic and therapeutic benefits of a monoclonal antibody against the fusion protein of human metapneumovirus in a mouse model. Antiviral Res. Oct. 2010;88(1):31-7.

Palavecino CE, Cespedes PF, Lay MK, Riedel CA, Kalergis AM, Bueno SM. Understanding Lung Immunopathology Caused by the Human Metapneumovirus: Implications for Rational Vaccine Design. Crit Rev Immunol. 2015;35(3):185-202. Review.

Hamelin ME, Couture C, Sackett MK, Boivin G. Enhanced lung disease and Th2 response following human metapneumovirus infection in mice immunized with the inactivated virus. J Gen Virol. Dec. 2007;88(Pt 12):3391-400.PubMed PMID: 18024909.

* cited by examiner

Fig. 1B rCAN98-75

ΔSH-rCAN98-75

ΔG-rCAN98-75 rCAN98-75        ΔSH-CAN98-75        ΔG-CAN98-75

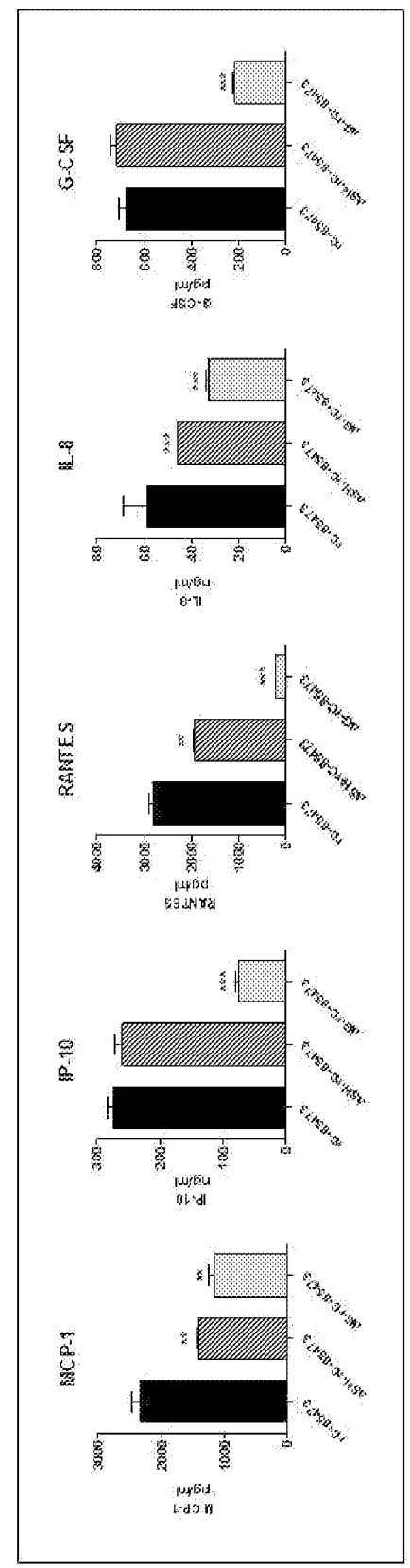

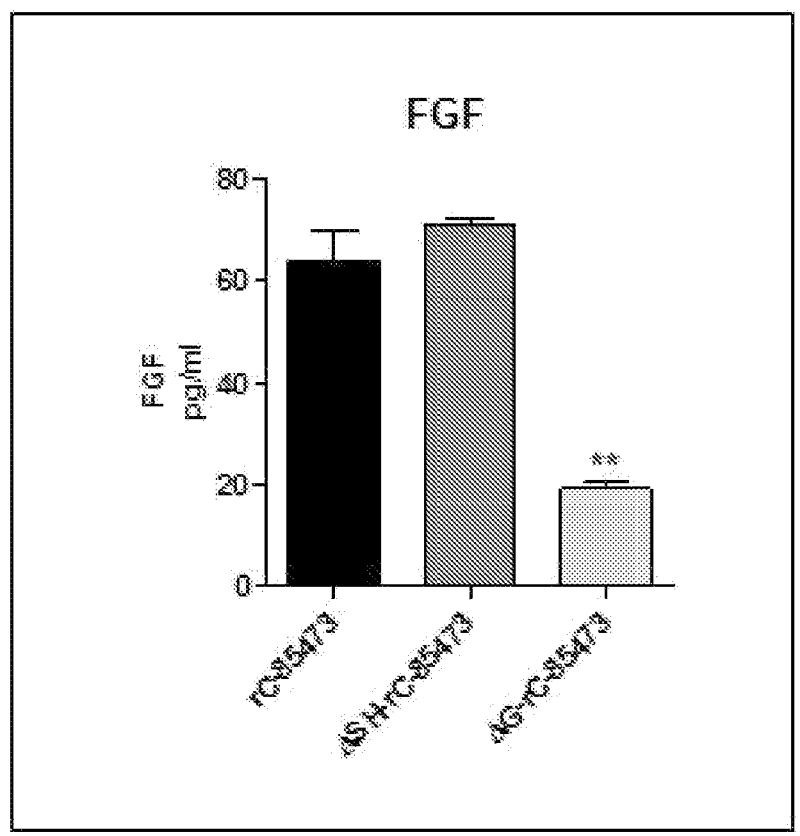

Fig. 8A

Viral loads (FFU/ml) vs Days post-infection

TNF-α pg/ml vs Days post-infection

- mock
- rC-85473
- ΔSH-rC-85473
- ΔG-rC-85473

SEQUENCE LISTING

<160> NUMBER OF SEQ ID NOS: 8

<210> SEQ ID NO 1
<211> LENGTH: 13394
<212> TYPE: DNA
<213> ORGANISM: human metapneumovirus

<400> SEQUENCE: 1

```
gcgaaaaaaa cgcgtataaa ttagattaca aaaaaatatg ggacaagtga aaatgtctct      60
tcaagggatt cacctgagtg atctatcata caagcatgct atattaaaag agtctcagta     120
cacaataaaa agagatgtgg gtacaacaac tgcagtgaca ccctcatcat tgcaacaaga     180
```

```
aataacgctg ttgtgtggag aaattctgta tgctaaacat gctgattaca aatatgctgc    240
agaaatagga atacaatata ttagcacagc tttaggatca gagagagtgc agcagattct    300
gaggaactca ggcagtgaag tccaagtggt cttaaccaga acgtactctc tggggaaagt    360
taaaaacaat aaaggagaag atttacagat gttagacata cacggggtag agaagagctg    420
ggtagaagag atagacaaag aagcaaggaa acaatggca accttgctta aggaatcatc     480
aggtaatatc ccacaaaatc agaggccctc agcaccagac acacccataa tcttattatg    540
tgtaggtgca ttaatattta ctaagctagc atcaaccata gaagtgggac tagagaccac    600
agtcagaagg gctaaccgtg tactaagtga tgcactcaag agataccta gaatggacat     660 cccaaaaatt gccagatcct tctatgactt atttgaacaa aaagtgtatc acagaagttt    720
gttcattgag tatggcaaag cattaggctc atcatctaca ggcagcaaag cagaaagtct    780
atttgttaat atattcatgc aagcttatgg agccggtcaa acaatgctaa ggtgggggt     840 cattgccagg tcatccaaca atataatgtt aggacatgta tctgtccaag ctgagttaaa    900
acaggtcaca gaagtctatg acttggtgcg agaaatgggc cctgaatctg acttctaca     960 tttaaggcaa agcccaaaag ctggactgtt atcactagcc aactgtccca actttgcaag    1020
tgttgttctc ggaaatgcct caggcttagg cataatcggt atgtatcgtg ggagagtacc    1080
aaacacagaa ttattttcag cagcagaaag ttatgccaaa agtttgaaag agagcaataa    1140
aatcaatttc tcttcattag gacttacaga tgaagagaaa gaggctgcag aacatttctt    1200
aaatgtgagt gacgacagtc aaaatgatta tgagtaatta aaaagtggg acaagtcaaa     1260 atgtctttcc ctgaaggaaa agatattctt ttcatgggta atgaagcagc aaaattagca    1320
gaagctttcc agaaatcatt aaggaaacca agtcataaaa gatctcaatc tattataga    1380 gaaaaagtga acactgtatc agaaacattg gaattaccta ctatcagtag acctgcaaaa    1440
ccaaccatac tgtcagaacc aaagttagca tggactgata aggtggggc aatcaaaact     1500 gaaataaagc aagcaatcaa agtcatggat cctattgagg aagaagagtc tactgagaag    1560
aaggtgctgc cctccagtga tgggaaaacc cctgcagaaa agaaactgaa accatcaact    1620
aacaccaaaa agaaagtttc gtttacacca aatgaaccag gaaaatatac aaagttggaa    1680
aaagatgctc tagatttgct ctcagataat gaagaagaag atgcagaatc ttcaatctta    1740 accttgaag aaagagatac ttcatcgtta agcattgagg ccagattgga atcaatagag    1800
gagaaattaa gcatgatatt agggctatta agaacactca acattgctac agcaggaccc    1860
acagcagcaa gagatgggat cagagatgca atgattggcg taagagagga attaatagca    1920
gacataataa aggaagccaa agggaaagca gcagaaatga tggaagagga aatgagtcaa    1980
cgatcaaaaa taggaaacgg tagtgtaaaa ctaacagaga agcaaaaga gcttaacaaa    2040 attgttgaag atgaaagcac aagtggagaa tctgaagaag aagaagaacc aaaagacata    2100
caagacaata gtcaagaaga tgacatttac cagttaatta tgtagtttaa taaaaataaa    2160
caatgggaca agtaaaaatg gagtcctacc tagtagacac ttatcaaggc attccttaca    2220
cagcagctgt tcaagttgat ctaatagaaa aggacctgtt acctgcaagc ctaacaatat    2280
ggttcccttt gtttcaggcc aacacaccac cagcagtgct gctcgatcag ttgaaaaccc    2340
taacaataac cactctgtat gctgcatcac aaaatggtcc aatactcaaa gtgaatgcat    2400
cagcccaagg tgcagcaatg tctgtacttc ccaaaaaatt tgaagtcaat gcgactgtag    2460
cactcgatga atatagcaaa ttggaatttg acaaactcac agtctgtgaa gtaaaaacag    2520
```

-continued

```
tttacttaac aaccatgaaa ccatacggga tggtatcaaa atttgtgagc tcagccaaat    2580
cagttggcaa aaaaacacat gatctaatcg cactgtgtga ttttatggat ctagaaaaga    2640
acacacctgt tacaatacca gcattcatca aatcagtttc aatcaaagag agtgagtcag    2700
ctactgttga agctgctata agcagtgaag cagaccaagc tctaacacag gccaaaattg    2760
caccttatgc gggattgatt atgatcatga ctatgaacaa tcccaaaggc atattcaaaa    2820
agcttggagc tgggactcaa gttatagtag aactaggagc atatgtccag gctgaaagca    2880
taagtaaaat atgcaagact tggagccatc aagggacaag atatgtgttg aagtccagat    2940
aacagccaag caccttggcc aagagctact aactctatct catagattat aaagtcacca    3000
ttctagttat ataaaaatca gttagaaca agaattaaat caatcaagaa tgggacaaat     3060
aaaaatgtct tggaaagtgg tgatcatttt ttcattgtta ataacacctc aacacggtct    3120
taaagagagc tatttagaag agtcatgtag cactataact gaaggatatc tcagtgttct    3180
gaggacaggt tggtatacca acgtttttac actggaggta ggtgatgtag agaaccttac    3240
atgtgctgat ggacctagct taataaaaac agaattagac ctgaccaaaa gtgcactaag    3300
agaactcaga acagtttctg ctgatcaact ggcaagagag gagcaaattg agaatcccag    3360
acaatctaga tttgttctag gagcaatagc actcggtgtt gcaacagcag ctgcagttac    3420
agcaggtgtt gcaattgcca aaccatccg gcttgaaagt gaagtaacag caattaagaa     3480
tgccctcaaa aagaccaatg aagcagtatc tacattgggg aatggagttc gagtgttggc    3540
aactgcagtg agggagctgg aagattttgt gagcaagaat ctaacacgtg caatcaacaa    3600
aaacaagtgc gacattgctg acctgaaaat ggccgttagc ttcagtcaat tcaacagaag    3660
gtttctaaat gttgtgcggc aattttcaga caatgctgga ataacaccag caatatcctt    3720
ggacttaatg acagatgctg aactagccag agctgtttcc aacatgccaa catctgcagg    3780
acaaataaaa ctgatgttgg agaaccgtgc aatggtaaga agaaagggt tcggaatcct    3840 gataggagtt tacggaagct ccgtaattta catggtgcaa ctgccaatct ttggagttat    3900
agacacgcct tgctggatag taaaagcggc cccttcttgc tcagaaaaaa agggaaacta    3960
tgcttgcctt ttaagagaag atcaaggatg gtattgtcag aatgcagggt caactgttta    4020
ctacccaaat gaaaaagact gcgaaacaag aggagaccat gtcttttgcg acacagcagc    4080
aggaatcaat gttgctgagc agtcaaagga gtgcaacatc aacatatcca ctactaatta    4140
cccatgcaaa gttagcacag aagacaccc tatcagtatg gttgcactgt ctcctcttgg    4200
ggctttggtt gcttgctaca agggagtgag ctgttccatt ggcagcaaca gagtagggat    4260
catcaagcaa ctgaacaaag gctgctctta tataaccaac caagacgcag acacagtgac    4320
aatagcaaac actgtatacc agctaagcaa agttgagggc gaacagcatg ttataaaagg    4380
aaggccagtg tcaagcagct ttgatccagt caaatttcct gaagatcaat tcaatgttgc    4440
acttgaccaa gttttcgaaa gcattgagaa cagtcaggcc ttggtggatc aatcaaacag    4500
aatcctaagc agtgcagaga aggaaacac tggcttcatc attgtaataa ttctaattgc    4560
tgtccttggc tctaccatga tcctagtgag tgttttatc ataataaaga aaacaaagaa     4620
acccacagga gcacctccag agctgagtgg tgtcacaaac aatggcttca taccacataa    4680
ttagttaatt aaaaataaag taaattaaat taaataaaa taaaattaaa attaaaataa      4740
aataaaaata aaaatttggg acaaatcata atgtctcgca aggctccatg caaatatgaa    4800
gtgcggggca aatgcaatag aggaagtgag tgcaagttta ccacaatta ctggagttgg     4860 ccagatagat acttactaat aagatcaaat tatttattaa atcaacttttt aaggaacact    4920
```

```
gatagagctg atggcttatc aataatatca ggagcaggca gagaagatag gacacaagat   4980
tttgtcctag gttccaccaa tgtggttcaa ggttatattg atgataacca aagcataaca   5040
aaagctgcag cctgttacag tctacataat ataatcaaac aactacaaga agttgaagtt   5100
aggcaggcta gagataacaa accatctgac agcaaacatg tggcacttca caacttagtc   5160
ctatcttata tggagatgag caaaattcct gcatctttaa tcaacaatct caaaagactg   5220
ccgagagaga aactgaaaaa attagcaaag cttataattg acttatcagc aggtgctgaa   5280
aatgactctt catatgcctt gcaagacagt gaaagcacta atcaagtgca gtgagcatgg   5340
tcctgttttc attactatag aggttgatta catgatatgg actcataagg acttaaaaga   5400
agctttatct aatgggatag tgaagtctca tactaacatt tacaattgtt atttagaaaa   5460
catagaaatt atatatgtca aggcttactt aagttagtaa aaacacatca gagtgggata   5520
aatgacaatg ataacattag atgtcattaa aagtgatggg tcttcaaaaa catgtactca   5580
cctcaaaaaa ttaattaaag accactctgg taaagtgctt attgtactta agttaatatt   5640
agctttacta acatttctca cagtgacaat caccatcaat tatataaaag tagaaaacaa   5700
tctgcaaata tgtcagtcaa aaactgaatc agacaaaaag gactcatcat caaataccac   5760
atcagtcaca accaagacta ctctaaatca tgatataaca cagtatttta aaagtttgat   5820
tcaaaggtat acaaactctg caataaacag agacacatgc tggaaaataa gcagaaatca   5880
atgcacaaac ataacaacat acaaattttt atgttttaaa tctgaagaaa caaaaaccaa   5940
caattgtgat aaactgacag atttatgcag aaacaaacca aaaccagctg ttgaagtgta   6000
tcacatagta gaatgccatt gtatatacac agttaaatgg aagtgctatc attacccaat   6060
agatgaaacc caatcctaaa taacactaga ttaggatcca tccaagtctg ttagttcaac   6120
aatttagtta ttttaaaaata ttttgaaaac aagtaagttt ctatgatact tcataataat   6180
aagtaataat taattgctta atcatcatca caacattatt cgaaaccata actattcaat   6240
ttaagaagta aaaacaataa tatgggacaa gtagttatgg aggtgaaagt ggagaacatt   6300
cgaacaatag atatgctcaa agcaagagtg aaaaatcgtg tggcacgcag caaatgcttt   6360
aaaaatgcct ctttgatcct aataggaata actacattga gtatagccct caatatctat   6420
ctaatcataa actatacaat gcaagaaaac acatccgaat cagaacatca caccagctca   6480
tcacccatgg aatccagcag ggaaactcca acagtcccta tggacaactc agacaccaat   6540
ccaggctcac agtatccaac tcaacagtcc acagaaggct ccacactcta ctttgcagcc   6600
tcagcaagct caccagagac agaaccaaca tcaacaccag acacaacaag ccgcccgccc   6660
ttcgtcgaca cacacacaac actaccaagt gcaagcagaa caaggacaag tccggcagtc   6720
cacacaaaaa acaatccaag gacaagcccc agaacacatt ccccaccatg ggcaatgaca   6780
aggacggtcc gtggaaccac cactctccgc acaagcagca caagaaaaag accgtccaca   6840
gcatcagtcc aacctgacag cagcgcaaca acccacaaac acgaagaagc aagcccagtg   6900
agcccgcaaa catctgcgag cacagcaaga ccacaaagga agggcatgga ggccagcaca   6960
tcaacaacat acaaccaaac tagttaacaa aaaatacaaa ataactctaa gataaaccat   7020
atagacacca acaattgaga agccaaaagg caattcacaa tctctccaaa aaggcaacaa   7080
caccatatta gctccgctta aatctccctg gaaaaaacac tcgcccatat accaactata   7140
ccacaaccat cccaagaaaa aaagctgggt aaaacaacac ccaagagaca aataacaatg   7200
gatcctctta atgaatccac tgttaatgtc tatcttcccg actcatatct taaaggagtg   7260
```

```
atttcttttta gtgagactaa tgcaattggt tcatgtctct taaaaagacc ttacctaaaa    7320
aatgacaaca ctgcaaaagt tgccatagag aatcctgtta tcgagcatgt tagactcaaa    7380
aatgcaatca attctaagat gaaaatatca gattacagga tagtagagcc agtaaacatg    7440
caacatgaaa ttatgaagaa tgtacacagt tgtgagctca cattattaaa acagttttta    7500
acaaggagta aaatattag cactcttaaa ttaaatatga tatgtgattg gctgcagtta    7560
aagtctacat cagatgatac ctcaatctta agttttatag atgtagaatt tatacctagc    7620
tgggtaagca attggtttag taattggtac aatctcaaca agttgattct ggaattcagg    7680
aaagaagaag taataagaac tggttcaatc ttgtgtaggt cattgggtaa attagttttt    7740
gttgtatcat catacggatg tatagtcaag agcaacaaaa gcaaaagagt gagcttcttc    7800
acatacaatc aactgttaac atggaaagat gtgatgttaa gtagattcaa tgcaaatttc    7860
tgtatatggg taagcaacag tctgaatgaa aatcaagaag ggttagggtt gagaagtaat    7920
ctgcaaggca tattaactaa taagctatat gaaactgtag attatatgct tagtttgtgt    7980
tgcaatgaag gtttctcact tgtgaaagag tttgagggtt ttattatgag tgaaatcctt    8040
aggattactg aacatgctca attcagtact agatttagaa atactttatt aaatggatta    8100
actgatcaat tgcaaaaatt aaaaaataaa aacagactca gagttcatgg taccgtgtta    8160
gaaaataatg attatccaat gtatgaagtt gtacttaaat tattaggaga tactttgaga    8220
tgtattaaat tattaatcaa taaaaactta gagaatgctg ctgaattata ctatatattt    8280
agaatattcg gtcacccaat ggtagatgaa agagatgcaa tggatgctgt caaattaaac    8340
aatgaaatca caaaaatcct caggttggag agcttgacag aactaagagg ggcattcata    8400
ttaaggatta tcaaaggatt tgtagacaac aacaaaagat ggccgaaaat taaaaactta    8460
aaagtgctta gtaaaagatg gactatgtac ttcaaagcaa aaagttaccc tagtcaactt    8520
gaattaagtg aacaagattt tttagagctt gctgcaatac agtttgaaca agagttttct    8580
gttcctgaaa aaaccaacct tgagatggta ttaaatgata aagctatatc acctcctaaa    8640
agattaattt ggtctgtgta cccaaaaaat tacttacctg agacaataaa aaatcgatat    8700
ctagaagaga ctttcaatgc aagtgatagt ctcaaaacaa gaagagtact agagtactat    8760
ttgaaagata ataaattcga ccaaaaagaa cttaaaagtt atgtggttaa acaagaatat    8820
ttaaatgata aggatcatat tgtctcgcta actggaaaag aaagagaatt aagtgtaggt    8880
agaatgtttg ctatgcaacc aggaaaacag cgacaaatac aaatattggc tgaaaaattg    8940
ttagctgata atattgtacc cttttttccca gaaactttaa caagtatgg tgatctagat    9000 cttcagagaa taatggaaat caaatcagaa ctttcttcta ttaaaaccag aagaaatgat    9060
agttataata attacattgc aagagcatcc atagtaacag atttaagtaa gttcaaccaa    9120
gcctttaggt atgaaactac agcgatctgt gcggatgtag cagatgaact acatggaaca    9180
caaagcctat tctgttggtt acatcttatc gttcctatga ctacaatgat atgtgcctat    9240
agacatgcac caccagaaac aaaaggtgaa tatgatatag ataagataga agagcaaagt    9300
ggtttatata gatatcatat gggtggtatt gaaggatggt gtcaaaaact ctggacaatg    9360
gaagctatat cttttattaga tgttgtatct gtaaagacac gatgtcaaat gacatcttta    9420
ttaaacggtg acaaccaatc aatagatgta agtaaaccag ttaagttatc tgagggttta    9480
gatgaagtga aagcagatta tagcttggct gtaaaaatgc taaaagaaat aagagatgca    9540
tacagaaata taggccataa acttaaagaa ggggaaacat atatatcaag agatcttcag    9600
tttataagta aggtgattca atctgaagga gtaatgcatc ctacccctat aaaaaagatc    9660
```

```
ttaagagtgg gaccatggat aaacacaata ttagatgaca ttaaaaccag tgcagagtca    9720 ataggagtc tatgtcagga attagaattt aggggggaaa gcataatagt tagtctgata    9780
ttaaggaatt tttggctgta taatttatac atgcatgaat caaagcaaca ccccctagca    9840
gggaagcagt tattcaaaca actaaataaa acattaacat cagtgcagag atttttttgaa    9900 attaaaaagg aaaatgaagt agtagatcta tggatgaaca taccaatgca gtttggagga    9960
ggagatccag tagtcttcta tagatctttc tatagaagga cccctgattt tttaactgaa   10020
gcaatcagtc atgtagatat tctgttaaaa atatcagcca acataagaaa tgaagcgaaa   10080
ataagtttct tcaaagcctt actgtcaata gaaaaaaatg aacgtgctac actgacaaca   10140
ctaatgagag accctcaagc tgtgggctca gagcgacaag caaaagtaac aagtgatatc   10200
aatagaacag cagttaccag catcttaagt ctttctccaa atcaactttt cagcgatagt   10260
gctatacact acagtagaaa tgaagaagag gtcggaatca ttgctgacaa cataacacct   10320
gtttatcctc atggactgag agtttttgtat gaatcattac cttttcataa agctgaaaaa   10380
gttgtaaata tgatatcagg aacaaaatcc ataaccaact tattacagag aacatctgct   10440
attaatggtg aagatattga cagagctgta tccatgatgc tggagaacct aggattatta   10500
tctagaatat tgtcagtagt tgttgatagt atagaaattc caaccaaatc taatggtagg   10560
ctgatatgtt gtcagatatc tagaacccta agggagacat catggaataa tatggaaata   10620
gttggagtaa catcccctag catcactaca tgcatggatg tcatatatgc aactagctct   10680
catttgaaag ggataatcat tgaaaagttc agcactgaca gaactacaag aggtcaaaga   10740
ggtccaaaga gcccttgggt aggatcgagc acgcaagaga aaaaattagt tcctgtttat   10800
aacagacaaa ttcttttcaaa acaacaaaga gaacagctag aagcaattgg aaaaatgaga   10860
tgggtatata aagggacacc aggtttaaga cgattactca ataagatttg tcttggaagt   10920
ttaggcatta gttacaaatg tgtaaaacct ttattaccta ggtttatgag tgtaaatttc   10980
ctacacaggt tatctgtcag tagtagacct atggaattcc cagcatcagt tccagcttat   11040
agaacaacaa attaccattt tgacactagt cctattaatc aagcactaag tgaaagattt   11100
gggaatgaag atattaattt ggtcttccaa aatgcaatca gctgtggaat tagcataatg   11160
agtgtagtag aacaattaac tggtaggagt ccaaaacagt tagttttaat accccaatta   11220
gaagaaatag acattatgcc accaccagtg tttcaaggga aattcaatta taagctagta   11280
gataagataa cttctgacca acatatcttc agtccagaca aaatagatat gttaacactg   11340
gggaaaatgc tcatgccaac tataaaaggt cagaaaacag atcagttctt gaacaagaga   11400
gagaattatt tccatgggaa caatcttatt gagtctttgt cagcagcgtt agcatgtcat   11460
tggtgtggga tattaacaga gcaatgtata gaaaataata ttttcaagaa agactgggt   11520 gacgggttca tatcggatca tgcttttatg gacttcaaaa tattcctatg tgtctttaaa   11580
actaaacttt tatgtagttg gggatcccaa gggaaaaaca ttaaagatga agatatagta   11640
gatgaatcga tagataaact gttaaggatt gataatactt tttggagaat gttcagcaag   11700
gttatgtttg aatcaaaggt taagaaaagg ataatgttat atgatgtaaa atttctatca   11760
ttagtaggtt atataggtt taagaattgg tttatagaac agttgagatc agctgagttg   11820
catgaggtac cttggattgt caatgccgaa ggtgatctgg ttgagatcaa gtcaattaaa   11880
atctatttgc aactgatagaa gcagagttta tttttaagaa taactgtttt gaactataca   11940
gatatggcac atgctctcac aagattaatc agaaagaagt tgatgtgtga taatgcacta   12000
```

```
ttaacttcaa ttccatcccc aatggttaac ttaactcaag ttattgatcc tacagaacaa    12060
ttagcttatt tccctaagat aacatttgaa aggctaaaaa attatgacac tagttcaaat    12120
tatgctaaag gaaagctaac aaggaattac atgatactgt tgccatggca acatgttaat    12180
agatataact ttgtctttag ttctactgga tgtaaagtta gtctaaaaac atgcattgga    12240
aaacttatga aagatctaaa ccctaaagtt ctgtacttta ttggagaagg ggcaggaaat    12300
tggatggcca aacagcatg tgaatatcct gacatcaaat ttgtatacag aagttttaaaa    12360 gatgaccttg atcatcatta cctttggaa taccagagag tgataggaga attaagcagg    12420
ataatagata gtggtgaagg ctttcaatg gaaacaacag atgcaactca aaaaactcat    12480
tgggatttga tacacagagt aagcaaagat gctttattaa taactttatg tgatgcagaa    12540
tttaaggaca gagatgattt ttttaagatg gtaattctat ggaggaaaca tgtattatca    12600
tgcagaattt gcactaccta tgggacagac ctctatttat tcgcaaagta tcatgctaaa    12660
gactgcaata taaaattacc tttttttgtg agatcagttg ccacctttat tatgcaaggt    12720
agtaaactgt caggctcgga atgctacata ctcttaacac taggccacca caacaattta    12780
ccttgtcatg gagaaataca aaattctaag atgaaaatag cagcgtgtaa tgattttat    12840 gctgcaaaaa aacttgacaa taaatcaatt gaagccaact gtaaatcact tttatcaggg    12900
ctaagaatac cgataaataa gaaggaatta aatagacaga aaggttatt aacactacaa    12960 agcaaccatt cttctgtagc aacagttgga ggtagcaagg tcatagagtc taatggtta    13020 acaaacaagg caaacacaat aattgattgg ttagaacata ttttaaattc tccaaaaggt    13080
gaattaaatt atgatttttt tgaagcatta gaaaatactt accctaatat gattaaacta    13140
atagataatc tagggaatgc agagattaaa aaactgatca agtaactgg atatatgctt    13200 gtaagtaaaa aatgaaaaat gataaaaatg ataaaatagg tgacaacttc atactattcc    13260
aaagtaatca tttgattatg caattatgta atagttaatt aaaaactaaa aatcaaaagt    13320
taaaaactaa taactgtcat taagtttatt aaaaataaga aattataatt ggatgtatac    13380 ggttttttg ccgt                                                      13394
```

<210> SEQ ID NO 2
<211> LENGTH: 12645
<212> TYPE: DNA
<213> ORGANISM: human metapneumovirus

<400> SEQUENCE: 2

```
gcgaaaaaaa cgcgtataaa ttagattaca aaaaaatatg ggacaagtga aaatgtctct      60
tcaagggatt caccgagtg atctatcata caagcatgct atattaaaag agtctcagta     120
cacaataaaa agagatgtgg gtacaacaac tgcagtgaca ccctcatcat tgcaacaaga     180
aataacgctg ttgtgtggag aaattctgta tgctaaacat gctgattaca aatatgctgc     240
agaaatagga atacaatata ttagcacagc tttaggatca gagagagtgc agcagattct     300
gaggaactca ggcagtgaag tccaagtggt cttaaccaga acgtactctc tggggaaagt     360
taaaaacaat aaaggagaag atttacagat gttagacata cacggggtag agaagagctg     420
ggtagaagag atagacaaag aagcaaggaa acaatggca accttgctta aggaatcatc     480
aggtaatatc ccacaaaatc agaggccctc agcaccagac acacccataa tcttattatg     540
tgtaggtgca ttaatattta ctaagctagc atcaaccata gaagtgggac tagagaccac     600
agtcagaagg gctaacgtg tactaagtga tgcactcaag agatacccta gaatggacat     660
ccccaaaatt gccagatcct tctatgactt atttgaacaa aagtgtatc acagaagttt     720
```

```
gttcattgag tatggcaaag cattaggctc atcatctaca ggcagcaaag cagaaagtct      780
atttgttaat atattcatgc aagcttatgg agccggtcaa acaatgctaa ggtgggggt      840 cattgccagg tcatccaaca atataatgtt aggacatgta tctgtccaag ctgagttaaa      900
acaggtcaca gaagtctatg acttggtgcg agaaatgggc cctgaatctg acttctaca      960 tttaaggcaa agcccaaaag ctggactgtt atcactagcc aactgtccca actttgcaag     1020
tgttgttctc ggaaatgcct caggcttagg cataatcggt atgtatcgtg ggagagtacc     1080
aaacacagaa ttattttcag cagcagaaag ttatgccaaa agtttgaaag agagcaataa     1140
aatcaatttc tcttcattag gacttacaga tgaagagaaa gaggctgcag aacatttctt     1200
aaatgtgagt gacgacagtc aaaatgatta tgagtaatta aaaaagtggg acaagtcaaa     1260 atgtcttttcc ctgaaggaaa agatattctt ttcatgggta atgaagcagc aaaattagca     1320
gaagctttcc agaaatcatt aaggaaacca agtcataaaa gatctcaatc tattatagga     1380 gaaaagtga acactgtatc agaaacattg gaattaccta ctatcagtag acctgcaaaa     1440
ccaaccatac tgtcagaacc aaagttagca tggactgata aggtggggc aatcaaaact     1500 gaaataaagc aagcaatcaa agtcatggat cctattgagg aagaagagtc tactgagaag     1560
aaggtgctgc cctccagtga tgggaaaacc cctgcagaaa agaaactgaa accatcaact     1620
aacaccaaaa agaaagtttc gtttacacca aatgaaccag gaaaatatac aaagttggaa     1680
aaagatgctc tagatttgct ctcagataat gaagaagaag atgcagaatc ttcaatctta     1740 accttgaag aaagagatac ttcatcgtta agcattgagg ccagattgga atcaatagag     1800
gagaaattaa gcatgatatt agggctatta agaacactca acattgctac agcaggaccc     1860
acagcagcaa gagatgggat cagagatgca atgattggcg taagagagga attaatagca     1920
gacataataa aggaagccaa agggaaagca gcagaaatga tggaagagga aatgagtcaa     1980
cgatcaaaaa taggaaacgg tagtgtaaaa ctaacagaga aagcaaaaga gcttaacaaa     2040
attgttgaag atgaaagcac aagtggagaa tctgaagaag aagaagaacc aaaagacata     2100
caagacaata gtcaagaaga tgacatttac cagttaatta tgtagtttaa taaaaataaa     2160
caatgggaca agtaaaaatg gagtcctacc tagtagacac ttatcaaggc attccttaca     2220
cagcagctgt tcaagttgat ctaatagaaa aggacctgtt acctgcaagc ctaacaatat     2280
ggttcccttt gtttcaggcc aacacaccac cagcagtgct gctcgatcag ttgaaaaccc     2340
taacaataac cactctgtat gctgcatcac aaaatggtcc aatactcaaa gtgaatgcat     2400
cagcccaagg tgcagcaatg tctgtacttc ccaaaaaatt tgaagtcaat gcgactgtag     2460
cactcgatga atatagcaaa ttggaatttg acaaactcac agtctgtgaa gtaaaaacag     2520
tttacttaac aaccatgaaa ccatacggga tggtatcaaa atttgtgagc tcagccaaat     2580
cagttggcaa aaaaacacat gatctaatcg cactgtgtga ttttatggat ctagaaaaga     2640
acacacctgt tacaatacca gcattcatca atcagtttc aatcaaagag agtgagtcag     2700
ctactgttga agctgctata agcagtgaag cagaccaagc tctaacacag gccaaaattg     2760
caccttatgc gggattgatt atgatcatga ctatgaacaa tcccaaaggc atattcaaaa     2820
agcttggagc tgggactcaa gttatagtag aactaggagc atatgtccag gctgaaagca     2880
taagtaaaat atgcaagact tggagccatc aagggacaag atatgtgttg aagtccagat     2940
aacagccaag caccttggcc aagagctact aactctatct catagattat aaagtccacca    3000 ttctagttat ataaaaatca agttagaaca agaattaaat caatcaagaa tgggacaaat    3060
```

-continued

```
aaaaatgtct tggaaagtgg tgatcatttt ttcattgtta ataacacctc aacacggtct    3120
taaagagagc tatttagaag agtcatgtag cactataact gaaggatatc tcagtgttct    3180
gaggacaggt tggtatacca acgttttac actggaggta ggtgatgtag agaaccttac     3240
atgtgctgat ggacctagct taataaaaac agaattagac ctgaccaaaa gtgcactaag    3300
agaactcaga acagtttctg ctgatcaact ggcaagagag gagcaaattg agaatcccag    3360
acaatctaga tttgttctag gagcaatagc actcggtgtt gcaacagcag ctgcagttac    3420
agcaggtgtt gcaattgcca aaccatccg gcttgaaagt gaagtaacag caattaagaa     3480
tgccctcaaa aagaccaatg aagcagtatc tacattgggg aatggagttc gagtgttggc    3540
aactgcagtg agggagctgg aagatttgt gagcaagaat ctaacacgtg caatcaacaa     3600
aaacaagtgc gacattgctg acctgaaaat ggccgttagc ttcagtcaat tcaacagaag    3660
gtttctaaat gttgtgcggc aattttcaga caatgctgga ataacaccag caatatcctt    3720
ggacttaatg acagatgctg aactagccag agctgtttcc aacatgccaa catctgcagg    3780
acaaataaaa ctgatgttgg agaaccgtgc aatggtaaga agaaagggt tcggaatcct     3840 gataggagtt tacggaagct ccgtaattta catggtgcaa ctgccaatct ttggagttat    3900
agacacgcct tgctggatag taaaagcggc cccttcttgc tcagaaaaaa agggaaacta    3960
tgcttgcctt ttaagagaag atcaaggatg gtattgtcag aatgcagggt caactgttta    4020
ctacccaaat gaaaaagact gcgaaacaag aggagaccat gtcttttgcg acacagcagc    4080
aggaatcaat gttgctgagc agtcaaagga gtgcaacatc aacatatcca ctactaatta    4140
cccatgcaaa gttagcacag gaagacaccc tatcagtatg gttgcactgt ctcctcttgg    4200
ggctttggtt gcttgctaca agggagtgag ctgttccatt ggcagcaaca gagtagggat    4260
catcaagcaa ctgaacaaag gctgctctta tataaccaac caagacgcag acacagtgac    4320
aatagacaac actgtatacc agctaagcaa agttgagggc gaacagcatg ttataaaagg    4380
aaggccagtg tcaagcagct ttgatccagt caaatttcct gaagatcaat tcaatgttgc    4440
acttgaccaa gttttcgaaa gcattgagaa cagtcaggcc ttggtggatc aatcaaacag    4500
aatcctaagc agtgcagaga aaggaaacac tggcttcatc attgtaataa ttctaattgc    4560
tgtccttggc tctaccatga tcctagtgag tgtttttatc ataataaaga aacaaagaa     4620 acccacagga gcacctccag agctgagtgg tgtcacaaac aatggcttca taccacataa    4680
ttagttaatt aaaaataaag taaattaaat taaaataaaa taaaattaaa attaaaataa    4740
aataaaaata aaaatttggg acaaatcata atgtctcgca aggctccatg caaatatgaa    4800
gtgcggggca aatgcaatag aggaagtgag tgcaagttta accacaatta ctggagttgg    4860
ccagatagat acttactaat aagatcaaat tatttattaa atcaacttt aaggaacact     4920 gatagagctg atggcttatc aataatatca ggagcaggca gagaagatag gacacaagat    4980
tttgtcctag gttccaccaa tgtggttcaa ggttatattg atgataacca aagcataaca    5040
aaagctgcag cctgttacag tctacataat ataatcaaac aactcaagga agttgaagtt    5100
aggcaggcta gagataacaa accatctgac agcaaacatg tggcacttca caacttagtc    5160
ctatcttata tggagatgag caaaattcct gcatctttaa tcaacaatct caaaagactg    5220
ccgagagaga aactgaaaaa attagcaaag cttataattg acttatcagc aggtgctgaa    5280
aatgactctt catatgcctt gcaagacagt gaaagcacta atcaagtgca gtgagcatgg    5340
tcctgttttc attactatag aggttgatta catgatatgg actcataagg acttaaaaga    5400
agctttatct aatgggatag tgaagtctca tactaacatt tacaattgtt atttagaaaa    5460
```

```
catagaaatt atatatgtca aggcttactt aagttagtaa aaacacatca gagtgggaca    5520
agtagttatg gaggtgaaag tggagaacat tcgaacaata gatatgctca aagcaagagt    5580
gaaaaatcgt gtggcacgca gcaaatgctt taaaaatgcc tctttgatcc taataggaat    5640
aactacattg agtatagccc tcaatatcta tctaatcata aactatacaa tgcaagaaaa    5700
cacatccgaa tcagaacatc acaccagctc atcacccatg gaatccagca gggaaactcc    5760
aacagtccct atggacaact cagacaccaa tccaggctca cagtatccaa ctcaacagtc    5820
cacagaaggc tccacactct actttgcagc ctcagcaagc tcaccagaga cagaaccaac    5880
atcaacacca gacacaacaa gccgcccgcc cttcgtcgac acacacacaa cactaccaag    5940
tgcaagcaga acaaggacaa gtccggcagt ccacacaaaa aacaatccaa ggacaagccc    6000
cagaacacat tccccaccat gggcaatgac aaggacggtc cgtggaacca ccactctccg    6060
cacaagcagc acaagaaaaa gaccgtccac agcatcagtc caacctgaca gcagcgcaac    6120
aacccacaaa cacgaagaag caagcccagt gagcccgcaa acatctgcga gcacagcaag    6180
accacaaagg aagggcatgg aggccagcac atcaacaaca tacaaccaaa ctagttaaca    6240
aaaaatacaa aataactcta agataaacca tatagacacc aacaattgag aagccaaaag    6300
gcaattcaca atctctccaa aaaggcaaca acaccatatt agctccgctt aaatctccct    6360
ggaaaaaaca ctcgcccata taccaactat accacaacca tcccaagaaa aaagctgggg    6420
taaaacaaca cccaagagac aaataacaat ggatcctctt aatgaatcca ctgttaatgt    6480
ctatcttccc gactcatatc ttaaaggagt gatttctttt agtgagacta atgcaattgg    6540
ttcatgtctc ttaaaaagac cttacctaaa aaatgacaac actgcaaaag ttgccataga    6600
gaatcctgtt atcgagcatg ttagactcaa aaatgcaatc aattctaaga tgaaaatatc    6660
agattacagg atagtagagc cagtaaacat gcaacatgaa attatgaaga atgtacacag    6720
ttgtgagctc acattattaa aacagttttt aacaaggagt aaaaatatta gcactcttaa    6780
attaaatatg atatgtgatt ggctgcagtt aaagtctaca tcagatgata cctcaatctt    6840
aagttttata gatgtagaat ttataccgag ctgggtaagc aattggttta gtaattggta    6900
caatctcaac aagttgattc tggaattcag gaaagaagaa gtaataagaa ctggttcaat    6960
cttgtgtagg tcattgggta aattagtttt tgttgtatca tcatacggat gtatagtcaa    7020
gagcaacaaa agcaaaagag tgagcttctt cacatacaat caactgttaa catggaaaga    7080
tgtgatgtta agtagattca atgcaaattt ctgtatatgg gtaagcaaca gtctgaatga    7140
aaatcaagaa gggttagggt tgagaagtaa tctgcaaggc atattaacta ataagctata    7200
tgaaactgta gattatatgc ttagtttgtg ttgcaatgaa ggtttctcac ttgtgaaaga    7260
gtttgagggt tttattatga gtgaaatcct taggattact gaacatgctc aattcagtac    7320
tagatttaga aatactttat taaatggatt aactgatcaa ttgacaaaat taaaaaataa    7380
aaacagactc agagttcatg gtaccgtgtt agaaaataat gattatccaa tgtatgaagt    7440
tgtacttaaa ttattaggag atacttgag atgtattaaa ttattaatca ataaaaactt    7500
agagaatgct gctgaattat actatatatt tagaatattc ggtcacccaa tggtagatga    7560
aagagatgca atggatgctg tcaaattaaa caatgaaatc acaaaaatcc tcaggttgga    7620
gagcttgaca gaactaagag gggcattcat attaaggatt atcaaaggat tgtagacaa    7680 caacaaaaga tggccgaaaa ttaaaaactt aaaagtgctt agtaaaagat ggactatgta    7740
cttcaaagca aaaagttacc ctagtcaact tgaattaagt gaacaagatt ttttagagct    7800
```

```
tgctgcaata cagtttgaac aagagttttc tgttcctgaa aaaaccaacc ttgagatggt    7860
attaaatgat aaagctatat cacctcctaa aagattaatt tggtctgtgt acccaaaaaa    7920
ttacttacct gagacaataa aaaatcgata tctagaagag actttcaatg caagtgatag    7980
tctcaaaaca agaagagtac tagagtacta tttgaaagat aataaattcg accaaaagaa    8040
acttaaaagt tatgtggtta aacaagaata tttaaatgat aaggatcata ttgtctcgct    8100
aactggaaaa gaaagagaat taagtgtagg tagaatgttt gctatgcaac caggaaaaca    8160
gcgacaaata caaatattgg ctgaaaaatt gttagctgat aatattgtac ccttttccc     8220 agaaacttta acaaagtatg gtgatctaga tcttcagaga ataatggaaa tcaaatcaga    8280
actttcttct attaaaacca gaagaaatga tagttataat aattacattg caagagcatc    8340
catagtaaca gatttaagta agttcaacca agcctttagg tatgaaacta cagcgatctg    8400
tgcggatgta gcagatgaac tacatggaac acaaagccta ttctgttggt tacatcttat    8460
cgttcctatg actacaatga tatgtgccta tagacatgca ccaccagaaa caaaaggtga    8520
atatgatata gataagatag aagagcaaag tggtttatat agatatcata tgggtggtat    8580
tgaaggatgg tgtcaaaaac tctggacaat ggaagctata tctttattag atgttgtatc    8640
tgtaaagaca cgatgtcaaa tgacatcttt attaaacggt gacaaccaat caatagatgt    8700
aagtaaacca gttaagttat ctgagggttt agatgaagtg aaagcagatt atagcttggc    8760
tgtaaaaatg ctaaaagaaa taagagatgc atacagaaat ataggccata aacttaaaga    8820
aggggaaaca tatatatcaa gagatcttca gtttataagt aaggtgattc aatctgaagg    8880
agtaatgcat cctacccctc taaaaagat cttaagagtg ggaccatgga taaacacaat     8940
attagatgac attaaaacca gtgcagagtc aatagggagt ctatgtcagg aattagaatt    9000 tagggggaa agcataatag ttagtctgat attaaggaat ttttggctgt ataatttata     9060
catgcatgaa tcaaagcaac acccctagc agggaagcag ttattcaaac aactaaataa      9120
aacattaaca tcagtgcaga gattttttga aattaaaaag gaaatgaag tagtagatct      9180 atggatgaac ataccaatgc agtttggagg aggagatcca gtagtcttct atagatcttt    9240
ctatagaagg acccctgatt ttttaactga agcaatcagt catgtagata ttctgttaaa    9300
aatatcagcc aacataagaa atgaagcgaa aataagtttc ttcaaagcct tactgtcaat    9360
agaaaaaaat gaacgtgcta cactgacaac actaatgaga gaccctcaag ctgtgggctc    9420
agagcgacaa gcaaaagtaa caagtgatat caatagaaca gcagttacca gcatcttaag    9480
tctttctcca aatcaacttt tcagcgatag tgctatacac tacagtagaa atgaagaaga    9540
ggtcggaatc attgctgaca acataacacc tgtttatcct catggactga gagttttgta    9600
tgaatcatta cctttcata aagctgaaaa agttgtaaat atgatatcag gaacaaaatc      9660
cataaccaac ttattacaga gaacatctgc tattaatggt gaagatattg acagagctgt    9720
atccatgatg ctggagaacc taggattatt atctagaata ttgtcagtag ttgttgatag    9780
tatagaaatt ccaaccaaat ctaatggtag gctgatatgt tgtcagatat ctagaaccct    9840
aagggagaca tcatggaata atatggaaat agttggagta acatccccta gcatcactac    9900
atgcatggat gtcatatatg caactagctc tcatttgaaa gggataatca ttgaaaagtt    9960
cagcactgac agaactacaa gaggtcaaag aggtccaaag agcccttggg taggatcgag   10020
cacgcaagag aaaaaattag ttcctgttta acagacaa attctttcaa acaacaaag       10080 agaacagcta gaagcaattg gaaaaatgag atgggtatat aaagggacac caggtttaag    10140
acgattactc aataagattt gtcttggaag tttaggcatt agttacaaat gtgtaaaacc    10200
```

```
tttattacct aggtttatga gtgtaaattt cctacacagg ttatctgtca gtagtagacc    10260
tatggaattc ccagcatcag ttccagctta tagaacaaca aattaccatt ttgacactag    10320
tcctattaat caagcactaa gtgaaagatt tgggaatgaa gatattaatt tggtcttcca    10380
aaatgcaatc agctgtggaa ttagcataat gagtgtagta gaacaattaa ctggtaggag    10440
tccaaaacag ttagttttaa taccccaatt agaagaaata gacattatgc caccaccagt    10500
gtttcaaggg aaattcaatt ataagctagt agataagata acttctgacc aacatatctt    10560
cagtccagac aaaatagata tgttaacact ggggaaaatg ctcatgccaa ctataaaagg    10620
tcagaaaaca gatcagttct tgaacaagag agagaattat ttccatggga acaatcttat    10680
tgagtctttg tcagcagcgt tagcatgtca ttggtgtggg atattaacag agcaatgtat    10740
agaaaataat attttcaaga aagactgggg tgacgggttc atatcggatc atgcttttat    10800
ggacttcaaa atattcctat gtgtctttaa aactaaactt ttatgtagtt ggggatccca    10860
agggaaaaac attaaagatg aagatatagt agatgaatcg atagataaac tgttaaggat    10920
tgataatact ttttggagaa tgttcagcaa ggttatgttt gaatcaaagg ttaagaaaag    10980
gataatgtta tatgatgtaa aatttctatc attagtaggt tatataggggt ttaagaattg    11040 gtttatagaa cagttgagat cagctgagtt gcatgaggta ccttggattg tcaatgccga    11100
aggtgatctg gttgagatca agtcaattaa aatctatttg caactgatag agcagagttt    11160 attttaaga ataactgttt tgaactatac agatatggca catgctctca caagattaat    11220
cagaaagaag ttgatgtgtg ataatgcact attaacttca attccatccc caatggttaa    11280
cttaactcaa gttattgatc ctacagaaca attagcttat ttccctaaga taacatttga    11340
aaggctaaaa aattatgaca ctagttcaaa ttatgctaaa ggaaagctaa caaggaatta    11400
catgatactg ttgccatggc aacatgttaa tagatataac tttgtcttta gttctactgg    11460
atgtaaagtt agtctaaaaa catgcattgg aaaacttatg aaagatctaa accctaaagt    11520
tctgtacttt attggagaag gggcaggaaa ttggatggcc agaacagcat gtgaatatcc    11580
tgacatcaaa tttgtataca gaagtttaaa agatgacctt gatcatcatt atcctttgga    11640
ataccagaga gtgataggag aattaagcag gataatagat agtggtgaag ggcttttcaat    11700 ggaaacaaca gatgcaactc aaaaaaactca ttgggatttg atacacagag taagcaaaga    11760
tgctttatta ataactttat gtgatgcaga atttaaggac agagatgatt ttttttaagat    11820 ggtaattcta tggaggaaac atgtattatc atgcagaatt tgcactacct atgggacaga    11880
cctctattta ttcgcaaagt atcatgctaa agactgcaat ataaaattac cttttttttgt    11940 gagatcagtt gccacctta ttatgcaagg tagtaaactg tcaggctcgg aatgctacat    12000
actcttaaca ctaggccacc acaacaattt accttgtcat ggagaaatac aaaattctaa    12060
gatgaaaata gcagcgtgta atgatttta tgctgcaaaa aaacttgaca ataaatcaat    12120
tgaagccaac tgtaaatcac ttttatcagg ctaagaata ccgataaata agaaggaatt    12180
aaatagacag agaaggttat taacactaca aagcaaccat tcttctgtag caacagttgg    12240
aggtagcaag gtcatagagt ctaaatggtt aacaaacaag gcaaacacaa taattgattg    12300
gttagaacat attttaaatt ctccaaaagg tgaattaaat tatgattttt ttgaagcatt    12360
agaaaatact taccctaata tgattaaact aatagataat ctagggaatg cagagattaa    12420
aaaactgatc aaagtaactg gatatatgct tgtaagtaaa aaatgaaaaa tgataaaaat    12480
gataaaatag gtgacaactt catactattc caaagtaatc atttgattat gcaattatgt    12540
```

```
aatagttaat taaaaactaa aaatcaaaag ttaaaaacta ataactgtca ttaagtttat    12600
taaaaataag aaattataat tggatgtata cggttttttt gccgt                   12645

<210> SEQ ID NO 3
<211> LENGTH: 12473
<212> TYPE: DNA
<213> ORGANISM: human metapneumovirus

<400> SEQUENCE: 3
gcgaaaaaaa cgcgtataaa ttagattaca aaaaatatg ggacaagtga aaatgtctct      60
tcaagggatt cacctgagtg atctatcata caagcatgct atattaaaag agtctcagta    120
cacaataaaa agagatgtgg gtacaacaac tgcagtgaca ccctcatcat gcaacaaga    180 ataacgctg ttgtgtggag aaattctgta tgctaaacat gctgattaca atatgctgc     240 agaaatagga atacaatata ttagcacagc tttaggatca gagagagtgc agcagattct    300
gaggaactca ggcagtgaag tccaagtggt cttaaccaga acgtactctc tggggaaagt    360
taaaaacaat aaaggagaag atttacagat gttagacata cacggggtag agaagagctg    420
ggtagaagag atagacaaag aagcaaggaa acaatggca accttgctta aggaatcatc      480
aggtaatatc ccacaaaatc agaggccctc agcaccagac acaccataa tcttattatg     540 tgtaggtgca ttaatattta ctaagctagc atcaaccata gaagtgggac tagagaccac    600
agtcagaagg gctaaccgtg tactaagtga tgcactcaag agatacccta gaatggacat     660
cccaaaaatt gccagatcct tctatgactt atttgaacaa aaagtgtatc acagaagttt    720
gttcattgag tatggcaaag cattaggctc atcatctaca ggcagcaaag cagaaagtct    780
atttgttaat atattcatgc aagcttatgg agccggtcaa acaatgctaa ggtgggggt    840 cattgccagg tcatccaaca atataatgtt aggacatgta tctgtccaag ctgagttaaa    900
acaggtcaca gaagtctatg acttggtgcg agaaatgggc cctgaatctg gacttctaca    960
tttaaggcaa agcccaaaag ctggactgtt atcactagcc aactgtccca actttgcaag   1020
tgttgttctc ggaaatgcct caggcttagg cataatcggt atgtatcgtg ggagagtacc    1080 aaaacacagaa ttattttcag cagcagaaag ttatgccaaa agtttgaaag agagcaataa  1140
aatcaatttc tcttcattag gacttacaga tgaagagaaa gaggctgcag aacatttctt    1200
aaatgtgagt gacgacagtc aaatgattaa tgagtaatta aaaagtgggg acaagtcaaa   1260
atgtctttcc ctgaaggaaa agatattctt ttcatgggta atgaagcagc aaaattagca    1320 gaagcttttcc agaaatcatt aaggaaacca agtcataaaa gatctcaatc tattatagga    1380
gaaaaagtga acactgtatc agaaacattg gaattaccta ctatcagtag acctgcaaaa    1440
ccaaccatac tgtcagaacc aaagttagca tggactgata aggtggggc aatcaaaact    1500 gaaataaagc aagcaatcaa agtcatggat cctattgagg aagaagagtc tactgagaag    1560
aaggtgctgc cctccagtga tgggaaaacc cctgcagaaa agaaactgaa accatcaact    1620
aacaccaaaa agaaagtttc gtttacacca aatgaaccag aaaatatac aaagttggaa    1680 aaagatgctc tagatttgct ctcagataat gaagaagaag atgcagaatc ttcaatctta    1740 accttgaag aaagagatac ttcatcgtta agcattgagg ccagattgga atcaatagag    1800
gagaaattaa gcatgatatt agggctatta agaacactca cattgctac agcaggaccc    1860 acagcagcaa gagatgggat cagagatgca atgattggcg taagagagga attaatagca    1920
gacataataa aggaagccaa agggaaagca gcagaaatga tggaagagga aatgagtcaa    1980
cgatcaaaaa taggaaacgg tagtgtaaaa ctaacagaga agcaaaaga gcttaacaaa    2040
```

```
attgttgaag atgaaagcac aagtggagaa tctgaagaag aagaagaacc aaaagacata    2100
caagacaata gtcaagaaga tgacatttac cagttaatta tgtagtttaa taaaaataaa    2160
caatgggaca agtaaaaatg gagtcctacc tagtagacac ttatcaaggc attccttaca    2220
cagcagctgt tcaagttgat ctaatagaaa aggacctgtt acctgcaagc ctaacaatat    2280
ggttcccttt gtttcaggcc aacacaccac cagcagtgct gctcgatcag ttgaaaaccc    2340
taacaataac cactctgtat gctgcatcac aaaatggtcc aatactcaaa gtgaatgcat    2400
cagcccaagg tgcagcaatg tctgtacttc ccaaaaaatt tgaagtcaat gcgactgtag    2460
cactcgatga atatagcaaa ttggaatttg acaaactcac agtctgtgaa gtaaaaacag    2520
tttacttaac aaccatgaaa ccatacggga tggtatcaaa atttgtgagc tcagccaaat    2580
cagttggcaa aaaaacacat gatctaatcg cactgtgtga ttttatggat ctagaaaaga    2640
acacacctgt tacaatacca gcattcatca aatcagtttc aatcaaagag agtgagtcag    2700
ctactgttga agctgctata agcagtgaag cagaccaagc tctaacacag gccaaaattg    2760
caccttatgc gggattgatt atgatcatga ctatgaacaa tcccaaaggc atattcaaaa    2820
agcttggagc tgggactcaa gttatagtag aactaggagc atatgtccag gctgaaagca    2880
taagtaaaat atgcaagact tggagccatc aagggacaag atatgtgttg aagtccagat    2940
aacagccaag caccttggcc aagagctact aactctatct catagattat aaagtcacca    3000
ttctagttat ataaaaatca agttagaaca agaattaaat caatcaagaa tgggacaaat    3060
aaaaatgtct tggaaagtgg tgatcatttt ttcattgtta ataacacctc aacacggtct    3120
taaagagagc tatttagaag agtcatgtag cactataact gaaggatatc tcagtgttct    3180
gaggacaggt tggtatacca acgtttttac actggaggta ggtgatgtag agaaccttac    3240
atgtgctgat ggacctagct taataaaaac agaattagac ctgaccaaaa gtgcactaag    3300
agaactcaga acagttcctg ctgatcaact ggcaagagag gagcaaattg agaatcccag    3360
acaatctaga tttgttctag gagcaatagc actcggtgtt gcaacagcag ctgcagttac    3420
agcaggtgtt gcaattgcca aaaccatccg gcttgaaagt gaagtaacag caattaagaa    3480
tgccctcaaa aagaccaatg aagcagtatc tacattgggg aatggagttc gagtgttggc    3540
aactgcagtg agggagctgg aagattttgt gagcaagaat ctaacacgtg caatcaacaa    3600
aaacaagtgc gacattgctg acctgaaaat ggccgttagc ttcagtcaat tcaacagaag    3660
gtttctaaat gttgtgcggc aattttcaga caatgctgga ataacaccag caatatcctt    3720
ggacttaatg acagatgctg aactagccag agctgtttcc aacatgccaa catctgcagg    3780
acaaataaaa ctgatgttgg agaaccgtgc aatggtaaga agaaaggggt tcggaatcct    3840
gataggagtt tacggaagct ccgtaattta catggtgcaa ctgccaatct ttggagttat    3900
agacacgcct tgctggatag taaaagcggc cccttcttgc tcagaaaaaa agggaaacta    3960
tgcttgcctt ttaagagaag atcaaggatg gtattgtcag aatgcagggt caactgttta    4020
ctacccaaat gaaaaagact gcgaaacaag aggagaccat gtcttttgcg acacagcagc    4080
aggaatcaat gttgctgagc agtcaaagga gtgcaacatc aacatatcca ctactaatta    4140
cccatgcaaa gttagcacag aagacaccc tatcagtatg gttgcactgt ctcctctttgg    4200 ggctttggtt gcttgctaca agggagtgag ctgttccatt ggcagcaaca gagtagggat    4260
catcaagcaa ctgaacaaag gctgctctta taaccaaac caagacgcag acacagtgac    4320
aatagacaac actgtatacc agctaagcaa agttgagggc aacagcatg ttataaaagg    4380
```

```
aaggccagtg tcaagcagct tgatccagt  caaatttcct gaagatcaat tcaatgttgc    4440
acttgaccaa gttttcgaaa gcattgagaa cagtcaggcc ttggtggatc aatcaaacag    4500
aatcctaagc agtgcagaga aaggaaacac tggcttcatc attgtaataa ttctaattgc    4560
tgtccttggc tctaccatga tcctagtgag tgttttatc  ataataaaga aaacaaagaa    4620
acccacagga gcacctccag agctgagtgg tgtcacaaac aatggcttca taccacataa    4680
ttagttaatt aaaaataaag taaattaaat taaaataaaa taaaattaaa attaaaataa    4740
aataaaaata aaaatttggg acaaatcata atgtctcgca aggctccatg caaatatgaa    4800
gtgcggggca aatgcaatag aggaagtgag tgcaagttta accacaatta ctggagttgg    4860
ccagatagat acttactaat aagatcaaat tatttattaa atcaactttt aaggaacact    4920
gatagagctg atggcttatc aataatatca ggagcaggca gagaagatag acacaagat    4980 tttgtcctag gttccaccaa tgtggttcaa ggttatattg atgataacca aagcataaca    5040
aaagctgcag cctgttacag tctacataat ataatcaaac aactacaaga agttgaagtt    5100
aggcaggcta gagataacaa accatctgac agcaaacatg tggcacttca caacttagtc    5160
ctatcttata tggagatgag caaaattcct gcatctttaa tcaacaatct caaaagactg    5220
ccgagagaga aactgaaaaa attagcaaag cttataattg acttatcagc aggtgctgaa    5280
aatgactctt catatgcctt gcaagacagt gaaagcacta atcaagtgca gtgagcatgg    5340
tcctgttttc attactatag aggttgatta catgatatgg actcataagg acttaaaaga    5400
agctttatct aatgggatag tgaagtctca tactaacatt tacaattgtt atttagaaaa    5460
catagaaatt atatatgtca aggcttactt aagttagtaa aaacacatca gagtgggata    5520
aatgacaatg ataacattag atgtcattaa aagtgatggg tcttcaaaaa catgtactca    5580
cctcaaaaaa ttaattaaag accactctgg taaagtgctt attgtactta agttaatatt    5640
agctttacta acatttctca cagtgacaat caccatcaat tatataaaag tagaaaacaa    5700
tctgcaaata tgtcagtcaa aaactgaatc agacaaaaag gactcatcat caaataccac    5760
atcagtcaca accaagacta ctctaaatca tgatataaca cagtattta  aaagtttgat    5820 tcaaaggtat acaaactctg caataaacag agacacatgc tggaaaataa gcagaaatca    5880
atgcacaaac ataacaacat acaaattttt atgttttaaa tctgaagaaa caaaaaccaa    5940
caattgtgat aaactgacag atttatgcag aaacaaacca aaaccagctg ttgaagtgta    6000
tcacatagta gaatgccatt gtatatacac agttaaatgg aagtgctatc attacccaat    6060
agatgaaacc caatcctaaa taacactaga ttaggatcca tccaagtctg ttagttcaac    6120
aatttagtta tttaaaaata ttttgaaaac aagtaagttt ctatgatact tcataataat    6180
aagtaataat taattgctta atcatcatca caacattatt cgaaaccata actattcaat    6240
ttaagaagta aaacaataa  tatgagacaa ataacaatgg atcctcttaa tgaatccact    6300
gttaatgtct atcttcccga ctcatatctt aaaggagtga tttctttag  tgagactaat    6360 gcaattggtt catgtctctt aaaaagacct tacctaaaaa atgacaacac tgcaaaagtt    6420
gccatagaga tcctgttat  cgagcatgtt agactcaaaa atgcaatcaa ttctaagatg    6480
aaaatatcag attacaggat agtagagcca gtaaacatgc aacatgaaat tatgaagaat    6540
gtacacagtt gtgagctcac attattaaaa cagttttaa  caaggagtaa aaatattagc    6600
actcttaaat taaatatgat atgtgattgg ctgcagttaa agtctacatc agatgatacc    6660
tcaatcttaa gttttataga tgtagaattt ataccaactgct gggtaagcaa ttggtttagt    6720
aattggtaca atctcaacaa gttgattctg gaattcagga aagaagaagt aataagaact    6780
```

```
ggttcaatct tgtgtaggtc attgggtaaa ttagtttttg ttgtatcatc atacggatgt   6840
atagtcaaga gcaacaaaag caaaagagtg agcttcttca catacaatca actgttaaca   6900
tggaaagatg tgatgttaag tagattcaat gcaaatttct gtatatgggt aagcaacagt   6960
ctgaatgaaa atcaagaagg gttagggttg agaagtaatc tgcaaggcat attaactaat   7020
aagctatatg aaactgtaga ttatatgctt agtttgtgtt gcaatgaagg tttctcactt   7080
gtgaaagagt ttgagggttt tattatgagt gaaatcctta ggattactga acatgctcaa   7140
ttcagtacta gatttagaaa tactttatta aatggattaa ctgatcaatt gacaaaatta   7200
aaaaataaaa acagactcag agttcatggt accgtgttag aaaataatga ttatccaatg   7260
tatgaagttg tacttaaatt attaggagat actttgagat gtattaaatt attaatcaat   7320
aaaaacttag agaatgctgc tgaattatac tatatattta gaatattcgg tcacccaatg   7380
gtagatgaaa gagatgcaat ggatgctgtc aaattaaaca atgaaatcac aaaaatcctc   7440
aggttggaga gcttgacaga actaagaggg gcattcatat taaggattat caaaggatt    7500 gtagacaaca acaaaagatg gccgaaaatt aaaaacttaa aagtgcttag taaaagatgg   7560
actatgtact tcaaagcaaa aagttaccct agtcaacttg aattaagtga acaagatttt   7620
ttagagcttg ctgcaataca gtttgaacaa gagttttctg ttcctgaaaa aaccaacctt   7680
gagatggtat taaatgataa agctatatca cctcctaaaa gattaatttg gtctgtgtac   7740
ccaaaaaatt acttacctga gacaataaaa aatcgatatc tagaagagac tttcaatgca   7800
agtgatagtc tcaaaacaag aagagtacta gagtactatt tgaaagataa taaattcgac   7860 caaaagaac ttaaaagtta tgtggttaaa caagaatatt taaatgataa ggatcatatt    7920
gtctcgctaa ctggaaaaga aagagaatta agtgtaggta gaatgttttgc tatgcaacca   7980 ggaaaacagc gacaaataca aatattggct gaaaaattgt tagctgataa tattgtaccc   8040
ttttccccag aaactttaac aaagtatggt gatctagatc ttcagagaat aatggaaatc   8100
aaatcagaac tttcttctat taaaaccaga agaaatgata gttataataa ttacattgca   8160
agagcatcca tagtaacaga tttaagtaag ttcaaccaag cctttaggta tgaaactaca   8220
gcgatctgtg cggatgtagc agatgaacta catggaacac aaagcctatt ctgttggtta   8280
catcttatcg ttcctatgac tacaatgata tgtgcctata gacatgcacc accagaaaca   8340
aaaggtgaat atgatataga taagatagaa gagcaaagtg gtttatatag atatcatatg   8400
ggtggtattg aaggatggtg tcaaaaactc tggacaatgg aagctatatc tttattagat   8460
gttgtatctg taaagacacg atgtcaaatg acatctttat taaacggtga caaccaatca   8520
atagatgtaa gtaaaccagt taagttatct gagggtttag atgaagtgaa agcagattat   8580
agcttggctg taaaaatgct aaaagaaata agagatgcat acagaaatat aggccataaa   8640
cttaaagaag gggaaacata tatcaaga gatcttcagt ttataagtaa ggtgattcaa     8700
tctgaaggag taatgcatcc taccectata aaaaagatct taagagtggg accatggata   8760
aacacaatat tagatgacat taaaaccagt gcagagtcaa tagggagtct atgtcaggaa   8820
ttagaattta ggggggaaag cataatagtt agtctgatat taaggaattt ttggctgtat   8880
aatttataca tgcatgaatc aaagcaacac ccectagcag ggaagcagtt attcaaacaa   8940
ctaaataaaa cattaacatc agtgcagaga ttttttgaaa ttaaaaagga aaatgaagta   9000
gtagatctat ggatgaacat accaatgcag tttggaggag gagatccagt agtcttctat   9060
agatctttct atagaaggac ccctgatttt ttaactgaag caatcagtca tgtagatatt   9120
```

```
ctgttaaaaa tatcagccaa cataagaaat gaagcgaaaa taagtttctt caaagcctta    9180
ctgtcaatag aaaaaaatga acgtgctaca ctgacaacac taatgagaga ccctcaagct    9240
gtgggctcag agcgacaagc aaaagtaaca agtgatatca atagaacagc agttaccagc    9300
atcttaagtc tttctccaaa tcaacttttc agcgatagtg ctatacacta cagtagaaat    9360
gaagaagagg tcggaatcat tgctgacaac ataacacctg tttatcctca tggactgaga    9420
gttttgtatg aatcattacc ttttcataaa gctgaaaaag ttgtaaatat gatatcagga    9480
acaaaatcca taaccaactt attacagaga acatctgcta ttaatggtga agatattgac    9540
agagctgtat ccatgatgct ggagaaccta ggattattat ctagaatatt gtcagtagtt    9600
gttgatagta tagaaattcc aaccaaatct aatggtaggc tgatatgttg tcagatatct    9660
agaaccctaa gggagacatc atggaataat atggaaatag ttggagtaac atcccctagc    9720
atcactacat gcatggatgt catatatgca actagctctc atttgaaagg gataatcatt    9780
gaaaagttca gcactgacag aactacaaga ggtcaaagag gtccaaagag cccttgggta    9840
ggatcgagca cgcaagagaa aaaattagtt cctgtttata acagacaaat tctttcaaaa    9900
caacaaagag aacagctaga agcaattgga aaaatgagat gggtatataa agggacacca    9960
ggtttaagac gattactcaa taagatttgt cttggaagtt taggcattag ttacaaatgt   10020
gtaaaaccct tattacctag gtttatgagt gtaaatttcc tacacaggtt atctgtcagt   10080
agtagaccta tggaattccc agcatcagtt ccagcttata aacaacaaa ttaccatttt    10140 gacactagtc ctattaatca agcactaagt gaaagatttg gaatgaaga tattaatttg    10200 gtcttccaaa atgcaatcag ctgtggaatt agcataatga gtgtagtaga acaattaact   10260
ggtaggagtc aaaacagtt agttttaata ccccaattag aagaaataga cattatgcca    10320
ccaccagtgt ttcaagggaa attcaattat aagctagtag ataagataac ttctgaccaa   10380
catatcttca gtccagacaa aatagatatg ttaacactgg ggaaaatgct catgccaact   10440
ataaaaggtc agaaaacaga tcagttcttg aacaagagag agaattattt ccatgggaac   10500
aatcttattg agtctttgtc agcagcgtta gcatgtcatt ggtgtgggat attaacagag   10560
caatgtatag aaaataatat tttcaagaaa gactgggtg acgggttcat atcggatcat    10620
gcttttatgg acttcaaaat attcctatgt gtctttaaaa ctaaactttt atgtagttgg    10680
ggatcccaag ggaaaacat taagatgaa gatatagtag atgaatcgat agataaactg    10740
ttaaggattg ataatacttt tggagaatg ttcagcaagg ttatgtttga atcaaaggtt    10800
aagaaaagga taatgttata tgatgtaaaa tttctatcat tagtaggtta tagggttt     10860 aagaattggt ttatagaaca gttgagatca gctgagttgc atgaggtacc ttggattgtc    10920
aatgccgaag gtgatctggt tgagatcaag tcaattaaaa tctatttgca actgatagag    10980
cagagtttat ttttaagaat aactgttttg aactatacag atatggcaca tgctctcaca    11040
agattaatca gaaagaagtt gatgtgtgat aatgcactat aacttcaat tccatcccca    11100 atggttaact taactcaagt tattgatcct acagaacaat tagcttattt ccctaagata    11160
acatttgaaa ggctaaaaaa ttatgacact agttcaaatt atgctaaagg aaagctaaca   11220
aggaattaca tgatactgtt gccatggcaa catgttaata gatataactt tgtctttagt    11280
tctactggat gtaaagttag tctaaaaaca tgcattggaa aacttatgaa agatctaaac    11340
cctaaagttc tgtactttat tggagaaggg gcaggaaatt ggatggccag aacagcatgt    11400
gaatatcctg acatcaaatt tgtatacaga agtttaaaag atgaccttga tcatcattat    11460
cctttggaat accagagagt gataggagaa ttaagcagga ataatagata ggtgaaggg    11520
```

```
ctttcaatgg aaacaacaga tgcaactcaa aaaactcatt gggatttgat acacagagta    11580
agcaaagatg ctttattaat aactttatgt gatgcagaat ttaaggacag agatgatttt    11640
tttaagatgg taattctatg gaggaaacat gtattatcat gcagaatttg cactacctat    11700
gggacagacc tctatttatt cgcaaagtat catgctaaag actgcaatat aaaattacct    11760
ttttttgtga gatcagttgc cacctttatt atgcaaggta gtaaactgtc aggctcggaa    11820
tgctacatac tcttaacact aggccaccac aacaatttac cttgtcatgg agaaataCaa    11880
aattctaaga tgaaaatagc agcgtgtaat gatttttatg ctgcaaaaaa acttgacaat    11940
aaatcaattg aagccaactg taaatcactt ttatcagggc taagaatacc gataaataag    12000
aaggaattaa atagacagag aaggttatta acactacaaa gcaaccattc ttctgtagca    12060
acagttggag gtagcaaggt catagagtct aaatggttaa caaacaaggc aaacacaata    12120
attgattggt tagaacatat tttaaattct ccaaaaggtg aattaaatta tgatttttt     12180 gaagcattag aaaatactta ccctaatatg attaaactaa tagataatct agggaatgca    12240
gagattaaaa aactgatcaa agtaactgga tatatgcttg taagtaaaaa atgaaaaatg    12300
ataaaaatga taaataggt gacaacttca tactattcca aagtaatcat ttgattatgc    12360
aattatgtaa tagttaatta aaaactaaaa atcaaaagtt aaaaactaat aactgtcatt    12420
aagtttatta aaaataagaa attataattg gatgtatacg gttttttttgc cgt         12473

<210> SEQ ID NO 4
<211> LENGTH: 14141
<212> TYPE: DNA
<213> ORGANISM: Artificial Sequence
<220> FEATURE:
<223> OTHER INFORMATION: GFP encoding gene is inserted between
      nucleotides 40 and 784

<400> SEQUENCE: 4
gcgaaaaaaa cgcgtataaa ttagattaca aaaaaatatg ggacaagtga aaatggtgag      60
caagggcgag gagctgttca ccggggtggt gcccatcctg gtcgagctgg acggcgacgt     120
aaacggccac aagttcagcg tgtccggcga gggcgagggc gatgccacct acggcaagct     180
gaccctgaag ttcatctgca ccaccggcaa gctgcccgtg ccctggccca ccctcgtgac     240
caccctgacc tacggcgtgc agtgcttcag ccgctacccc gaccacatga agcagcacga     300
cttcttcaag tccgccatgc ccgaaggcta cgtccaggag cgcaccatct tcttcaagga     360
cgacggcaac tacaagaccc gcgccgaggt gaagttcgag ggcgacaccc tggtgaaccg     420
catcgagctg aagggcatcg acttcaagga ggacggcaac atcctggggc acaagctgga     480
gtacaactac aacagccaca acgtctatat catggccgac aagcagaaga acggcatcaa     540
ggtgaacttc aagatccgcc acaacatcga ggacggcagc gtgcagctcg ccgaccacta     600
ccagcagaac acccccatcg gcgacggccc cgtgctgctg cccgacaacc actacctgag     660
cacccagtcc gccctgagca agacccccaa cgagaagcgc gatcacatgg tcctgctgga     720
gttcgtgacc gccgccggga tcactctcgg catggacgag ctgtacaagt aagttaatta     780
aaaagtggga caagtgaaaa tgtctcttca agggattcac ctgagtgatc tatcatacaa     840
gcatgctata ttaaaagagt ctcagtacac aataaaaaga gatgtgggta caacaactgc     900
agtgacaccc tcatcattgc aacaagaaat aacgctgttg tgtggagaaa ttctgtatgc     960
taaacatgct gattacaaat atgctgcaga ataggaata caatatatta gcacagcttt    1020
aggatcagag agagtgcagc agattctgag gaactcaggc agtgaagtcc aagtggtctt    1080
```

```
aaccagaacg tactctctgg ggaaagttaa aaacaataaa ggagaagatt tacagatgtt    1140
agacatacac ggggtagaga agagctgggt agaagagata gacaaagaag caaggaaaac    1200
aatggcaacc ttgcttaagg aatcatcagg taatatccca caaaatcaga ggccctcagc    1260
accagacaca cccataatct tattatgtgt aggtgcatta atatttacta agctagcatc    1320
aaccatagaa gtgggactag agaccacagt cagaagggct aaccgtgtac taagtgatgc    1380
actcaagaga tacccctagaa tggacatccc aaaaattgcc agatccttct atgacttatt    1440
tgaacaaaaa gtgtatcaca gaagtttgtt cattgagtat ggcaaagcat taggctcatc    1500
atctacaggc agcaaagcag aaagtctatt tgttaatata ttcatgcaag cttatggagc    1560
cggtcaaaca atgctaaggt gggggggtcat tgccaggtca tccaacaata taatgttagg    1620
acatgtatct gtccaagctg agttaaaaca ggtcacagaa gtctatgact tggtgcgaga    1680
aatgggccct gaatctggac ttctacattt aaggcaaagc ccaaaagctg gactgttatc    1740
actagccaac tgtcccaact ttgcaagtgt tgttctcgga aatgcctcag gcttaggcat    1800
aatcggtatg tatcgtggga gagtaccaaa cacagaatta ttttcagcag cagaaagtta    1860
tgccaaaagt ttgaaagaga gcaataaaat caatttctct tcattaggac ttacagatga    1920
agagaaagag gctgcagaac atttcttaaa tgtgagtgac gacagtcaaa atgattatga    1980
gtaattaaaa aagtgggaca agtcaaaatg tctttccctg aaggaaaaga tattcttttc    2040
atgggtaatg aagcagcaaa attagcagaa gctttccaga aatcattaag gaaaccaagt    2100
cataaaagat ctcaatctat tataggagaa aaagtgaaca ctgtatcaga aacattggaa    2160
ttacctacta tcagtagacc tgcaaaacca accatactgt cagaaccaaa gttagcatgg    2220
actgataaag gtgggggcaat caaaactgaa ataaagcaag caatcaaagt catggatcct    2280
attgaggaag aagagtctac tgagaagaag gtgctgccct ccagtgatgg gaaaaccccct    2340 gcagaaaaga aactgaaacc atcaactaac accaaaaaga aagtttcgtt tacaccaaat    2400
gaaccaggaa aatatacaaa gttggaaaaa gatgctctag atttgctctc agataatgaa    2460
gaagaagatg cagaatcttc aatcttaacc tttgaagaaa gagatacttc atcgttaagc    2520
attgaggcca gattggaatc aatagaggag aaattaagca tgatattagg gctattaaga    2580
acactcaaca ttgctacagc aggacccaca gcagcaagag atgggatcag agatgcaatg    2640
attggcgtaa gagaggaatt aatagcagac ataataaagg aagccaaagg gaaagcagca    2700
gaaatgatgg aagaggaaat gagtcaacga tcaaaaatag gaaacggtag tgtaaaacta    2760
acagagaaag caaaagagct taacaaaatt gttgaagatg aaagcacaag tggagaatct    2820
gaagaagaag aagaaccaaa agacatacaa gacaatagtc aagaagatga catttaccag    2880
ttaattatgt agtttaataa aaataaacaa tgggacaagt aaaaatggag tcctacctag    2940
tagacactta tcaaggcatt ccttacacag cagctgttca agttgatcta atagaaaagg    3000
acctgttacc tgcaagccta acaatatggt tcccctttgtt tcaggccaac acaccaccag    3060
cagtgctgct cgatcagttg aaaaccctaa caataaccac tctgtatgct gcatcacaaa    3120
atggtccaat actcaaagtg aatgcatcag cccaaggtgc agcaatgtct gtacttccca    3180
aaaaatttga agtcaatgcg actgtagcac tcgatgaata tagcaaattg gaatttgaca    3240
aactcacagt ctgtgaagta aaaacagttt acttaacaac catgaaacca tacgggatgg    3300
tatcaaaatt tgtgagctca gccaaatcag ttggcaaaaa aacacatgat ctaatcgcac    3360
tgtgtgattt tatggatcta gaaaagaaca cacctgttac aataccagca ttcatcaaat    3420
```

```
cagtttcaat caaagagagt gagtcagcta ctgttgaagc tgctataagc agtgaagcag   3480
accaagctct aacacaggcc aaaattgcac cttatgcggg attgattatg atcatgacta   3540
tgaacaatcc caaaggcata ttcaaaaagc ttggagctgg gactcaagtt atagtagaac   3600
taggagcata tgtccaggct gaaagcataa gtaaaatatg caagacttgg agccatcaag   3660
ggacaagata tgtgttgaag tccagataac agccaagcac cttggccaag agctactaac   3720
tctatctcat agattataaa gtcaccattc tagttatata aaaatcaagt tagaacaaga   3780
attaaatcaa tcaagaatgg gacaaataaa aatgtcttgg aaagtggtga tcattttttc   3840
attgttaata cacctcaac acggtcttaa agagagctat ttagaagagt catgtagcac    3900
tataactgaa ggatatctca gtgttctgag gacaggttgg tataccaacg tttttacact   3960
ggaggtaggt gatgtagaga accttacatg tgctgatgga cctagcttaa taaaaacaga   4020
attagacctg accaaaagtg cactaagaga actcagaaca gtttctgctg atcaactggc   4080
aagagaggag caaattgaga atcccagaca atctagattt gttctaggag caatagcact   4140
cggtgttgca acagcagctg cagttacagc aggtgttgca attgccaaaa ccatccggct   4200
tgaaagtgaa gtaacagcaa ttaagaatgc cctcaaaaag accaatgaag cagtatctac   4260
attggggaat ggagttcgag tgttggcaac tgcagtgagg gagctggaag attttgtgag   4320
caagaatcta acacgtgcaa tcaacaaaaa caagtgcgac attgctgacc tgaaaatggc   4380
cgttagcttc agtcaattca acagaaggtt tctaaatgtt gtgcggcaat ttcagacaa    4440 tgctggaata caccagcaa tatccttgga cttaatgaca gatgctgaac tagccagagc    4500
tgtttccaac atgccaacat ctgcaggaca aataaaactg atgttggaga accgtgcaat   4560
ggtaagaaga aaggggttcg gaatcctgat aggagtttac ggaagctccg taatttacat   4620
ggtgcaactg ccaatctttg gagttataga cacgccttgc tggatagtaa aagcggcccc   4680
ttcttgctca gaaaaaaagg gaaactatgc ttgcctttta agagaagatc aaggatggta   4740
ttgtcagaat gcagggtcaa ctgtttacta cccaaatgaa aaagactgcg aaacaagagg   4800
agaccatgtc tttttgcgaca cagcagcagg aatcaatgtt gctgagcagt caaaggagtg   4860
caacatcaac atatccacta ctaattaccc atgcaaagtt agcacaggaa gacacccctat  4920 cagtatggtt gcactgtctc ctcttgggc tttggttgct tgctacaagg gagtgagctg     4980
ttccattggc agcaacagag tagggatcat caagcaactg aacaaggct gctcttatat     5040 aaccaaccaa gacgcagaca cagtgacaat agacaacact gtataccagc taagcaaagt   5100
tgagggcgaa cagcatgtta taaaggaag gccagtgtca agcagctttg atccagtcaa    5160
atttcctgaa gatcaattca atgttgcact tgaccaagtt ttcgaaagca ttgagaacag   5220
tcaggccttg gtggatcaat caaacagaat cctaagcagt gcagagaaag gaaacactgg   5280
cttcatcatt gtaataattc taattgctgt ccttggctct accatgatcc tagtgagtgt   5340
ttttatcata ataagaaaa caaagaaacc cacaggagca cctccagagc tgagtggtgt    5400
cacaaacaat ggcttcatac cacataatta gttaattaaa aataaagtaa attaaattaa   5460
aataaaataa aattaaaatt aaaataaaat aaaaataaaa atttgggaca aatcataatg   5520
tctcgcaagg ctccatgcaa atatgaagtg cggggcaaat gcaatagagg aagtgagtgc   5580
aagtttaacc acaattactg gagttggcca gatagatact tactaataag atcaaattat   5640
ttattaaatc aacttttaag gaacactgat agagctgatg gcttatcaat aatatcagga   5700
gcaggcagag aagataggac acaagatttt gtcctaggtt ccaccaatgt ggttcaaggt   5760
tatattgatg ataaccaaag cataacaaaa gctgcagcct gttacagtct acataatata   5820
```

```
atcaaacaac tacaagaagt tgaagttagg caggctagag ataacaaacc atctgacagc    5880
aaacatgtgg cacttcacaa cttagtccta tcttatatgg agatgagcaa aattcctgca    5940
tctttaatca acaatctcaa aagactgccg agagagaaac tgaaaaaatt agcaaagctt    6000
ataattgact tatcagcagg tgctgaaaat gactcttcat atgccttgca agacagtgaa    6060
agcactaatc aagtgcagtg agcatggtcc tgttttcatt actatagagg ttgattacat    6120
gatatggact cataaggact taaaagaagc tttatctaat gggatagtga agtctcatac    6180
taacatttac aattgttatt tagaaaacat agaaattata tatgtcaagg cttacttaag    6240
ttagtaaaaa cacatcagag tgggataaat gacaatgata acattagatg tcattaaaag    6300
tgatgggtct tcaaaaacat gtactcacct caaaaaatta attaaagacc actctggtaa    6360
agtgcttatt gtacttaagt taatattagc tttactaaca tttctcacag tgacaatcac    6420
catcaattat ataaaagtag aaaacaatct gcaaatatgt cagtcaaaaa ctgaatcaga    6480
caaaaaggac tcatcatcaa ataccacatc agtcacaacc aagactactc taaatcatga    6540
tataacacag tattttaaaa gtttgattca aaggtataca aactctgcaa taaacagaga    6600
cacatgctgg aaaataagca gaaatcaatg cacaaacata acaacataca aattttatg    6660 ttttaaatct gaagaaacaa aaaccaacaa ttgtgataaa ctgacagatt tatgcagaaa    6720
caaaccaaaa ccagctgttg aagtgtatca catagtagaa tgccattgta tatacacagt    6780
taaatggaag tgctatcatt acccaataga tgaaacccaa tcctaaataa cactagatta    6840
ggatccatcc aagtctgtta gttcaacaat ttagttattt aaaaatattt tgaaaacaag    6900
taagtttcta tgatacttca taataataag taataattaa ttgcttaatc atcatcacaa    6960
cattattcga aaccataact attcaattta agaagtaaaa acaataatat gggacaagta    7020
gttatggagg tgaaagtgga gaacattcga acaatagata tgctcaaagc aagagtgaaa    7080
aatcgtgtgg cacgcagcaa atgctttaaa aatgcctctt tgatcctaat aggaataact    7140
acattgagta tagccctcaa tatctatcta atcataaact atacaatgca agaaaacaca    7200
tccgaatcag aacatcacac cagctcatca cccatggaat ccagcaggga aactccaaca    7260
gtccctatgg acaactcaga caccaatcca ggctcacagt atccaactca acagtccaca    7320
gaaggctcca cactctactt tgcagcctca gcaagctcac cagagacaga accaacatca    7380
acaccagaca caacaagccg cccgcccttc gtcgacacac acacaacact accaagtgca    7440
agcagaacaa ggacaagtcc ggcagtccac acaaaaaaca atccaaggac aagccccaga    7500
acacattccc caccatgggc aatgacaagg acggtccgtg gaaccaccac tctccgcaca    7560
agcagcacaa gaaaaagacc gtccacagca tcagtccaac ctgacagcag cgcaacaacc    7620
cacaaacacg aagaagcaag cccagtgagc ccgcaaacat ctgcgagcac agcaagacca    7680
caaaggaagg gcatggaggc cagcacatca acaacataca accaaactag ttaacaaaaa    7740
atacaaaata actctaagat aaaccatata gacaccaaca attgagaagc aaaaggcaa    7800 ttcacaatct ctccaaaaag gcaacaacac catattagct ccgcttaaat ctccctggaa    7860
aaaacactcg cccatatacc aactatacca caaccatccc aagaaaaaaa gctgggtaaa    7920
acaacaccca agagacaaat aacaatggat cctcttaatg aatccactgt taatgtctat    7980
cttcccgact catatcttaa aggagtgatt tcttttagtg agactaatgc aattggttca    8040
tgtctcttaa aaagacctta cctaaaaaat gacaacactg caaagttgc catagagaat    8100 cctgttatcg agcatgttag actcaaaaat gcaatcaatt ctaagatgaa aatatcagat    8160
```

```
tacaggatag tagagccagt aaacatgcaa catgaaatta tgaagaatgt acacagttgt    8220
gagctcacat tattaaaaca gttttaaca aggagtaaaa atattagcac tcttaaatta    8280
aatatgatat gtgattggct gcagttaaag tctacatcag atgatacctc aatcttaagt    8340
tttatagatg tagaatttat acctagctgg gtaagcaatt ggtttagtaa ttggtacaat    8400
ctcaacaagt tgattctgga attcaggaaa gaagaagtaa taagaactgg ttcaatcttg    8460
tgtaggtcat tgggtaaatt agttttttgtt gtatcatcat acggatgtat agtcaagagc    8520
aacaaaagca aagagtgag cttcttcaca tacaatcaac tgttaacatg gaaagatgtg    8580
atgttaagta gattcaatgc aaatttctgt atatgggtaa gcaacagtct gaatgaaaat    8640
caagaagggt tagggttgag aagtaatctg caaggcatat taactaataa gctatatgaa    8700
actgtagatt atatgcttag tttgtgttgc aatgaaggtt tctcacttgt gaaagagttt    8760
gagggtttta ttatgagtga aatccttagg attactgaac atgctcaatt cagtactaga    8820
tttagaaata ctttattaaa tggattaact gatcaattga caaaattaaa aaataaaaac    8880
agactcagag ttcatggtac cgtgttagaa ataatgatt atccaatgta tgaagttgta    8940
cttaaattat taggagatac tttgagatgt attaaattat taatcaataa aaacttagag    9000
aatgctgctg aattatacta tatatttaga atattcggtc acccaatggt agatgaaaga    9060
gatgcaatgg atgctgtcaa attaaacaat gaaatcacaa aaatcctcag gttggagagc    9120
ttgacagaac taagagggc attcatatta aggattatca aaggatttgt agacaacaac    9180
aaaagatggc cgaaaattaa aaacttaaaa gtgcttagta aaagatggac tatgtacttc    9240
aaagcaaaaa gttaccctag tcaacttgaa ttaagtgaac aagattttt agagcttgct    9300 gcaatacagt ttgaacaaga gttttctgtt cctgaaaaaa ccaaccttga gatggtatta    9360
aatgataaag ctatatcacc tcctaaaaga ttaaatttggt ctgtgtaccc aaaaaattac    9420
ttacctgaga caataaaaaa tcgatatcta gaagagactt tcaatgcaag tgatagtctc    9480
aaaacaagaa gagtactaga gtactatttg aaagataata aattcgacca aaaagaactt    9540
aaaagttatg tggttaaaca agaatattta aatgataagg atcatattgt ctcgctaact    9600
ggaaaagaaa gagaattaag tgtaggtaga atgtttgcta tgcaaccagg aaaacagcga    9660
caaatacaaa tattggctga aaaattgtta gctgataata ttgtacccctt tttcccagaa    9720 actttaacaa gtatggtga tctagatctt cagagaataa tggaaatcaa atcgaacctt    9780
tcttctatta aaccagaag aaatgatagt tataataatt acattgcaag agcatccata    9840
gtaacagatt taagtaagtt caaccaagcc tttaggtatg aaactacagc gatctgtgcg    9900
gatgtagcag atgaactaca tggaacacaa agcctattct gttggttaca tcttatcgtt    9960
cctatgacta caatgatatg tgcctataga catgcaccac cagaaacaaa aggtgaatat   10020
gatatagata agatagaaga gcaaagtggt ttatatagat atcatatggg tggtattgaa   10080
ggatggtgtc aaaaactctg gacaatggaa gctatatctt tattagatgt tgtatctgta   10140
aagacacgat gtcaaatgac atctttatta aacggtgaca accaatcaat agatgtaagt   10200
aaaccagtta agttatctga gggtttagat gaagtgaaag cagattatag cttggctgta   10260
aaaatgctaa agaaataag agatgcatac agaaatatag gccataaact taagaagggg   10320
gaaacatata tatcaagaga tcttcagttt ataagtaagg tgattcaatc tgaaggagta   10380
atgcatccta ccctataaa aaagatctta agagtgggac catggataaa cacaatatta   10440
gatgacatta aaccagtgc agagtcaata gggagtctat gtcaggaatt agaatttagg   10500
ggggaaagca taatagttag tctgatatta aggaattttt ggctgtataa tttatacatg   10560
```

```
catgaatcaa agcaacaccc cctagcaggg aagcagttat tcaaacaact aaataaaaca   10620
ttaacatcag tgcagagatt ttttgaaatt aaaaaggaaa atgaagtagt agatctatgg   10680
atgaacatac caatgcagtt tggaggagga gatccagtag tcttctatag atctttctat   10740
agaaggaccc ctgattttt aactgaagca atcagtcatg tagatattct gttaaaaata    10800
tcagccaaca taagaaatga agcgaaaata agtttcttca aagccttact gtcaatagaa   10860
aaaaatgaac gtgctacact gacaacacta atgagagacc ctcaagctgt gggctcagag   10920
cgacaagcaa aagtaacaag tgatatcaat agaacagcag ttaccagcat cttaagtctt   10980
tctccaaatc aactttcag cgatagtgct atacactaca gtagaaatga agaagaggtc    11040
ggaatcattg ctgacaacat aacacctgtt tatcctcatg gactgagagt tttgtatgaa   11100
tcattacctt tcataaagc tgaaaaagtt gtaaatatga tatcaggaac aaaatccata    11160
accaacttat tacagagaac atctgctatt aatggtgaag atattgacag agctgtatcc   11220
atgatgctgg agaacctagg attattatct agaatattgt cagtagttgt tgatagtata   11280
gaaattccaa ccaaatctaa tggtaggctg atatgttgtc agatatctag aaccctaagg   11340
gagacatcat ggaataatat ggaaatagtt ggagtaacat cccctagcat cactacatgc   11400
atggatgtca tatatgcaac tagctctcat ttgaaaggga taatcattga aaagttcagc   11460
actgacagaa ctacaagagg tcaaagaggt ccaaagagcc cttgggtagg atcgagcacg   11520
caagagaaaa aattagttcc tgtttataac agacaaattc tttcaaaaca acaaagagaa   11580
cagctagaag caattggaaa aatgagatgg gtatataaag ggacaccagg tttaagacga   11640
ttactcaata agatttgtct tggaagttta ggcattagtt acaaatgtgt aaaacctta    11700 ttacctaggt ttatgagtgt aaatttccta cacaggttat ctgtcagtag tagacctatg   11760
gaattcccag catcagttcc agcttataga acaacaaatt accattttga cactagtcct   11820
attaatcaag cactaagtga agatttggg aatgaagata ttaatttggt cttccaaaat    11880
gcaatcagct gtggaattag cataatgagt gtagtagaac aattaactgg taggagtcca   11940
aaacagttag ttttaatacc ccaattagaa gaaatagaca ttatgccacc accagtgttt   12000
caagggaaat tcaattataa gctagtagat aagataactt ctgaccaaca tatcttcagt   12060
ccagacaaaa tagatatgtt aacactgggg aaaatgctca tgccaactat aaaaggtcag   12120
aaaacagatc agttcttgaa caagagagag aattatttcc atgggaacaa tcttattgag   12180
tctttgtcag cagcgttagc atgtcattgg tgtgggatat taacagagca atgtatagaa   12240
aataatattt tcaagaaaga ctggggtgac gggttcatat cggatcatgc ttttatggac   12300
ttcaaaatat tcctatgtgt ctttaaaact aaacttttat gtagttgggg atcccaaggg   12360
aaaaacatta aagatgaaga tatagtagat gaatcgatag ataaactgtt aaggattgat   12420
aatacttttt ggagaatgtt cagcaaggtt atgtttgaat caaaggttaa gaaaaggata   12480
atgttatatg atgtaaaatt tctatcatta gtaggttata tagggtttaa gaattggttt   12540
atagaacagt tgagatcagc tgagttgcat gaggtacctt ggattgtcaa tgccgaaggt   12600
gatctggttg agatcaagtc aattaaaatc tatttgcaac tgatagagca gagtttattt   12660
ttaagaataa ctgttttgaa ctatacagat atggcacatg ctctcacaag attaatcaga   12720
aagaagttga tgtgtgataa tgcactatta acttcaattc catcccaat ggttaactta    12780 actcaagtta ttgatcctac agaacaatta gcttatttcc ctaagataac atttgaaagg   12840
ctaaaaaatt atgacactag ttcaaattat gctaaaggaa agctaacaag gaattacatg   12900
```

| | | |
|---|---|---|
| atactgttgc catggcaaca tgttaataga tataactttg tctttagttc tactggatgt | 12960 |
| aaagttagtc taaaaacatg cattggaaaa cttatgaaag atctaaaccc taaagttctg | 13020 |
| tactttattg gagaaggggc aggaaattgg atggccagaa cagcatgtga atatcctgac | 13080 |
| atcaaatttg tatacagaag tttaaaagat gaccttgatc atcattatcc tttggaatac | 13140 |
| cagagagtga taggagaatt aagcaggata atagatagtg gtgaagggct ttcaatggaa | 13200 |
| acaacagatg caactcaaaa aactcattgg gatttgatac acagagtaag caaagatgct | 13260 |
| ttattaataa ctttatgtga tgcagaattt aaggacagag atgatttttt taagatggta | 13320 |
| attctatgga ggaaacatgt attatcatgc agaatttgca ctacctatgg gacagacctc | 13380 |
| tatttattcg caaagtatca tgctaaagac tgcaatataa aattaccttt ttttgtgaga | 13440 |
| tcagttgcca cctttattat gcaaggtagt aaactgtcag gctcggaatg ctacatactc | 13500 |
| ttaacactag gccaccacaa caatttacct tgtcatggag aaatacaaaa ttctaagatg | 13560 |
| aaaatagcag cgtgtaatga tttttatgct gcaaaaaaac ttgacaataa atcaattgaa | 13620 |
| gccaactgta aatcactttt atcagggcta agaataccga taataagaa ggaattaaat | 13680 |
| agacagagaa ggttattaac actacaaagc aaccattctt ctgtagcaac agttggaggt | 13740 |
| agcaaggtca tagagtctaa atggttaaca acaaggcaa acacaataat tgattggtta | 13800 |
| gaacatattt taaattctcc aaaaggtgaa ttaaattatg atttttttga agcattagaa | 13860 |
| aatacttacc ctaatatgat taaactaata gataatctag ggaatgcaga gattaaaaaa | 13920 |
| ctgatcaaag taactggata tatgcttgta agtaaaaaat gaaaaatgat aaaaatgata | 13980 |
| aaataggtga caacttcata ctattccaaa gtaatcattt gattatgcaa ttatgtaata | 14040 |
| gttaattaaa aactaaaaat caaaagttaa aaactaataa ctgtcattaa gtttattaaa | 14100 |
| aataagaaat tataattgga tgtatacggt ttttttgccg t | 14141 |

<210> SEQ ID NO 5
<211> LENGTH: 13392
<212> TYPE: DNA
<213> ORGANISM: Artificial Sequence
<220> FEATURE:
<223> OTHER INFORMATION: GFP encoding gene is inserted betwwen
      nucleotides 40 and 784

<400> SEQUENCE: 5

| | | |
|---|---|---|
| gcgaaaaaaa cgcgtataaa ttagattaca aaaaatatg ggacaagtga aaatggtgag | 60 |
| caagggcgag gagctgttca ccggggtggt gcccatcctg gtcgagctgg acggcgacgt | 120 |
| aaacggccac aagttcagcg tgtccggcga gggcgagggc gatgccacct acggcaagct | 180 |
| gaccctgaag ttcatctgca ccaccggcaa gctgcccgtg ccctggccca cctcgtgac | 240 |
| caccctgacc tacggcgtgc agtgcttcag ccgctacccc gaccacatga agcagcacga | 300 |
| cttcttcaag tccgccatgc ccgaaggcta cgtccaggag cgcaccatct tcttcaagga | 360 |
| cgacggcaac tacaagaccc gcgccgaggt gaagttcgag ggcgacaccc tggtgaaccg | 420 |
| catcgagctg aagggcatcg acttcaagga ggacggcaac atcctggggc acaagctgga | 480 |
| gtacaactac aacagccaca acgtctatat catggccgac aagcagaaga acggcatcaa | 540 |
| ggtgaacttc aagatccgcc acaacatcga ggacggcagc gtgcagctcg ccgaccacta | 600 |
| ccagcagaac acccccatcg gcgacggccc cgtgctgctg cccgacaacc actacctgag | 660 |
| cacccagtcc gccctgagca agacccccaa cgagaagcgc gatcacatgg tcctgctgga | 720 |
| gttcgtgacc gccgccggga tcactctcgg catggacgag ctgtacaagt aagttaatta | 780 |

```
aaaagtggga caagtgaaaa tgtctcttca agggattcac ctgagtgatc tatcatacaa    840
gcatgctata ttaaaagagt ctcagtacac aataaaaaga gatgtgggta caacaactgc    900
agtgacaccc tcatcattgc aacaagaaat aacgctgttg tgtggagaaa ttctgtatgc    960
taaacatgct gattacaaat atgctgcaga aataggaata caatatatta gcacagcttt   1020
aggatcagag agagtgcagc agattctgag gaactcaggc agtgaagtcc aagtggtctt   1080
aaccagaacg tactctctgg ggaaagttaa aaacaataaa ggagaagatt tacagatgtt   1140
agacatacac ggggtagaga agagctgggt agaagagata gacaaagaag caaggaaaac   1200
aatggcaacc ttgcttaagg aatcatcagg taatatccca caaaatcaga ggccctcagc   1260
accagacaca cccataatct tattatgtgt aggtgcatta atatttacta agctagcatc   1320
aaccatagaa gtgggactag agaccacagt cagaagggct aaccgtgtac taagtgatgc   1380
actcaagaga taccctagaa tggacatccc aaaaattgcc agatccttct atgacttatt   1440
tgaacaaaaa gtgtatcaca gaagtttgtt cattgagtat ggcaaagcat taggctcatc   1500
atctacaggc agcaaagcag aaagtctatt tgttaatata ttcatgcaag cttatggagc   1560
cggtcaaaca atgctaaggt gggggtcat tgccaggtca tccaacaata taatgttagg   1620
acatgtatct gtccaagctg agttaaaaca ggtcacagaa gtctatgact tggtgcgaga   1680
aatgggccct gaatctggac ttctacattt aaggcaaagc ccaaaagctg gactgttatc   1740
actagccaac tgtcccaact tgcaagtgt tgttctcgga aatgcctcag gcttaggcat   1800
aatcggtatg tatcgtggga gagtaccaaa cacagaatta ttttcagcag cagaaagtta   1860
tgccaaaagt ttgaaagaga gcaataaaat caatttctct tcattaggac ttacagatga   1920
agagaaagag gctgcagaac atttcttaaa tgtgagtgac gacagtcaaa atgattatga   1980
gtaattaaaa aagtgggaca agtcaaaatg tctttccctg aaggaaaaga tattcttttc   2040
atgggtaatg aagcagcaaa attagcagaa gctttccaga aatcattaag gaaaccaagt   2100
cataaaagat ctcaatctat tataggagaa aaagtgaaca ctgtatcaga aacattggaa   2160
ttacctacta tcagtagacc tgcaaaacca accatactgt cagaaccaaa gttagcatgg   2220
actgataaag gtggggcaat caaaactgaa ataaagcaag caatcaaagt catggatcct   2280
attgaggaag aagagtctac tgagaagaag gtgctgccct ccagtgatgg gaaaacccct   2340
gcagaaaaga aactgaaacc atcaactaac accaaaaaga aagtttcgtt tacaccaaat   2400
gaaccaggaa aatatacaaa gttggaaaaa gatgctctag atttgctctc agataatgaa   2460
gaagaagatg cagaatcttc aatcttaacc tttgaagaaa gagatacttc atcgttaagc   2520
attgaggcca gattggaatc aatagaggag aaattaagca tgatattagg ctattaagaa   2580
acactcaaca ttgctacagc aggacccaca gcagcaagag atgggatcag agatgcaatg   2640
attggcgtaa gagaggaatt aatagcagac ataataaagg aagccaaagg gaaagcagca   2700
gaaatgatgg aagaggaaat gagtcaacga tcaaaaatag gaaacggtag tgtaaaacta   2760
acagagaaag caaagagct taacaaaatt gttgaagatg aaagcacaag tggagaatct   2820
gaagaagaag aagaaccaaa agacatacaa gacaatagtc aagaagatga catttaccag   2880
ttaattatgt agtttaataa aaataaacaa tgggacaagt aaaaatggag tcctacctag   2940
tagacactta tcaaggcatt ccttacacag cagctgttca agttgatcta atagaaaagg   3000
acctgttacc tgcaagccta acaatatggt tcccttttgtt tcaggccaac acaccaccag   3060
cagtgctgct cgatcagttg aaaacccctaa caataaccac tctgtatgct gcatcacaaa   3120
atggtccaat actcaaagtg aatgcatcag cccaaggtgc agcaatgtct gtacttccca   3180
```

```
aaaaatttga agtcaatgcg actgtagcac tcgatgaata tagcaaattg gaatttgaca    3240
aactcacagt ctgtgaagta aaaacagttt acttaacaac catgaaacca tacgggatgg    3300
tatcaaaatt tgtgagctca gccaaatcag ttggcaaaaa aacacatgat ctaatcgcac    3360
tgtgtgattt tatggatcta gaaaagaaca cacctgttac aataccagca ttcatcaaat    3420
cagtttcaat caaagagagt gagtcagcta ctgttgaagc tgctataagc agtgaagcag    3480
accaagctct aacacaggcc aaaattgcac cttatgcggg attgattatg atcatgacta    3540
tgaacaatcc caaaggcata ttcaaaaagc ttggagctgg gactcaagtt atagtagaac    3600
taggagcata tgtccaggct gaaagcataa gtaaaatatg caagacttgg agccatcaag    3660
ggacaagata tgtgttgaag tccagataac agccaagcac cttggccaag agctactaac    3720
tctatctcat agattataaa gtcaccattc tagttatata aaaatcaagt tagaacaaga    3780
attaaatcaa tcaagaatgg gacaaataaa aatgtcttgg aaagtggtga tcattttttc    3840
attgttaata cacctcaac acggtcttaa agagagctat ttagaagagt catgtagcac     3900
tataactgaa ggatatctca gtgttctgag gacaggttgg tataccaacg ttttacact     3960 ggaggtaggt gatgtagaga accttacatg tgctgatgga cctagcttaa taaaaacaga    4020
attagacctg accaaaagtg cactaagaga actcagaaca gtttctgctg atcaactggc    4080
aagagaggag caaattgaga atcccagaca atctagattt gttctaggag caatagcact    4140
cggtgttgca acagcagctg cagttacagc aggtgttgca attgccaaaa ccatccggct    4200
tgaaagtgaa gtaacagcaa ttaagaatgc cctcaaaaag accatgaag cagtatctac     4260 attggggaat ggagttcgag tgttggcaac tgcagtgagg gagctggaag attttgtgag    4320
caagaatcta acacgtgcaa tcaacaaaaa caagtgcgac attgctgacc tgaaaatggc    4380
cgttagcttc agtcaattca acagaaggtt tctaaatgtt gtgcggcaat ttcagacaa     4440 tgctggaata acaccagcaa tatccttgga cttaatgaca gatgctgaac tagccagagc    4500
tgtttccaac atgccaacat ctgcaggaca aataaaactg atgttggaga accgtgcaat    4560
ggtaagaaga aaggggttcg gaatcctgat aggagtttac ggaagctccg taatttacat    4620
ggtgcaactg ccaatctttg gagttataga cacgccttgc tggatagtaa aagcggcccc    4680
ttcttgctca gaaaaaaagg gaaactatgc ttgcctttta agagaagatc aaggatggta    4740
ttgtcagaat gcagggtcaa ctgtttacta cccaaatgaa aaagactgcg aaacaagagg    4800
agaccatgtc ttttgcgaca cagcagcagg aatcaatgtt gctgagcagt caaaggagtg    4860
caacatcaac atatccacta ctaattaccc atgcaaagtt agcacaggaa gacacctat     4920 cagtatggtt gcactgtctc ctcttgggc tttggttgct tgctacaagg gagtgagctg     4980
ttccattggc agcaacagag tagggatcat caagcaactg aacaaggct gctcttatat     5040 aaccaaccaa gacgcagaca cagtgacaat agacaacact gtataccagc taagcaaagt    5100
tgagggcgaa cagcatgtta taaaggaag gccagtgtca agcagctttg atccagtcaa    5160
atttcctgaa gatcaattca atgttgcact tgaccaagtt ttcgaaagca ttgagaacag    5220
tcaggccttg gtggatcaat caacagaat cctaagcagt gcagagaaag gaaacactgg    5280
cttcatcatt gtaataattc taattgctgt ccttggctct accatgatcc tagtgagtgt    5340
ttttatcata ataaagaaaa caagaaacc cacaggagca cctccagagc tgagtggtgt    5400
cacaaacaat ggcttcatac cacataatta gttaattaaa aataaagtaa attaaattaa    5460
aataaaataa aattaaaatt aaaataaaat aaaaataaaa atttgggaca aatcataatg    5520
```

```
tctcgcaagg ctccatgcaa atatgaagtg cggggcaaat gcaatagagg aagtgagtgc    5580
aagtttaacc acaattactg gagttggcca gatagatact tactaataag atcaaattat    5640
ttattaaatc aacttttaag gaacactgat agagctgatg gcttatcaat aatatcagga    5700
gcaggcagag aagataggac acaagatttt gtcctaggtt ccaccaatgt ggttcaaggt    5760
tatattgatg ataaccaaag cataacaaaa gctgcagcct gttacagtct acataatata    5820
atcaaacaac tacaagaagt tgaagttagg caggctagag ataacaaacc atctgacagc    5880
aaacatgtgg cacttcacaa cttagtccta tcttatatgg agatgagcaa aattcctgca    5940
tctttaatca acaatctcaa aagactgccg agagagaaac tgaaaaaatt agcaaagctt    6000
ataattgact tatcagcagg tgctgaaaat gactcttcat atgccttgca agacagtgaa    6060
agcactaatc aagtgcagtg agcatggtcc tgttttcatt actatagagg ttgattacat    6120
gatatggact cataaggact taaaagaagc tttatctaat gggatagtga agtctcatac    6180
taacatttac aattgttatt tagaaaacat agaaattata tatgtcaagg cttacttaag    6240
ttagtaaaaa cacatcagag tgggacaagt agttatggag gtgaaagtgg agaacattcg    6300
aacaatagat atgctcaaag caagagtgaa aaatcgtgtg gcacgcagca aatgctttaa    6360
aaatgcctct ttgatcctaa taggaataac tacattgagt atagccctca atatctatct    6420
aatcataaac tatacaatgc aagaaaacac atccgaatca gaacatcaca ccagctcatc    6480
acccatggaa tccagcaggg aaactccaac agtccctatg acaactcag acaccaatcc     6540 aggctcacag tatccaactc aacagtccac agaaggctcc acactctact tgcagcctc     6600 agcaagctca ccagagacag aaccaacatc aacaccagac acaacaagcc gcccgcccctt   6660 cgtcgacaca cacacaacac taccaagtgc aagcagaaca aggacaagtc cggcagtcca    6720
cacaaaaaac aatccaagga caagcccag aacacattcc ccaccatggg caatgacaag      6780
gacggtccgt ggaaccacca ctctccgcac aagcagcaca agaaaaagac cgtccacagc    6840
atcagtccaa cctgacagca gcgcaacaac ccacaaacac gaagaagcaa gcccagtgag    6900
cccgcaaaca tctgcgagca cagcaagacc acaaaggaag ggcatggagg ccagcacatc    6960
aacaacatac aaccaaacta gttaacaaaa aatacaaaat aactctaaga taaaccatat    7020
agacaccaac aattgagaag ccaaaaggca attcacaatc tctccaaaaa ggcaacaaca    7080
ccatattagc tccgcttaaa tctccctgga aaaaacactc gcccatatac caactatacc    7140
acaaccatcc caagaaaaaa agctgggtaa acaacaccc aagagacaaa taacaatgga      7200
tcctcttaat gaatccactg ttaatgtcta tcttcccgac tcatatctta aaggagtgat    7260
ttcttttagt gagactaatg caattggttc atgtctctta aaaagacctt acctaaaaaa    7320
tgacaacact gcaaaagttg ccatagagaa tcctgttatc gagcatgtta gactcaaaaa    7380
tgcaatcaat tctaagatga aaatatcaga ttacaggata gtagagccag taaacatgca    7440
acatgaaatt atgaagaatg tacacagttg tgagctcaca ttattaaaac agttttttaac    7500 aaggagtaaa aatattagca ctcttaaatt aaatatgata tgtgattggc tgcagttaaa    7560
gtctacatca gatgatacct caatcttaag ttttatagat gtagaattta tacctagctg    7620
ggtaagcaat tggtttagta attggtacaa tctcaacaag ttgattctgg aattcaggaa    7680
agaagaagta ataagaactg gttcaatctt gtgtaggtca ttgggtaaat tagttttttgt   7740 tgtatcatca tacggatgta tagtcaagag caacaaaagc aaaagagtga gcttcttcac    7800
atacaatcaa ctgttaacat ggaaagatgt gatgttaagt agattcaatg caaatttctg    7860
tatatgggta agcaacagtc tgaatgaaaa tcaagaaggg ttagggttga gaagtaatct    7920
```

```
gcaaggcata ttaactaata agctatatga aactgtagat tatatgctta gtttgtgttg   7980
caatgaaggt ttctcacttg tgaaagagtt tgagggtttt attatgagtg aaatccttag   8040
gattactgaa catgctcaat tcagtactag atttagaaat actttattaa atggattaac   8100
tgatcaattg acaaaattaa aaaataaaaa cagactcaga gttcatggta ccgtgttaga   8160
aaataatgat tatccaatgt atgaagttgt acttaaatta ttaggagata ctttgagatg   8220
tattaaatta ttaatcaata aaaacttaga gaatgctgct gaattatact atatatttag   8280
aatattcggt cacccaatgg tagatgaaag agatgcaatg gatgctgtca aattaaacaa   8340
tgaaatcaca aaaatcctca ggttggagag cttgacagaa ctaagagggg cattcatatt   8400
aaggattatc aaaggatttg tagacaacaa caaagatgg ccgaaaatta aaaacttaaa    8460
agtgcttagt aaaagatgga ctatgtactt caaagcaaaa agttaccta gtcaacttga    8520 attaagtgaa caagattttt tagagcttgc tgcaatacag tttgaacaag agttttctgt   8580
tcctgaaaaa accaaccttg agatggtatt aaatgataaa gctatatcac ctcctaaaag  8640
attaatttgg tctgtgtacc caaaaaatta cttacctgag acaataaaaa atcgatatct   8700
agaagagact ttcaatgcaa gtgatagtct caaaacaaga agagtactag agtactattt   8760
gaaagataat aaaattcgacc aaaaagaact taaaagttat gtggttaaac aagaatattt  8820
aaatgataag gatcatattg tctcgctaac tggaaaagaa agagaattaa gtgtaggtag   8880
aatgtttgct atgcaaccag gaaaacagcg acaaatacaa atattggctg aaaaattgtt   8940
agctgataat attgtaccct ttttcccaga aactttaaca aagtatggtg atctagatct   9000
tcagagaata atggaaatca aatcagaact ttcttctatt aaaaccagaa gaaatgatag   9060
ttataataat tacattgcaa gagcatccat agtaacagat ttaagtaagt tcaaccaagc   9120
ctttaggtat gaaactacag cgatctgtgc ggatgtagca gatgaactac atggaacaca   9180
aagcctattc tgttggttac atcttatcgt tcctatgact acaatgatat gtgcctatag   9240
acatgcacca ccagaaacaa aaggtgaata tgatatagat aagatagaag agcaaagtgg   9300
tttatataga tatcatatgg gtggtattga aggatggtgt caaaaactct ggacaatgga   9360
agctatatct ttattagatg ttgtatctgt aaagacacga tgtcaaatga catctttatt   9420
aaacggtgac aaccaatcaa tagatgtaag taaaccagtt aagttatctg agggtttaga   9480
tgaagtgaaa gcagattata gcttggctgt aaaaaatgcta aaagaaataa gagatgcata   9540
cagaaatata ggccataaac ttaaagaagg ggaaacatat atatcaagag atcttcagtt   9600
tataagtaag gtgattcaat ctgaaggagt aatgcatcct accctataa aaagatctt    9660 aagagtggga ccatggataa acacaatatt agatgacatt aaaaccagtg cagagtcaat   9720
agggagtcta tgtcaggaat tagaatttag gggggaaagc ataatagtta gtctgatatt   9780
aaggaatttt tggctgtata atttatacat gcatgaatca agcaacacc ccctagcagg    9840 gaagcagtta ttcaaacaac taaataaaac attaacatca gtgcagagat tttttgaaat   9900
taaaaaggaa aatgaagtag tagatctatg gatgaacata ccaatgcagt ttggaggagg   9960
agatccagta gtcttctata gatctttcta tagaaggacc cctgattttt taactgaagc  10020
aatcagtcat gtagatattc tgttaaaaat atcagccaac ataagaaatg aagcgaaaat  10080
aagtttcttc aaagccttac tgtcaataga aaaaaatgaa cgtgctacac tgacaacact  10140
aatgagagac cctcaagctg tgggctcaga gcgacaagca aaagtaacaa gtgatatcaa  10200
tagaacagca gttaccagca tcttaagtct ttctccaaat caacttttca gcgatagtgc  10260
```

```
tatacactac agtagaaatg aagaagaggt cggaatcatt gctgacaaca taacacctgt    10320
ttatcctcat ggactgagag ttttgtatga atcattacct tttcataaag ctgaaaaagt    10380
tgtaaatatg atatcaggaa caaaatccat aaccaactta ttacagagaa catctgctat    10440
taatggtgaa gatattgaca gagctgtatc catgatgctg gagaacctag gattattatc    10500
tagaatattg tcagtagttg ttgatagtat agaaattcca accaaatcta atggtaggct    10560
gatatgttgt cagatatcta gaaccctaag ggagacatca tggaataata tggaaatagt    10620
tggagtaaca tccccctagca tcactacatg catggatgtc atatatgcaa ctagctctca    10680
tttgaaaggg ataatcattg aaaagttcag cactgacaga actacaagag gtcaaagagg    10740
tccaaagagc ccttgggtag gatcgagcac gcaagagaaa aaattagttc ctgtttataa    10800
cagacaaatt ctttcaaaac aacaaagaga acagctagaa gcaattggaa aaatgagatg    10860
ggtatataaa gggacaccag gtttaagacg attactcaat aagatttgtc ttggaagttt    10920
aggcattagt tacaaatgtg taaaaccttt attacctagg tttatgagtg taaatttcct    10980
acacaggtta tctgtcagta gtagacctat ggaattccca gcatcagttc cagcttatag    11040
aacaacaaat taccattttg acactagtcc tattaatcaa gcactaagtg aaagatttgg    11100
gaatgaagat attaatttgg tcttccaaaa tgcaatcagc tgtggaatta gcataatgag    11160
tgtagtagaa caattaactg gtaggagtcc aaaacagtta gttttaatac cccaattaga    11220
agaaatagac attatgccac caccagtgtt tcaagggaaa ttcaattata gctagtaga    11280 taagataact tctgaccaac atatcttcag tccagacaaa atagatatgt taacactggg    11340
gaaaatgctc atgccaacta taaaggtca gaaaacagat cagttcttga caagagaga    11400 gaattatttc catgggaaca atcttattga gtctttgtca gcagcgttag catgtcattg    11460
gtgtgggata ttaacagagc aatgtataga aaataatatt ttcaagaaag actggggtga    11520
cgggttcata tcggatcatg cttttatgga cttcaaaata ttcctatgtg tcttaaaac    11580 taaacttta tgtagttggg gatcccaagg gaaaaacatt aaagatgaag atatagtaga    11640
tgaatcgata gataaactgt taaggattga taatactttt tggagaatgt tcagcaaggt    11700
tatgtttgaa tcaaaggtta agaaaaggat aatgttatat gatgtaaaat ttctatcatt    11760
agtaggttat ataggggttta agaattggtt tatagaacag ttgagatcag ctgagttgca    11820
tgaggtacct tggattgtca atgccgaagg tgatctggtt gagatcaagt caattaaaat    11880
ctatttgcaa ctgatagagc agagtttatt tttaagaata actgttttga actatacaga    11940
tatggcacat gctctcacaa gattaatcag aaagaagttg atgtgtgata atgcactatt    12000
aacttcaatt ccatccccaa tggttaactt aactcaagtt attgatccta cagaacaatt    12060
agcttatttc cctaagataa catttgaaag gctaaaaaat tatgcacacta gttcaaatta    12120 tgctaaagga aagctaacaa ggaattacat gatactgttg ccatggcaac atgttaatag    12180
atataacttt gtctttagtt ctactggatg taaagttagt ctaaaaacat gcattggaaa    12240
acttatgaaa gatctaaacc ctaaagttct gtactttatt ggagaagggg caggaaattg    12300
gatggccaga acagcatgtg aatatcctga catcaaattt gtatacagaa gtttaaaaga    12360
tgaccttgat catcattatc ctttggaata ccagagagtg ataggagaat taagcaggat    12420
aatagatagt ggtgaagggc tttcaatgga aacaacagat gcaactcaaa aaactcattg    12480
ggatttgata cacagagtaa gcaaagatgc tttattaata actttatgtg atgcagaatt    12540
taaggacaga gatgattttt ttaagatggt aattctatgg aggaaacatg tattatcatg    12600
cagaatttgc actacctatg ggacagacct ctatttattc gcaaagtatc atgctaaaga    12660
```

-continued

```
ctgcaatata aaattacctt tttttgtgag atcagttgcc acctttatta tgcaaggtag    12720
taaactgtca ggctcggaat gctacatact cttaacacta ggccaccaca acaatttacc    12780
ttgtcatgga gaaatacaaa attctaagat gaaaatagca gcgtgtaatg atttttatgc    12840
tgcaaaaaaa cttgacaata aatcaattga agccaactgt aaatcacttt tatcagggct    12900
aagaataccg ataaataaga aggaattaaa tagacagaga aggttattaa cactacaaag    12960
caaccattct tctgtagcaa cagttggagg tagcaaggtc atagagtcta aatggttaac    13020
aaacaaggca aacacaataa ttgattggtt agaacatatt ttaaattctc caaaggtga     13080 attaaattat gattttttg aagcattaga aaatacttac cctaatatga ttaaactaat     13140
agataatcta gggaatgcag agattaaaaa actgatcaaa gtaactggat atatgcttgt    13200
aagtaaaaaa tgaaaaatga taaaaatgat aaaataggtg acaacttcat actattccaa    13260
agtaatcatt tgattatgca attatgtaat agttaattaa aaactaaaaa tcaaaagtta    13320
aaaactaata actgtcatta agtttattaa aaataagaaa ttataattgg atgtatacgg    13380 ttttttgcc gt                                                         13392
```

<210> SEQ ID NO 6
<211> LENGTH: 13220
<212> TYPE: DNA
<213> ORGANISM: Artificial Sequence
<220> FEATURE:
<223> OTHER INFORMATION: GFP encoding gene is inserted between
      nucleotides 40 and 784

<400> SEQUENCE: 6

```
gcgaaaaaaa cgcgtataaa ttagattaca aaaaatatg ggacaagtga aaatggtgag      60
caagggcgag gagctgttca ccggggtggt gcccatcctg gtcgagctgg acggcgacgt     120
aaacggccac aagttcagcg tgtccggcga gggcgagggc gatgccacct acggcaagct    180
gaccctgaag ttcatctgca ccaccggcaa gctgcccgtg ccctggccca ccctcgtgac    240
caccctgacc tacggcgtgc agtgcttcag ccgctacccc gaccacatga agcagcacga    300
cttcttcaag tccgccatgc ccgaaggcta cgtccaggag cgcaccatct tcttcaagga    360
cgacggcaac tacaagaccc gcgccgaggt gaagttcgag ggcgacaccc tggtgaaccg    420
catcgagctg aagggcatcg acttcaagga ggacggcaac atcctggggc acaagctgga    480
gtacaactac aacagccaca acgtctatat catggccgac aagcagaaga acggcatcaa    540
ggtgaacttc aagatccgcc acaacatcga ggacggcagc gtgcagctcg ccgaccacta    600
ccagcagaac acccccatcg gcgacggccc cgtgctgctg cccgacaacc actacctgag    660
cacccagtcc gccctgagca agacccccaa cgagaagcgc gatcacatgg tcctgctgga    720
gttcgtgacc gccgccggga tcactctcgg catggacgag ctgtacaagt aagttaatta    780
aaaagtggga caagtgaaaa tgtctcttca agggattcac ctgagtgatc tatcatacaa    840
gcatgctata ttaaaagagt ctcagtacac aataaaaaga gatgtgggta caacaactgc    900
agtgacaccc tcatcattgc aacaagaaat aacgctgttg tgtggagaaa ttctgtatgc    960
taaacatgct gattacaaat atgctgcaga ataggaata caatatatta gcacagcttt    1020
aggatcagag agagtgcagc agattctgag gaactcaggc agtgaagtcc aagtggtctt    1080
aaccagaacg tactctctgg ggaaagttaa aacaataaa ggagaagatt tacagatgtt     1140
agacatacac ggggtagaga agagctgggt agaagagata gacaaagaag caaggaaaac    1200
aatggcaacc ttgcttaagg aatcatcagg taatatccca caaaatcaga ggccctcagc    1260
```

```
accagacaca cccataatct tattatgtgt aggtgcatta atatttacta agctagcatc    1320
aaccatagaa gtgggactag agaccacagt cagaagggct aaccgtgtac taagtgatgc    1380
actcaagaga taccctagaa tggacatccc aaaaattgcc agatccttct atgacttatt    1440
tgaacaaaaa gtgtatcaca gaagtttgtt cattgagtat ggcaaagcat taggctcatc    1500
atctacaggc agcaaagcag aaagtctatt tgttaatata ttcatgcaag cttatggagc    1560
cggtcaaaca atgctaaggt gggggggtcat tgccaggtca tccaacaata taatgttagg    1620
acatgtatct gtccaagctg agttaaaaca ggtcacagaa gtctatgact tggtgcgaga    1680
aatgggccct gaatctggac ttctacattt aaggcaaagc ccaaaagctg gactgttatc    1740
actagccaac tgtcccaact ttgcaagtgt tgttctcgga aatgcctcag gcttaggcat    1800
aatcggtatg tatcgtggga gagtaccaaa cacagaatta ttttcagcag cagaaagtta    1860
tgccaaaagt ttgaaagaga gcaataaaat caatttctct tcattaggac ttacagatga    1920
agagaaagag gctgcagaac atttcttaaa tgtgagtgac gacagtcaaa atgattatga    1980
gtaattaaaa aagtgggaca agtcaaaatg tctttccctg aaggaaaaga tattcttttc    2040
atgggtaatg aagcagcaaa attagcagaa gctttccaga aatcattaag gaaaccaagt    2100
cataaaagat ctcaatctat tataggagaa aaagtgaaca ctgtatcaga aacattggaa    2160
ttacctacta tcagtagacc tgcaaaacca accatactgt cagaaccaaa gttagcatgg    2220
actgataaag gtggggcaat caaaactgaa ataaagcaag caatcaaagt catggatcct    2280
attgaggaag aagagtctac tgagaagaag gtgctgccct ccagtgatgg gaaaacccct    2340
gcagaaaaga aactgaaacc atcaactaac accaaaaaga agtttcgtt tacaccaaat    2400 gaaccaggaa aatatacaaa gttggaaaaa gatgctctag atttgctctc agataatgaa    2460
gaagaagatg cagaatcttc aatcttaacc tttgaagaaa gagatacttc atcgttaagc    2520
attgaggcca gattggaatc aatagaggag aaattaagca tgatattagg gctattaaga    2580
acactcaaca ttgctacagc aggacccaca gcagcaagag atgggatcag agatgcaatg    2640
attggcgtaa gagaggaatt aatagcagac ataataaagg aagccaaagg gaaagcagca    2700
gaaatgatgg aagaggaaat gagtcaacga tcaaaaatag gaaacggtag tgtaaaacta    2760
acagagaaag caaagagct taacaaaatt gttgaagatg aaagcacaag tggagaatct    2820
gaagaagaag aagaaccaaa agacatacaa gacaatagtc aagaagatga catttaccag    2880
ttaattatgt agtttaataa aaataaacaa tgggacaagt aaaaatggag tcctacctag    2940
tagacactta tcaaggcatt ccttacacag cagctgttca agttgatcta atagaaaagg    3000
acctgttacc tgcaagccta acaatatggt tccctttgtt tcaggccaac acaccaccag    3060
cagtgctgct cgatcagttg aaaaccctaa caataaccac tctgtatgct gcatcacaaa    3120
atggtccaat actcaaagtg aatgcatcag cccaaggtgc agcaatgtct gtacttccca    3180
aaaaatttga agtcaatgcg actgtagcac tcgatgaata tagcaaattg gaatttgaca    3240
aactcacagt ctgtgaagta aaaacagttt acttaacaac catgaaacca tacgggatgg    3300
tatcaaaatt tgtgagctca gccaaatcag ttggcaaaaa aacacatgat ctaatcgcac    3360
tgtgtgattt tatggatcta gaaaagaaca cacctgttac aataccagca ttcatcaaat    3420
cagtttcaat caaagagagt gagtcagcta ctgttgaagc tgctataagc agtgaagcag    3480
accaagctct aacacaggcc aaaattgcac cttatgcggg attgattatg atcatgacta    3540
tgaacaatcc caaaggcata ttcaaaaagc ttggagctgg gactcaagtt atagtagaac    3600
```

```
taggagcata tgtccaggct gaaagcataa gtaaaatatg caagacttgg agccatcaag    3660
ggacaagata tgtgttgaag tccagataac agccaagcac cttggccaag agctactaac    3720
tctatctcat agattataaa gtcaccattc tagttatata aaatcaagt  tagaacaaga    3780 attaaatcaa tcaagaatgg gacaaataaa aatgtcttgg aaagtggtga tcattttttc    3840
attgttaata acacctcaac acggtcttaa agagagctat ttagaagagt catgtagcac    3900
tataactgaa ggatatctca gtgttctgag gacaggttgg tataccaacg ttttttacact   3960 ggaggtaggt gatgtagaga accttacatg tgctgatgga cctagcttaa taaaaacaga    4020
attagacctg accaaaagtg cactaagaga actcagaaca gtttctgctg atcaactggc    4080
aagagaggag caaattgaga atcccagaca atctagattt gttctaggag caatagcact    4140
cggtgttgca acagcagctg cagttacagc aggtgttgca attgccaaaa ccatccggct    4200
tgaaagtgaa gtaacagcaa ttaagaatgc cctcaaaaag accaatgaag cagtatctac    4260
attggggaat ggagttcgag tgttggcaac tgcagtgagg gagctggaag attttgtgag    4320
caagaatcta acacgtgcaa tcaacaaaaa caagtgcgac attgctgacc tgaaaatggc    4380
cgttagcttc agtcaattca acagaaggtt tctaaatgtt gtgcggcaat tttcagacaa    4440
tgctggaata acaccagcaa tatccttgga cttaatgaca gatgctgaac tagccagagc    4500
tgtttccaac atgccaacat ctgcaggaca aataaaactg atgttggaga accgtgcaat    4560
ggtaagaaga aaggggttcg gaatcctgat aggagtttac ggaagctccg taatttacat    4620
ggtgcaactg ccaatctttg gagttataga cacgccttgc tggatagtaa agcggcccc    4680 ttcttgctca gaaaaaaagg gaaactatgc ttgcctttta agagaagatc aaggatggta    4740
ttgtcagaat gcagggtcaa ctgtttacta cccaaatgaa aaagactgcg aaacaagagg    4800
agaccatgtc ttttgcgaca cagcagcagg aatcaatgtt gctgagcagt caaggagtg    4860 caacatcaac atatccacta ctaattaccc atgcaaagtt agcacaggaa gacaccctat    4920
cagtatggtt gcactgtctc ctcttgggc  tttggttgct tgctacaagg gagtgagctg    4980
ttccattggc agcaacagag tagggatcat caagcaactg aacaaaggct gctctttatat   5040 aaccaaccaa gacgcagaca cagtgacaat agacaacact gtataccagc taagcaaagt    5100
tgagggcgaa cagcatgtta taaaaggaag gccagtgtca agcagctttg atccagtcaa    5160
atttcctgaa gatcaattca atgttgcact tgaccaagtt ttcgaaagca ttgagaacag    5220
tcaggccttg gtggatcaat caaacagaat cctaagcagt gcagagaaag gaaacactgg    5280
cttcatcatt gtaataattc taattgctgt ccttggctct accatgatcc tagtgagtgt    5340
ttttatcata ataaagaaaa caagaaacc  cacaggagca cctccagagc tgagtggtgt    5400
cacaaacaat ggcttcatac cacataatta gttaattaaa aataaagtaa attaaattaa    5460
aataaaataa aattaaaatt aaaataaaat aaaaataaaa atttgggaca atcataatg    5520 tctcgcaagg ctccatgcaa atatgaagtg cggggcaaat gcaatagagg aagtgagtgc    5580
aagtttaacc acaattactg gagttggcca gatagatact tactaataag atcaaattat    5640
ttattaaatc aacttttaag gaacactgat agagctgatg gcttatcaat aatatcagga    5700
gcaggcagag aagataggac acaagatttt gtcctaggtt ccaccaatgt ggttcaaggt    5760
tatattgatg ataaccaaag cataacaaaa gctgcagcct gttacagtct acataatata    5820
atcaaacaac tacaagaagt tgaagttagg caggctagag ataacaaacc atctgacagc    5880
aaacatgtgg cacttcacaa cttagtccta tcttatatgg agatgagcaa aattcctgca    5940 tcttttaatca acaatctcaa aagactgccg agagagaaac tgaaaaaatt agcaaagctt    6000
```

```
ataattgact tatcagcagg tgctgaaaat gactcttcat atgccttgca agacagtgaa    6060
agcactaatc aagtgcagtg agcatggtcc tgttttcatt actatagagg ttgattacat    6120
gatatggact cataaggact taaaagaagc tttatctaat gggatagtga agtctcatac    6180
taacatttac aattgttatt tagaaaacat agaaattata tatgtcaagg cttacttaag    6240
ttagtaaaaa cacatcagag tgggataaat gacaatgata acattagatg tcattaaaag    6300
tgatgggtct tcaaaaacat gtactcacct caaaaaatta attaaagacc actctggtaa    6360
agtgcttatt gtacttaagt taatattagc tttactaaca tttctcacag tgacaatcac    6420
catcaattat ataaaagtag aaaacaatct gcaaatatgt cagtcaaaaa ctgaatcaga    6480
caaaaaggac tcatcatcaa ataccacatc agtcacaacc aagactactc taaatcatga    6540
tataacacag tattttaaaa gtttgattca aaggtataca aactctgcaa taaacagaga    6600
cacatgctgg aaaataagca gaaatcaatg cacaaacata acaacataca aattttatg    6660 ttttaaatct gaagaaacaa aaaccaacaa ttgtgataaa ctgacagatt tatgcagaaa    6720
caaaccaaaa ccagctgttg aagtgtatca catagtagaa tgccattgta tatacacagt    6780
taaatggaag tgctatcatt acccaataga tgaaacccaa tcctaaataa cactagatta    6840
ggatccatcc aagtctgtta gttcaacaat ttagttattt aaaaatattt tgaaaacaag    6900
taagtttcta tgatacttca taataataag taataattaa ttgcttaatc atcatcacaa    6960
cattattcga aaccataact attcaattta agaagtaaaa acaataatat gagacaaata    7020
acaatggatc ctcttaatga atccactgtt aatgtctatc ttcccgactc atatcttaaa    7080
ggagtgattt cttttagtga gactaatgca attggttcat gtctcttaaa aagaccttac    7140
ctaaaaaatg acaacactgc aaaagttgcc atagagaatc ctgttatcga gcatgttaga    7200
ctcaaaaatg caatcaattc taagatgaaa atatcagatt acaggatagt agagccagta    7260
aacatgcaac atgaaattat gaagaatgta cacagttgtg agctcacatt attaaaacag    7320
tttttaacaa ggagtaaaaa tattagcact cttaaattaa atatgatatg tgattggctg    7380
cagttaaagt ctacatcaga tgatacctca atcttaagtt ttatagatgt agaatttata    7440
cctagctggg taagcaattg gtttagtaat tggtacaatc tcaacaagtt gattctggaa    7500
ttcaggaaag aagaagtaat aagaactggt tcaatcttgt gtaggtcatt gggtaaatta    7560 gttttttgttg tatcatcata cggatgtata gtcaagagca acaaaagcaa aagagtgagc    7620
ttcttcacat acaatcaact gttaacatgg aaagatgtga tgttaagtag attcaatgca    7680
aatttctgta tatgggtaag caacagtctg aatgaaaatc aagaagggtt agggttgaga    7740
agtaatctgc aaggcatatt aactaataag ctatatgaaa ctgtagatta tgcttagt    7800 ttgtgttgca atgaaggttt ctcacttgtg aaagagtttg agggttttat tatgagtgaa    7860
atccttagga ttactgaaca tgctcaattc agtactagat ttagaaatac tttattaaat    7920
ggattaactg atcaattgac aaaattaaaa aataaaaaca gactcagagt tcatggtacc    7980
gtgttagaaa ataatgatta tccaatgtat gaagttgtac ttaaattatt aggagatact    8040
ttgagatgta ttaaattatt aatcaataaa aacttagaga atgctgctga attatactat    8100
atatttagaa tattcggtca cccaatggta gatgaaagag atgcaatgga tgctgtcaaa    8160
ttaaacaatg aaatcacaaa aatcctcagg ttggagagct tgacagaact aagaggggca    8220
ttcatattaa ggattatcaa aggatttgta gacaacaaca aagatgcc gaaaattaaa    8280 aacttaaaag tgcttagtaa aagatggact atgtacttca agcaaaaag ttaccctagt    8340
```

```
caacttgaat taagtgaaca agatttttta gagcttgctg caatacagtt tgaacaagag    8400
ttttctgttc ctgaaaaaac caaccttgag atggtattaa atgataaagc tatatcacct    8460
cctaaaagat taatttggtc tgtgtaccca aaaaattact tacctgagac aataaaaaat    8520
cgatatctag aagagacttt caatgcaagt gatagtctca aaacaagaag agtactagag    8580
tactatttga aagataataa attcgaccaa aaagaactta aaagttatgt ggttaaacaa    8640
gaatatttaa atgataagga tcatattgtc tcgctaactg gaaagaaag agaattaagt     8700 gtaggtagaa tgtttgctat gcaaccagga aaacagcgac aaatacaaat attggctgaa    8760
aaattgttag ctgataatat tgtacccttt ttcccagaaa ctttaacaaa gtatggtgat    8820
ctagatcttc agagaataat ggaaatcaaa tcagaacttt cttctattaa aaccagaaga    8880
aatgatagtt ataataatta cattgcaaga gcatccatag taacagattt aagtaagttc    8940
aaccaagcct ttaggtatga aactacagcg atctgtgcgg atgtagcaga tgaactacat    9000
ggaacacaaa gcctattctg ttggttacat cttatcgttc ctatgactac aatgatatgt    9060
gcctatagac atgcaccacc agaaacaaaa ggtgaatatg atagataa gatagaagag      9120 caaagtggtt tatatagata tcatatgggt ggtattgaag gatggtgtca aaaactctgg    9180
acaatggaag ctatatcttt attagatgtt gtatctgtaa agcacgatg tcaaatgaca      9240 tctttattaa acggtgacaa ccaatcaata gatgtaagta aaccagttaa gttatctgag    9300
ggtttagatg aagtgaaagc agattatagc ttggctgtaa aaatgctaaa agaataaga    9360 gatgcataca gaaatatagg ccataaactt aagaagggg aaacatatat atcaagagat    9420 cttcagtttta taagtaaggt gattcaatct gaaggagtaa tgcatcctac ccctataaaa    9480
aagatcttaa gagtgggacc atggataaac acaatattag atgacattaa aaccagtgca    9540
gagtcaatag ggagtctatg tcaggaatta gaatttaggg gggaaagcat aatagttagt    9600
ctgatattaa ggaattttg gctgtataat ttatacatgc atgaatcaaa gcaacacccc     9660
ctagcaggga agcagttatt caaacaacta aataaaacat taacatcagt gcagagattt    9720
tttgaaatta aaaaggaaaa tgaagtagta gatctatgga tgaacatacc aatgcagttt    9780
ggaggaggag atccagtagt cttctataga tcttctctata gaaggacccc tgattttta    9840 actgaagcaa tcagtcatgt agatattctg ttaaaaatat cagccaacat aagaaatgaa    9900
gcgaaaataa gtttcttcaa agccttactg tcaatagaaa aaaatgaacg tgctacactg    9960
acaacactaa tgagagaccc tcaagctgtg ggctcagagc gacaagcaaa agtaacaagt   10020
gatatcaata gaacagcagt taccagcatc ttaagtcttt ctccaaatca acttttcagc   10080
gatagtgcta tacactacag tagaaatgaa gaagaggtcg gaatcattgc tgacaacata   10140
acacctgttt atcctcatgg actgagagtt ttgtatgaat cattacccttt tcataaagct   10200 gaaaaagttg taaatatgat atcaggaaca aaatccataa ccaacttatt acagagaaca   10260
tctgctatta atggtgaaga tattgacaga gctgtatcca tgatgctgga gaacctagga   10320
ttattatcta gaatattgtc agtagttgtt gatagtatag aaattccaac caaatctaat   10380
ggtaggctga tatgttgtca gatatctaga accctaaggg agacatcatg gaataatatg   10440
gaaatagttg gagtaacatc ccctagcatc actacatgca tggatgtcat atatgcaact   10500
agctctcatt tgaaagggat aatcattgaa aagttcagca ctgacagaac tacaagaggt   10560
caaagaggtc caaagagccc ttgggtagga tcgagcacgc aagagaaaaa attagttcct   10620
gtttataaca gacaaattct ttcaaaacaa caaagagaac agctagaagc aattggaaaa   10680
atgagatggg tatataaagg gacaccaggt ttaagacgat tactcaataa gatttgtctt   10740
```

```
ggaagtttag gcattagtta caaatgtgta aaacctttat tacctaggtt tatgagtgta    10800
aatttcctac acaggttatc tgtcagtagt agacctatgg aattcccagc atcagttcca    10860
gcttatagaa caacaaatta ccattttgac actagtccta ttaatcaagc actaagtgaa    10920
agatttggga atgaagatat taatttggtc ttccaaaatg caatcagctg tggaattagc    10980
ataatgagtg tagtagaaca attaactggt aggagtccaa acagttagt tttaataccc      11040 caattagaag aaatagacat tatgccacca ccagtgtttc aagggaaatt caattataag    11100
ctagtagata agataacttc tgaccaacat atcttcagtc cagacaaaat agatatgtta    11160
acactgggga aaatgctcat gccaactata aaggtcaga aaacagatca gttcttgaac       11220
aagagagaga attatttcca tgggaacaat cttattgagt ctttgtcagc agcgttagca    11280
tgtcattggt gtgggatatt aacagagcaa tgtatagaaa ataatatttt caagaaagac    11340
tggggtgacg ggttcatatc ggatcatgct tttatggact tcaaaatatt cctatgtgtc    11400
tttaaaacta aacttttatg tagttgggga tcccaaggga aaaacattaa agatgaagat    11460
atagtagatg aatcgataga taaactgtta aggattgata atacttttg gagaatgttc      11520 agcaaggtta tgtttgaatc aaaggttaag aaaaggataa tgttatatga tgtaaaattt    11580
ctatcattag taggttatat agggtttaag aattggttta tagaacagtt gagatcagct    11640
gagttgcatg aggtaccttg gattgtcaat gccgaaggtg atctggttga gatcaagtca    11700
attaaaatct atttgcaact gatagagcag agtttatttt taagaataac tgttttgaac    11760
tatacagata tggcacatgc tctcacaaga ttaatcagaa agaagttgat gtgtgataat    11820
gcactattaa cttcaattcc atccccaatg gttaacttaa ctcaagttat tgatcctaca    11880
gaacaattag cttatttccc taagataaca tttgaaaggc taaaaaatta tgacactagt    11940
tcaaattatg ctaaaggaaa gctaacaagg aattacatga tactgttgcc atggcaacat    12000
gttaatagat ataactttgt ctttagttct actggatgta aagttagtct aaaaacatgc    12060
attggaaaac ttatgaaaga tctaaaccct aaagttctgt actttattgg agaaggggca    12120
ggaaattgga tggccagaac agcatgtgaa tatcctgaca tcaaatttgt atacagaagt    12180
ttaaaagatg accttgatca tcattatcct ttggaatacc agagagtgat aggagaatta    12240
agcaggataa tagatagtgg tgaagggctt tcaatggaaa caacagatgc aactcaaaaa    12300
actcattggg atttgataca cagagtaagc aaagatgctt tattaataac tttatgtgat    12360
gcagaattta aggacagaga tgattttttt aagatggtaa ttctatggag gaaacatgta    12420
ttatcatgca gaatttgcac tacctatggg acagacctct atttattcgc aaagtatcat    12480
gctaaagact gcaatataaa attaccttt tttgtgagat cagttgccac ctttattatg       12540
caaggtagta aactgtcagg ctcggaatgc tacatactct taacactagg ccaccacaac    12600
aatttacctt gtcatggaga aatacaaaat tctaagatga aaatagcagc gtgtaatgat    12660
ttttatgctg caaaaaaact tgacaataaa tcaattgaag ccaactgtaa atcactttta    12720
tcagggctaa gaataccgat aaataagaag gaattaaata gacagagaag gttattaaca    12780
ctacaaagca accattcttc tgtagcaaca gttggaggta gcaaggtcat agagtctaaa    12840
tggttaacaa acaaggcaaa cacaataatt gattggttag aacatatttt aaattctcca    12900
aaaggtgaat taaattatga ttttttgaa gcattagaaa atacttaccc taatatgatt      12960
aaactaatag ataatctagg gaatgcagag attaaaaaac tgatcaaagt aactggatat    13020
atgcttgtaa gtaaaaaatg aaaaatgata aaaatgataa aataggtgac aacttcatac    13080
```

```
tattccaaag taatcatttg attatgcaat tatgtaatag ttaattaaaa actaaaaatc   13140
aaaagttaaa aactaataac tgtcattaag tttattaaaa ataagaaatt ataattggat   13200
gtatacggtt tttttgccgt                                               13220

<210> SEQ ID NO 7
<211> LENGTH: 13280
<212> TYPE: DNA
<213> ORGANISM: Human metapneumovirus

<400> SEQUENCE: 7
acgcgaaaaa aacgcgtata aattaaattc caaacaaaac gggacaaata aaaatgtctc     60
ttcaagggat tcacctaagt gatctgtcat ataaacatgc tatattaaaa gagtctcaat    120
acacaataaa aagagatgta ggcaccacaa ctgcagtgac accttcatca ttgcagcaag    180
agataacact tttgtgtgga gagattcttt acactaaaca tactgattac aaatatgctg    240
cagagatagg gatacaatat atttgcacgg ctctaggatc agaaagagta caacagattt    300
taagaaattc aggcagtgaa gttcaggtgg ttctaaccaa gacatactct ttagggaaag    360
gtaaaaatag taaaggggaa gagttgcaaa tgttagatat acatggagtg gaaaagagtt    420
gggtagaaga aatagacaaa gaggcaagaa aaacaatggt gactttgcta aaggaatcat    480
caggtaacat cccacaaaac cagaggcctt cagcaccaga cacaccaata atttttattat   540 gtgtaggtgc tttaatattc actaaactag catcaacaat agaagttgga ctagagacta    600
cagttagaag agctaacaga gtgctaagtg atgcgctcaa agatacccct agggtagata    660
taccgaagat tgctagatct ttctatgaac tatttgagca gaaagtgtat tacaggagtc    720
tattcattga gtatgggaaa gctttaggct catcttcaac aggaagcaaa gcagaaagtt    780
tgtttgtaaa tatatttatg caagcttatg gagccggtca acaatgcta aggtggggtg    840 tcattgccag atcatctaac aacataatgc taggacatgt gtctgtgcaa gctgaattga    900
agcaagttac agaggtttat gatttggtga gagaaatggg tcctgaatct gggcttttac    960
atctaagaca aagtccaaag gcaggactgt tatcgttggc caattgcccc gattttgcta   1020
gtgttgttct tggtaatgct tcaggtctag gtataatcgg aatgtacaga ggaagagtgc   1080
caaacacaga gctattttct gcagcagaaa gttatgccag aagcttaaaa gaaagcaaca   1140
aaatcaactt ctcctcatta gggctcacag acgaagaaaa agaagctgca gaacacttct   1200
taaacatgag tgatgacaat caagatgatt atgagtaatt aaaaaactgg gacaagtcaa   1260
aatgtcattc cctgaaggaa aagatatcct gttcatgggt aatgaagcag caaaaatagc   1320
agaagctttc cagaaatcac taaaaagatc aggtcacaaa gaacccagt ctattgtagg   1380 ggaaaaagta acactatat cagaaactct agagctacct accatcagca aacctgcacg   1440
atcatctaca ctgctagagc caaaattggc atgggcagac agcagcagag ccaccaaaac   1500
cacagaaaaa caaacaacca aacaacagat cctgttgaa gaagaggaac tcaatgaaaa   1560
gaagatatca ccttccagtg atgggaagac tcccgcagag aaaaaatcaa aatctccaac   1620
caatgtaaaa aagaaagttt ccttcacatc aaatgaacca gggaaatata ccaaactaga   1680
aaaagatgcc ctagatttgc tctcagacaa tgaggaagaa gacgcagagt cctcaatctt   1740
aacctttgaa gagagagaca catcatcact aagcattgag gctagactag aatcaataga   1800
agagaagcta agcatgatat taggactgct tcgtacactt aacattgcaa cagcaggacc   1860
aacggctgca gagatggaa tcagagatgc aatgattggt ataagagaag aactaatagc   1920
agaaataata aaagaagcaa agggaaaagc agctgaaatg atggaagagg aaatgaatca   1980
```

```
aaggtcaaaa ataggtaatg gcagtgtaaa actaaccgag aaggcaaaag aacttaataa    2040
aattgttgaa gacgagagca caagcggtga atcagaagaa gaagaagaac caaaagaaac    2100
tcaggataac aatcaaggag aagatattta ccagttaatc atgtagttta ataaaaataa    2160
acaatgggac aagtcaagat ggagtcctat ctagtggaca cttatcaagg cattccctac    2220
acagctgctg ttcaagttga tctggtagaa aaagacttac taccagcaag tttgacaata    2280
tggtttcctc tattccaagc caacacacca ccagcggttt tgctcgatca gctaaagacc    2340
ttgacaataa caactctgta tgctgcatca cagaatggtc caatactcaa ggtaaatgca    2400
tcagctcagg gtgctgctat gtctgtactt cccaaaaaat tcgaagtaaa tgcaactgtg    2460
gcacttgatg aatacagcaa acttgacttt gacaagttaa cggtttgcga tgttaaaaca    2520
gtttatttga caaccatgaa accatatggg atggtgtcaa aatttgtgag ttcagccaaa    2580
tcagttggca acaagacaca tgatctaatt gcactgtgtg acttcatgga cctagagaaa    2640
aatatacctg tgacaatacc agcattcata aagtcagttt caatcaaaga gagtgagtca    2700
gccactgttg aagctgcaat aagcagtgag gccgaccaag cattaacaca agccaaaatt    2760
gcaccctatg caggactaat catgatcatg accatgaaca atccaaaagg tatattcaag    2820
aaactaggag ctggaacaca agtgatagta gagctagggg catatgttca agccgagagc    2880
atcagcagga tctgcaagag ctggagtcac caaggaacaa gatatgtact aaaatccaga    2940
taaaaataac tgtcctaatc aataattgct tatataatct taaagatcaa tgagcttatt    3000
attatagtta tataaaaaaa tttagaacta ggaaggtatt aatagaaagc gggacaagta    3060
aaaatgtctt ggaaagtgat gattatcatt tcgttactca taacacctca gcacggacta    3120
aaggaaagtt atttagaaga atcatgtagt actataactg aaggatatct cagtgtttta    3180
agaacaggtt ggtacaccaa tgtctttaca ttagaagttg gtgatgttga aaatcttaca    3240
tgtactgatg gacctagctt aatcaaaaca gaacttgacc taaccaaaag tgctctaaga    3300
gaactcaaaa cagtttctgc tgatcagtta gcgagagaag aacaaattga aaatcccaga    3360
caatcaaggt ttgtcctagg tgcaatagct cttggtgttg ccacagcagc agcagtcaca    3420
gcaggcattg cgatagccaa aaccataagg cttgagagta agtgaatgc aatcaaaggt    3480 gctctcaaaa caaccaatga ggcagtatcc acactaggaa atggagtgcg agtcctagcc    3540
accgcagtaa gagagctgaa agaatttgtg agcaaaaacc tgactagtgc aattaacaag    3600
aacaaatgtg acattgctga tctgaagatg gctgtcagct tcagtcaatt caacagaaga    3660
ttcctaaatg ttgtgcggca gttttcagac aatgcaggga taacaccagc aatatcattg    3720
gacctaatga ctgatgctga gctggccaga gctgtatcat acatgccaac atctgcagga    3780
cagataaaac taatgttaga gaaccgtgca atggtgagga gaaaaggatt tggaatcttg    3840
atagggggct acggaagctc cgtgatttac atggtccagc tgccgatctt tggtgtcata    3900
gatacacctt gttggataat caaggcagct ccctcttgtt cagaaaaaga tggaaactat    3960
gcttgcctcc taagagagga tcaagggtgg tattgtaaaa atgcaggatc cactgtttac    4020
tacccaaata aaaaagactg cgaaacaaga ggtgatcatg ttttttgtga cacagctgca    4080
gggatcaatg ttgctgagca atcaagagaa tgcaacatca acatatctac aaccaactac    4140
ccatgcaaag tcagcacagg aagacacccct atcagcatgg ttgcactatc acctctcggt    4200
gctttggtgg cttgctacaa agggttagc tgttcaattg gcagtaatcg ggttggaata    4260
atcaaacaac tacctaaagg ctgctcatac ataactaacc aggacgcaga cactgtaaca    4320
```

-continued

```
attgacaaca ctgtgtatca actaagcaaa gttgagggtg aacagcatgt aataaaaggg    4380
agaccagttt caagcagttt cgatccaatc aagtttcctg aggatcagtt caatgttgcg    4440
cttgatcaag tctttgaaag cattgaaaac agtcaagcac tagtggacca gtcaaacaaa    4500
attctgaaca gtgcagaaaa aggaaacact ggcttcatta ttgtaataat tttgattgct    4560
gttcttgggt taaccatgat ttcagtgagc atcatcatca taatcaaaaa aacaaggaaa    4620
cccacagggg cacctccaga gctgaatggt gttaccaacg gcggttttat accgcatagt    4680
tagttaatta aaaaatggga caaatcatca tgtctcgtaa agctccatgc aaatatgaag    4740
tacggggcaa gtgcaacagg ggaagtgagt gcaaattcaa ccacaattac tggagttggc    4800
ctgataggta tttattgtta agatcaaatt atctcttgaa tcagcttta agaaacactg    4860 ataaggctga tggtttgtca ataatatcag gagcaggtag agaagacagg actcaagact    4920
ttgttcttgg ttctactaat gtggttcaag ggtacattga tgacaatcaa ggaataacaa    4980
aggctgcagc ttgctatagt ctacataaca taataaaaca gctacaagaa atagaagtaa    5040
gacaggccag agataataag ctttctgaca gcaaacatgt ggcacttcac aacttgatat    5100
tatcctatat ggagatgagc aaaactcctg catccctgat taataaccta agaaaactac    5160
caagagaaaa actgaaaaaa ttagcgaaat taataattga tttatcagca ggaactgata    5220
atgactcttc atatgccttg caagacagtg aaagcactaa tcaagtgcag taagcatggt    5280
cccaaattca tcaccataga ggcagatgat atgatatgga cacacaaaga attaaaagag    5340
acactgtctg atgggatagc aaaatcacac accaatattt acagttgtta tttagaaaat    5400
atagaaataa tatatgttaa agcttactta agttagtaaa aaataaatag aatgggataa    5460
atgacaatga aaacattaga tgtcataaaa agtgacggat cctcagaaac atgtaatcaa    5520
ctcaaaaaaa taataaaaaa acactcaggt aaattgctta ttgcatcaaa accgacattg    5580
gccttattga cgtccttcac agtaacaatt actgtcaact atacaaaagt agaaaataat    5640
ttgcaggcat gtcaattaaa aaatgaatca gacaaaaagg acacaaagct aaataccaca    5700
tcaacaacaa tcagacccat tcctgatcta aatgcagtac agtacctgaa aaggctgatt    5760
cagaaacaca ccaactctgt cacaaaagac agagatacct gttggagaat acacacgaat    5820
caatgcacaa atataaaaat atataagttc ttatgttttg ggtctatgaa ttcaacaaat    5880
acagactgtg aagaaccaac agttctatgc gacaaaaagt caaaaaccat gacagaaaaa    5940
cataggaaag cagagtgtca ccgtccacat acaaccgagt ggtggtgcca ttatctttaa    6000
gagaaaactc agttttcaac attaaaatca gaacaaatca tatctagatc tattaatata    6060
atagtctagt tatttaaaaa ctctaaatat tgtctagact tcacaacacc ctgcggtcat    6120
atgcaataat caatggtcaa accactgttg caaacccacc tataatacaa tcactgagta    6180
atacaaaaca agaaaatggg acaagtggcc atggaagcaa gagtggagaa cattcgggca    6240
atagacatgt tcaaagcaaa gatgaaaaac cgtataagaa gtagcaagtg ccatagaaat    6300
gctacactga tccttattgg atcaacagca ccaagtatgg cactcaacac ccttttaatc    6360
attgatcatg aacatcaaa aaacatgacc aaagtggaac actgtgtcaa catgccgccg    6420
gtagaaccaa gcaagaagac cccaatgacc tctgcagcag acccaaacac caaacccaat    6480
ccacagcagg caacacagct gaccacagag gattcaacat ctctagcagc aaccctagag    6540
gaccatctac acacagggac aactccaaca ccagatgcaa cagtctccca gcaaaccaca    6600
gacgagcaca caacactgct gagatcaacc aacagacaga ccacccaaac aaccgcagag    6660
aaaaagccaa ccagagcaac aaccaaaaaa gaaaccacaa ctcgaaccac aagcacagct    6720
```

```
gcaacccaaa cactcaacac caccaaccaa actagcaatg gaagagaggc aaccacaaca    6780
tctgccagat ccagaaacaa tgccacaact caaagcagcg atcaaacaac ccaggcagca    6840
gacccaagct cccaatcaca acatacacag aaaagcacaa caacaacaca caacacagac    6900
acatcttctc caagtagtta acaaaaaaac tataaaataa ccatgaaaac caaaaaacta    6960
gaaaagttaa tttgaactca gaaaagaaca caaacactat atgaattgtt tgagcgtata    7020
tactaatgaa atagcatctg tttgtgcatc aataatacca tcattattta agaaataaga    7080
agaagctaaa attcaaggga caaataacaa tggatccgtt ttgtgaatcc actgtcaatg    7140
tctatcttcc tgattcatat ctcaaaggag taatatcttt cagtgaaacc aatgcaattg    7200
gctcatgcct tttgaaaaga ccctatctta aaaagataa cactgctaaa gttgctgtag     7260
aaaaccctgt tgttgaacat gtcagactta gaaatgcagt catgaccaaa atgaagatat    7320
cagattataa agtggttgaa ccaattaata tgcagcatga ataatgaaa atatacaca      7380 gttgtgagct cacattatta aaacaattct taacaagaag taaaaacatt agctccctaa    7440
aattaagtat gatatgtgat tggttacagt taaaatccac ctcagataac acatcaattc    7500
ttaattttat agatgtggag tttatacccg tttgggtgag caattggttt agtaactggt    7560
ataatctcaa taaattaatc ttagagttta gaagagagga agtaataaga actggttcaa    7620
ttttatgcag atcactaggc aagttagttt tcattgtatc atcttatggg tgtgtagtaa    7680
aaagcaacaa aagtaaaaga gtaagttttt tcacatataa ccaactgtta acatggaaag    7740
atgtgatgtt aagtaggttc aatgcaaact tttgtatatg ggtaagtaac aacctgaaca    7800
aaaatcaaga aggactagga tttagaagta atctacaagg tatgttaact aataaattat    7860
atgaaactgt tgattatatg ttaagtctat gtagcaatga agggttctca ctagtgaaag    7920
agttcgaagg ctttattatg agtgaaattc ttaaaattac tgagcatgct caattcagta    7980
ctaggtttag gaatacttta ttaaatgggt tgactgaaca attatcaatg ttgaaagcta    8040
aaaacagatc tagagttctt ggcactatat agaaaacaa tgattacccc atgtatgaag     8100
tagtacttaa attattaggg gacactttga aaagtataaa attattaatt aacaagaatt    8160
tagaaaatgc tgcagaatta tattatatat tcagaatttt tggacaccct atggtagatg    8220
agagggaagc aatggatgct gttaaattaa ataatgagat tacaaaaatt cttaaactgg    8280
agagcttaac agaactaaga ggagcattta tactaagaat tataaaaggg tttgtagata    8340
ataataaaag atggcctaaa attaagaatt taaagtgct cagtaaaaga tgggttatgt     8400
atttcaaagc taaaagttac cctagccaac ttgagctaag tgtacaagat ttttttagaac   8460 ttgctgcagt acaattcgaa caggaatttt ctgtccctga aaaaccaat cttgagatgg     8520 tattaaatga taaagcaata tctccaccaa aaaagttaat atggtcggta tatccaaaaa    8580
attatctacc tgaaattata aaaaatcaat atttagaaga ggtcttcaat gcaagtgaca    8640
gtcaaagaac gaggagagtc ttagaatttt acttaaaaga ttgcaaattt gatcaaaaag    8700
acctcaaacg ttatgtaact aaacaagagt atctaaatga caaagaccac attgtctcat    8760
taactgggaa agaagagaa ttaagtgtag gcaggatgtt tgcaatgcaa cctggcaaac     8820
aaagacaaat acagatacta gccgagaaac ttttagctga taatattgta ccctttttcc    8880
cagaaacttt aacaaagtat ggtgacttgg atctccaaag aattatggaa atgaaatcag    8940
aactttcttc cattaaaact aggaagaatg atagttacaa caattatatt gcaagagcct    9000
ccatagtaac agacctaagt aaattcaatc aagcctttag atatgaaacc acagctatct    9060
```

```
gcgcagacgt agcagatgag ttacatggca cgcaaagctt attttgttgg ttacatctta    9120
ttgttcccat gaccacaatg atatgtgcat acagacatgc accaccagaa acaaaggggg    9180
agtatgatat agacaaaata gaagagcaaa gtgggctata cagataccat atgggaggga    9240
ttgaagggtg gtgtcagaag ttatggacaa tggaggcgat atccttgtta gatgtagtat    9300
ctgttaagac tcgttgtcag atgacctctc tattaaacgg agacaatcaa tcaatagatg    9360
tcagtaaacc agtaaaattg tctgaaggta tagatgaagt aaaagcagat tatagcttag    9420
caattaaaat gcttaaagag ataagagatg cctataaaaa cattggccat aaactcaaag    9480
aaggtgaaac atatatatca agagatcttc aatttataag taaggtgatt caatctgagg    9540
gggtcatgca tcctaccccc ataaaaaaga tattaagggt aggtccctgg ataaatacaa    9600
tactagatga cattaaaact agtgcagaat caatagggag tctgtgtcaa gaactagagt    9660
tcagaggaga aagtatacta gttagcttga tattaaggaa tttctggctg tataacttat    9720
acatgcatga gtcaaaacag catccgttag ctggaaaaca actgttttaaa caattgaaca    9780 aaacactaac atctgtgcaa agatttttg agctgaagaa agaaaatgat gtggttgacc    9840
tatggatgaa ataccaatg cagtttggag ggggagaccc agtagttttt tacagatctt    9900
tttacagaag gactcctgat ttcttgactg aagcaatcag ccatgtggat ttactgttaa    9960
aagtttcaaa caatattaaa aatgagacta agatacgatt cttttaaagcc ttattatcta   10020 tagaaaagaa tgaacgtgct acattaacaa cactaatgag agaccccag gcggtaggat   10080 cggaaagaca agctaaggta acaagtgata taaatagaac agcagttact agcatactga   10140
gtctatctcc gaatcagcta ttttgtgata gtgctataca ctatagcaga aatgaagaag   10200
aagtagggat cattgcagac aacataacac ctgtttatcc tcacggattg agagtgctct   10260
atgaatcact acctttcat aaggctgaaa aggttgtcaa tatgatatca ggtacaaagt   10320
ctataactaa cctattgcag agaacatctg ctatcaatgg tgaagatatt gatagagcag   10380
tgtctatgat gttagagaac ttagggttgt tatctaggat attgtcagta ataattaata   10440
gtatagaaat accaattaag tccaatggca gattgatatg ctgtcaaatt tctaagactt   10500
tgagagaaaa atcatggaac aatatggaaa tagtaggagt gacatctcca agtattgtaa   10560
catgtatgga tgttgtgtat gcgactagtt ctcatttaaa aggaataatt attgaaaaat   10620
tcagtactga caagaccaca agaggtcaga ggggaccaaa aagcccttgg gtaggatcaa   10680
gcactcaaga gaaaaaatta gttcctgttt ataacagaca aattctttca aaacaacaaa   10740
aagagcaact ggaagcaata ggaaaaatga ggtgggtgta taaaggaact ccagggctaa   10800
gaagattgct caataagatt tgcataggaa gtttaggtat tagctataaa tgtgtaaaac   10860
ctctattacc aagattttatg agtgtaaact tcttacatag gttatctgtt agtagcagac   10920
ccatggaatt cccagcttct gttccagctt ataggacaac aaattaccac tttgacacta   10980
gtccaatcaa ccaagcatta agtgagaggt tcgggaacga agacattaat ctagtgttcc   11040
aaaatgcaat cagctgcgga attagtataa tgagtgttgt agaacagtta actggtagaa   11100
gcccaaaaca attagtctta atccccccaat tagaagagat agatattatg cccctcctg   11160 tatttcaagg aaaattcaat tataaactag ttgataaaat aacctccgat caacacatct   11220
tcagtcctga caaaatagac atattaacac tagggaagat gcttatgcct actataaaag   11280
gtcaaaaaac tgatcagttc ttaaataaga gagaaaacta tttccatgga aataatttaa   11340
ttgaatcttt atctgcagca cttgcatgcc attggtgtgg aatattaaca gaacagtgtg   11400
tagaaaacaa tatctttagg aaagactggg gtgatgggt catatcagat catgccttca   11460
```

```
tggatttcaa gatatttcta tgtgtattta aaaccaaact tttatgtagt tggggatccc    11520
aagggaaaaa tgtaaaagat gaagatataa tagatgaatc cattgacaaa ttattaagaa    11580
ttgacaacac tttttggaga atgttcagca aagtcatgtt tgaatcaaag gtcaaaaaaa    11640
gaataatgtt atatgatgta aaattcctat cattagtagg ttatatagga tttaaaaact    11700
ggtttataga gcagttaaga gtagtagaat tgcatgaagt accctggatt gtcaatgctg    11760 aagggagct agttgaaatt aaaccaatca aaatttattt gcagttaata gaacaaagtc    11820
tatctttaag aataactgtt ttgaattata cagacatggc acatgctctt acacgattaa    11880
ttaggaagaa attgatgtgt gataatgcac tctttaatcc aagttcatca ccaatgttta    11940
gtctaactca agttattgat cctacaacac agctagacta ttttcctaag gtaatatttg    12000
aaaggttaaa aagttatgac accagttcag actacaacaa agggaagtta acaagaaatt    12060
acatgacatt attaccatgg cagcacgtaa acaggtataa ttttgtcttt agttcaacag    12120
gatgtaaaat cagcttgaag acatgcatcg ggaaattgat aaaggactta aaccctaagg    12180
ttctttactt tattggagaa ggagcaggta actggatggc aagaacagca tgtgagtatc    12240
ctgacataaa atttgtatat aggagtttaa aggatgatct tgatcaccat tacccattag    12300
aatatcaaag ggtaataggt gatttaaata gagtaataga tggtggtgaa ggattatcaa    12360
tggagaccac agatgcaact caaaagactc attgggactt gatacacaga ataagtaaag    12420
atgctttatt gataacattg tgtgatgcag aattcaaaaa cagagatgat ttctttaaaa    12480
tggtaattct ttggagaaaa catgtattat catgtagaat ctgtacagct tatggaacag    12540
atctttactt atttgcaaag tatcatgcga cggactgcaa tataaagtta ccatttttg    12600 taaggtctgt agctactttt attatgcaag gaagcaaatt gtcaggatca gaatgttaca    12660
tacttttaac attaggtcat cacaataatc tgccatgtca cggagaaata caaaattcca    12720
aaatgagaat agcagtgtgt aatgatttcc atgcctcaaa aaaactagac aacaaatcaa    12780
ttgaagcaaa ctgcaaatct cttctatcag gattaagaat accaataaac aaaaaagagt    12840
taaatagaca aaagaaactg ttaacactac aaagcaatca ttcttccata gcaacagttg    12900
gcggaagtaa gattatagaa tccaaatggt taaagaataa agcaagtaca ataattgatt    12960
ggttagagca tatcttgaat tctccaagag gtgaattaaa ctatgatttc tttgaagcat    13020
tagagaacac atatcccaat atgatcaagc ttatagataa cctgggaaat gcagagataa    13080
aaaaactaat caaagttacc gggtatatgc ttgtgagtga aagtaataa taataataat    13140 aatcaaccat aatctcacac aactgagaaa atgatcatct aacagtttaa ttgaccatta    13200
gttaattaaa aattataaat tagtaactaa ttgataaaaa ataagaaatt gaattgaat    13260 gtatacggtt ttttgccgt                                                 13280
```

<210> SEQ ID NO 8  
<211> LENGTH: 14028  
<212> TYPE: DNA  
<213> ORGANISM: Artificial Sequence  
<220> FEATURE:  
<223> OTHER INFORMATION: GFP encoding gene is inserted between  
      nucleotides 41 and 785

<400> SEQUENCE: 8

```
acgcgaaaaa aacgcgtata aattaaattc caaacaaaac gggacaaata aaatggtga       60 gcaagggcga ggagctgttc accggggtgg tgcccatcct ggtcgagctg gacgcgacg      120 taaacggcca caagttcagc gtgtccggcg agggcgaggg cgatgccacc tacggcaagc    180
```

```
tgaccctgaa gttcatctgc accaccggca agctgcccgt gccctggccc accctcgtga      240
ccaccctgac ctacggcgtg cagtgcttca gccgctaccc cgaccacatg aagcagcacg      300
acttcttcaa gtccgccatg cccgaaggct acgtccagga gcgcaccatc ttcttcaagg      360
acgacggcaa ctacaagacc cgcgccgagg tgaagttcga gggcgacacc ctggtgaacc      420
gcatcgagct gaagggcatc gacttcaagg aggacggcaa catcctgggg cacaagctgg      480
agtacaacta caacagccac aacgtctata tcatggccga caagcagaag aacggcatca      540
aggtgaactt caagatccgc cacaacatcg aggacggcag cgtgcagctc gccgaccact      600
accagcagaa cacccccatc ggcgacggcc ccgtgctgct gcccgacaac cactacctga      660
gcacccagtc cgccctgagc aagacccca acgagaagcg cgatcacatg gtcctgctgg      720
agttcgtgac cgccgccggg atcactctcg gcatggacga gctgtacaag taagttaatt      780
aaaaaactgg gacaaataaa aatgtctctt caagggattc acctaagtga tctgtcatat      840
aaacatgcta tattaaaaga gtctcaatac acaataaaaa gagatgtagg caccacaact      900
gcagtgacac cttcatcatt gcagcaagag ataacacttt tgtgtggaga gattctttac      960
actaaacata ctgattacaa atatgctgca gagatagga tacaatatat ttgcacggct     1020
ctaggatcag aaagagtaca acagatttta agaaattcag gcagtgaagt tcaggtggtt     1080
ctaaccaaga catactcttt agggaaaggt aaaaatagta aagggaaga gttgcaaatg     1140 ttagatatac atggagtgga aaagagttgg gtagaagaaa tagacaaaga ggcaagaaaa     1200
acaatggtga ctttgctaaa ggaatcatca ggtaacatcc cacaaaacca gaggccttca     1260
gcaccagaca caccaataat tttattatgt gtaggtgctt taatattcac taaactagca     1320
tcaacaatag aagttggact agagactaca gttagaagag ctaacagagt gctaagtgat     1380
gcgctcaaaa gataccctag ggtagatata ccgaagattg ctagatcttt ctatgaacta     1440
tttgagcaga aagtgtatta caggagtcta ttcattgagt atgggaaagc tttaggctca     1500
tcttcaacag gaagcaaagc agaaagtttg tttgtaaata tatttatgca agcttatgga     1560
gccggtcaaa caatgctaag gtggggtgtc attgccagat catctaacaa cataatgcta     1620
ggacatgtgt ctgtgcaagc tgaattgaag caagttacag aggtttatga tttggtgaga     1680
gaaatgggtc ctgaatctgg gcttttacat ctaagacaaa gtccaaaggc aggactgtta     1740
tcgttggcca attgccccaa ttttgctagt gttgttcttg gtaatgcttc aggtctaggt     1800
ataatcggaa tgtacagagg aagagtgcca acacagagc tattttctgc agcagaaagt     1860
tatgccagaa gcttaaaaga aagcaacaaa atcaacttct cctcattagg gctcacagac     1920
gaagaaaaag aagctgcaga acacttctta aacatgagtg atgacaatca agatgattat     1980
gagtaattaa aaaactggga caagtcaaaa tgtcattccc tgaaggaaaa gatatcctgt     2040
tcatgggtaa tgaagcagca aaatagcag aagcttccca gaaatcacta aaaagatcag     2100
gtcacaaaag aacccagtct attgtagggg aaaagtaaa cactatatca gaaactctag     2160
agctacctac catcagcaaa cctgcacgat catctacact gctagagcca aaattggcat     2220
gggcagacag cagcagagcc accaaaacca cagaaaaaca aacaaccaaa acaacagatc     2280
ctgttgaaga agaggaactc aatgaaaaga agatatcacc ttccagtgat gggaagactc     2340
ccgcagagaa aaaatcaaaa tctccaacca atgtaaaaaa gaaagttccc ttcacatcaa     2400
atgaaccagg gaaatatacc aaactagaaa agatgccct agatttgctc tcagacaatg     2460
aggaagaaga cgcagagtcc tcaatcttaa cctttgaaga gagagacaca tcatcactaa     2520
```

```
gcattgaggc tagactagaa tcaatagaag agaagctaag catgatatta ggactgcttc    2580
gtacacttaa cattgcaaca gcaggaccaa cggctgcaag agatggaatc agagatgcaa    2640
tgattggtat aagagaagaa ctaatagcag aaataataaa agaagcaaag ggaaaagcag    2700
ctgaaatgat ggaagaggaa atgaatcaaa ggtcaaaaat aggtaatggc agtgtaaaac    2760
taaccgagaa ggcaaaagaa cttaataaaa ttgttgaaga cgagagcaca agcggtgaat    2820
cagaagaaga agaagaacca aaagaaactc aggataacaa tcaaggagaa gatatttacc    2880
agttaatcat gtagtttaat aaaaataaac aatgggacaa gtcaagatgg agtcctatct    2940
agtggacact tatcaaggca ttccctacac agctgctgtt caagttgatc tggtagaaaa    3000
agacttacta ccagcaagtt tgacaatatg gtttcctcta ttccaagcca acacaccacc    3060
agcggttttg ctcgatcagc taaagacctt gacaataaca actctgtatg ctgcatcaca    3120
gaatggtcca atactcaagg taaatgcatc agctcagggt gctgctatgt ctgtacttcc    3180
caaaaaattc gaagtaaatg caactgtggc acttgatgaa tacagcaaac ttgactttga    3240
caagttaacg gtttgcgatg ttaaaacagt ttatttgaca accatgaaac catatgggat    3300
ggtgtcaaaa tttgtgagtt cagccaaatc agttggcaac aagacacatg atctaattgc    3360
actgtgtgac ttcatggacc tagagaaaaa tatacctgtg acaataccag cattcataaa    3420
gtcagtttca atcaaagaga gtgagtcagc cactgttgaa gctgcaataa gcagtgaggc    3480
cgaccaagca ttaacacaag ccaaaattgc accctatgca ggactaatca tgatcatgac    3540
catgaacaat ccaaaaggta tattcaagaa actaggagct ggaacacaag tgatagtaga    3600 gctagggca tatgttcaag ccgagagcat cagcaggatc tgcaagagct ggagtcacca    3660
aggaacaaga tatgtactaa aatccagata aaaataactg tcctaatcaa taattgctta    3720
tataatctta aagatcaatg agcttattat tatagttata taaaaaaatt tagaactagg    3780
aaggtattaa tagaaagcgg gacaagtaaa aatgtcttgg aaagtgatga ttatcatttc    3840
gttactcata acacctcagc acggactaaa ggaaagttat ttagaagaat catgtagtac    3900
tataactgaa ggatatctca gtgttttaag aacaggttgg tacaccaatg tctttacatt    3960
agaagttggt gatgttgaaa atcttacatg tactgatgga cctagcttaa tcaaaacaga    4020
acttgaccta accaaaagtg ctctaagaga actcaaaaca gtttctgctg atcagttagc    4080
gagagaagaa caaattgaaa atcccagaca atcaaggttt gtcctaggtg caatagctct    4140
tggtgttgcc acagcagcag cagtcacagc aggcattgcg atagccaaaa ccataaggct    4200
tgagagtgaa gtgaatgcaa tcaaaggtgc tctcaaaaca accaatgagg cagtatccac    4260
actaggaaat ggagtgcgag tcctagccac cgcagtaaga gagctgaaag aatttgtgag    4320
caaaaacctg actagtgcaa ttaacaagaa caaatgtgac attgctgatc tgaagatggc    4380
tgtcagcttc agtcaattca acagaagatt cctaaatgtt gtgcggcagt tttcagacaa    4440
tgcagggata acaccagcaa tatcattgga cctaatgact gatgctgagc tggccagagc    4500
tgtatcatac atgccaacat ctgcaggaca gataaaacta atgttagaga accgtgcaat    4560
ggtgaggaga aaaggatttg gaatcttgat aggggtctac ggaagctccg tgatttacat    4620
ggtccagctg ccgatctttg gtgtcataga tacccttgt tggataatca aggcagctcc    4680
ctcttgttca gaaaaagatg gaaactatgc ttgcctccta agagaggatc aagggtggta    4740
ttgtaaaaat gcaggatcca ctgtttacta cccaaatgaa aaagactgcg aaacaagagg    4800
tgatcatgtt ttttgtgaca cagctgcagg gatcaatgtt gctgagcaat caagagaatg    4860
caacatcaac atatctacaa ccaactaccc atgcaaagtc agcacaggaa gacaccctat    4920
```

```
cagcatggtt gcactatcac ctctcggtgc tttggtggct tgctacaaag gggttagctg   4980
ttcaattggc agtaatcggg ttggaataat caaacaacta cctaaaggct gctcatacat   5040
aactaaccag gacgcagaca ctgtaacaat tgacaacact gtgtatcaac taagcaaagt   5100
tgagggtgaa cagcatgtaa taaaagggag accagtttca agcagtttcg atccaatcaa   5160
gtttcctgag gatcagttca atgttgcgct tgatcaagtc tttgaaagca ttgaaaacag   5220
tcaagcacta gtggaccagt caaacaaaat tctgaacagt gcagaaaaag gaaacactgg   5280
cttcattatt gtaataattt tgattgctgt tcttgggtta accatgattt cagtgagcat   5340
catcatcata atcaaaaaaa caaggaaacc cacaggggca cctccagagc tgaatggtgt   5400
taccaacggc ggttttatac cgcatagtta gttaattaaa aaatgggaca aatcatcatg   5460
tctcgtaaag ctccatgcaa atatgaagta cggggcaagt gcaacagggg aagtgagtgc   5520
agattcaacc acaattactg gagttggcct gataggtatt tattgttaag atcaaattat   5580
ctcttgaatc agcttttaag aaacactgat aaggctgatg gtttgtcaat aatatcagga   5640
gcaggtagag aagacaggac tcaagacttt gttcttggtt ctactaatgt ggttcaaggg   5700
tacattgatg acaatcaagg aataacaaag gctgcagctt gctatagtct acataacata   5760
ataaaacagc tacaagaaat agaagtaaga caggccagag ataataagct ttctgacagc   5820
aaacatgtgg cacttcacaa cttgatatta tcctatatgg agatgagcaa actcctgca   5880 tccctgatta ataacctaaa gaaactacca agagaaaaac tgaaaaaatt agcgaaatta   5940
ataattgatt tatcagcagg aactgataat gactcttcat atgccttgca agacagtgaa   6000
agcactaatc aagtgcagta agcatggtcc caaattcatt accatagagg cagatgatat   6060
gatatggaca cacaaagaat taaaagagac actgtctgat gggatagtaa aatcacacac   6120
caatatttac agttgttatt tagaaaatat agaaataata tatgttaaag cttacttaag   6180
ttagtaaaaa ataatagaa tgggataaat gacaatgaaa acattagatg tcataaaaag   6240
tgacggatcc tcagaaacat gtaatcaact caaaaaaata ataaaaaaac actcaggtaa   6300
attgcttatt gcattaaaac tgatattggc cttattgacg ttttcacag taacaattac   6360 tgttaactat ataaaagtag aaaataattt gcaggcatgt caattaaaaa atgaatcaga   6420
caaaaaggac acaaagctaa ataccacatc aacaacaatc agacccattc ctgatctaaa   6480
tgcagtacag tacttgaaaa ggctgattca gaaacacacc aactttgtca taaagacaga   6540
agatacctgt tggagaatac acacgaatca atgcacaaat ataaaatat ataagttctt   6600 atgttttggg tctatgaatt caacaaatac agactgtgaa gaactaacag ttttatgcga   6660
caaaaagtca aaaccatga cagaaaaaca taggaaagca gagtgtcact gtctacatac   6720
aaccgagtgg tggtgttatt atcttttaaga gaaaactcag ttttcaacat aaaatcaga   6780 acaaatcata tctagatcta ttaatataat agtttagtta tttaaaaact ctaaatattg   6840
tctagacttc acaacacttt gcggtcatat gcaataatca atggtcaaac cactgttgca   6900
aactcaccta taatataatc actgagtaat acaaaacaag aaaatgggac aagtggccat   6960
ggaagtaaga gtggagaaca ttcgggcaat agacatgttc aaagcaaaga tgaaaaaccg   7020
tataagaagt agcaagtgct atagaaatgc tacactgatc cttattggat caacagcact   7080
aagtatggca ctcaatattt ttttaatcat tgattatgca acatcaaaaa acatgaccaa   7140
agtggaacac tgtgtcaata tgccgccggt agaaccaagc aagaagaccc caatgacctc   7200
tgcagtagac ccaaacacca aacccaatcc acagcaggca acacagctga ccacagagga   7260
```

```
ttcaacatct ctagcagcaa ccctagagga ccatctacac acagggacaa ctccaacacc    7320
agatgcaaca gtctctcagc aaaccacaga cgagcacaca acactgctga gatcaaccaa    7380
cagacagacc acccaaacaa ccgcagagaa aaagccaacc agagcaacaa ccaaaaaaga    7440
aaccacaact cgaaccacaa gcacagctgc aacccaaaca ctcaacacca ccaaccaaac    7500
tagcaatgga agagaggcaa ccacaacatc tgccagatcc agaaacaatg ccacaactca    7560
aagcagcgat caaacaaccc aggcagcaga cccaagctcc caatcacaac atacacagaa    7620
aagcacaaca acaacacaca acacagacac atcttctcca agtagttaac aaaaaaacta    7680
taaaataacc atgaaaacca aaaaactaga aaagttaatt tgaactcaga aaagaacaca    7740
aacactatat gaattgtttg agcgtatata ctaatgaaat agcatctgtt tgtgcatcaa    7800
taataccatc attatttaag aaataagaag aagctaaaat tcaagggaca ataacaatg     7860 gatccgtttt gtgaatccac tgtcaatgtc tatcttcctg attcatatct caaaggagta    7920
atatctttca gtgaaaccaa tgcaattggc tcatgccttt tgaaaagacc ctatcttaaa    7980
aaagataaca ctgctaaagt tgctgtagaa accctgttg ttgaacatgt cagacttaga     8040
aatgcagtca tgaccaaaat gaagatatca gattataaag tggttgaacc aattaatatg    8100
cagcatgaaa taatgaaaaa tatacacagt tgtgagctca cattattaaa acaattctta    8160
acaagaagta aaacattag ctccctaaaa ttaagtatga tatgtgattg gttacagtta      8220
aaatccacct cagataacac atcaattctt aattttatag atgtggagtt tatacccgtt    8280
tgggtgagca attggtttag taactggtat aatctcaata aattaatctt agagtttaga    8340
agagaggaag taataagaac tggttcaatt ttatgcagat cactaggcaa gttagttttc    8400
attgtatcat cttatgggtg tgtagtaaaa agcaacaaaa gtaaaagagt aagtttttc     8460 acatataacc aactgttaac atggaaagat gtgatgttaa gtaggttcaa tgcaaacttt    8520
tgtatatggg taagtaacaa cctgaacaaa aatcaagaag gactaggatt tagaagtaat    8580
ctacaaggta tgttaactaa taaattatat gaaactgttg attatatgtt aagtctatgt    8640
agcaatgaag ggttctcact agtgaaagag ttcgaaggct ttattatgag tgaaattctt    8700
aaaattactg agcatgctca attcagtact aggtttagga atactttatt aaatgggttg    8760
actgaacaat tatcaatgtt gaaagctaaa acagatcta gagttcttgg cactatatta     8820
gaaaacaatg attaccccat gtatgaagta gtacttaaat tattagggga cactttgaaa    8880
agtataaaat tattaattaa caagaattta gaaaatgctg cagaattata ttatatattc    8940 agaattttg gacaccctat ggtagatgag agggaagcaa tggatgctgt taaattaaat     9000
aatgagatta caaaaattct taaactggag agcttaacag aactaagagg agcatttata    9060
ctaagaatta taaagggtt tgtagataat aataaaagat ggcctaaaat taagaattta     9120
aaagtgctca gtaaaagatg ggttatgtat ttcaaagcta aaagttaccc tagccaactt    9180
gagctaagtg tacaagattt tttagaactt gctgcagtac aattcgaaca ggaattttct    9240
gtccctgaaa aaaccaatct tgagatggta ttaaatgata aagcaatatc tccaccaaaa    9300
aagttaatat ggtcggtata tccaaaaaat tatctacctg aaattataaa aaatcaatat    9360
ttagaagagg tcttcaatgc aagtgacagt caaagaacga ggagagtctt agaattttac    9420
ttaaaagatt gcaaatttga tcaaaagac ctcaaacgtt atgtaactaa acaagagtat      9480
ctaaatgaca aagaccacat tgtctcatta actgggaaag aaagagaatt aagtgtaggc    9540
aggatgtttg caatgcaacc tggcaaacaa agacaaatac agatactagc cgagaaactt    9600
ttagctgata atattgtacc ctttttccca gaaactttaa caaagtatgg tgacttggat    9660
```

```
ctccaaagaa ttatggaaat gaaatcagaa ctttcttcca ttaaaactag gaagaatgat    9720
agttacaaca attatattgc aagagcctcc atagtaacag acctaagtaa attcaatcaa    9780
gcctttagat atgaaaccac agctatctgc gcagacgtag cagatgagtt acatggcacg    9840
caaagcttat tttgttggtt acatcttatt gttcccatga ccacaatgat atgtgcatac    9900
agacatgcac caccagaaac aaaggggag tatgatatag acaaaataga gagcaaagt     9960
gggctataca gataccatat gggagggatt gaagggtggt gtcagaagtt atggacaatg   10020
gaggcgatat ccttgttaga tgtagtatct gttaagactc gttgtcagat gacctctcta   10080
ttaaacggag acaatcaatc aatagatgtc agtaaaccag taaaattgtc tgaaggtata   10140
gatgaagtaa aagcagatta tagcttagca attaaaatgc ttaaagagat aagagatgcc   10200
tataaaaaca ttggccataa actcaaagaa ggtgaaacat atatatcaag agatcttcaa   10260
tttataagta aggtgattca atctgagggg gtcatgcatc ctaccccat aaaaaagata    10320
ttaagggtag gtccctggat aaatacaata ctagatgaca ttaaaactag tgcagaatca   10380
ataggagtc tgtgtcaaga actagagttc agaggagaaa gtatactagt tagcttgata   10440
ttaaggaatt tctggctgta taacttatac atgcatgagt caaaacagca tccgttagct   10500
ggaaaacaac tgtttaaaca attgaacaaa acactaacat ctgtgcaaag attttttgag   10560
ctgaagaaag aaaatgatgt ggttgaccta tggatgaata taccaatgca gtttggaggg   10620
ggagacccag tagtttttta cagatctttt tacagaagga ctcctgattt cttgactgaa   10680
gcaatcagcc atgtggattt actgttaaaa gtttcaaaca atattaaaaa tgagactaag   10740
atacgattct ttaaagcctt attatctata gaaaagaatg aacgtgctac attaacaaca   10800
ctaatgagag acccccaggc ggtaggatcg gaaagacaag ctaaggtaac aagtgatata   10860
aatagaacag cagttactag catactgagt ctatctccga atcagctatt ttgtgatagt   10920
gctatacact atagcagaaa tgaagaagaa gtagggatca ttgcagacaa cataacacct   10980
gtttatcctc acggattgag agtgctctat gaatcactac cttttcataa ggctgaaaag   11040
gttgtcaata tgatatcagg tacaaagtct ataactaacc tattgcagag aacatctgct   11100
atcaatggtg aagatattga tagagcagtg tctatgatgt tagagaactt agggttgtta   11160
tctaggatat tgtcagtaat aattaatagt atagaaatac caattaagtc caatggcaga   11220
ttgatatgct gtcaaatttc taagacttg agagaaaaat catggaacaa tatggaaata   11280
gtaggagtga catctccaag tattgtaaca tgtatggatg ttgtgtatgc gactagttct   11340
catttaaaag gaataattat tgaaaaattc agtactgaca agaccacaag aggtcagagg   11400
ggaccaaaaa gcccttgggt aggatcaagc actcaagaga aaaattagt tcctgtttat   11460
aacagacaaa ttctttcaaa acaacaaaaa gagcaactgg aagcaatagg aaaaatgagg   11520
tgggtgtata aaggaactcc agggctaaga agattgctca ataagatttg cataggaagt   11580
ttaggtatta gctataaatg tgtaaaacct ctattaccaa gatttatgag tgtaaacttc   11640
ttacataggt tatctgttag tagcagaccc atggaattcc cagcttctgt tccagcttat   11700
aggacaacaa attaccactt tgacactagt ccaatcaacc aagcattaag tgagaggttc   11760
gggaacgaag acattaatct agtgttccaa aatgcaatca gctgcggaat tagtataatg   11820
agtgttgtag aacagttaac tggtagaagc ccaaaacaat tagtcttaat cccccaatta   11880
gaagagatag atattatgcc ccctcctgta tttcaaggaa aattcaatta taaactagtt   11940
gataaaatat cctccgatca acacatcttc agtcctgaca aaatagacat attaacacta   12000
```

```
gggaagatgc ttatgcctac tataaaaggt caaaaaactg atcagttctt aaataagaga    12060
gaaaactatt tccatggaaa taatttaatt gaatctttat ctgcagcact tgcatgccat    12120
tggtgtggaa tattaacaga acagtgtgta gaaaacaata tctttaggaa agactggggt    12180
gatgggttca tatcagatca tgccttcatg gatttcaaga tatttctatg tgtatttaaa    12240
accaaacttt tatgtagttg gggatcccaa gggaaaatg taaagatga agatataata     12300 gatgaatcca ttgacaaatt attaagaatt gacaacactt tttggagaat gttcagcaaa    12360
gtcatgtttg aatcaaaggt caaaaaaaga ataatgttat atgatgtaaa attcctatca    12420
ttagtaggtt ataggatt taaaaactgg tttatagagc agttaagagt agtagaattg      12480
catgaagtac cctggattgt caatgctgaa ggggagctag ttgaaattaa accaatcaaa    12540
atttatttgc agttaataga acaaagtcta tctttaagaa taactgtttt gaattataca    12600
gacatggcac atgctcttac acgattaatt aggaagaaat tgatgtgtga taatgcactc    12660
tttaatccaa gttcatcacc aatgtttagt ctaactcaag ttattgatcc tacaacacag    12720
ctagactatt ttcctaaggt aatatttgaa aggttaaaaa gttatgacac cagttcagac    12780
tacaacaaag ggaagttaac aagaaattac atgcatattt taccatggca gcacgtaaac    12840
aggtataatt ttgtctttag ttcaacagga tgtaaaatca gcttgaagac atgcatcggg    12900
aaattgataa aggacttaaa ccctaaggtt ctttacttta ttggagaagg agcaggtaac    12960
tggatggcaa gaacagcatg tgagtatcct gacataaaat ttgtatatag gagtttaaag    13020
gatgatcttg atcaccatta cccattagaa tatcaaaggg taataggtga tttaaataga    13080
gtaatagatg tggtgaagg attatcaatg gagaccacag atgcaactca aaagactcat     13140
tgggacttga tacacagaat aagtaaagat gctttattga taacattgtg tgatgcagaa    13200
ttcaaaaaca gagatgattt cttttaaaatg gtaattcttt ggagaaaaca tgtattatca    13260
tgtagaatct gtacagctta tggaacagat ctttacttat ttgcaaagta tcatgcgacg    13320
gactgcaata taaagttacc attttttgta aggtctgtag ctacttttat tatgcaagga    13380
agcaaattgt caggatcaga atgttacata cttttaacat taggtcatca caataatctg    13440
ccatgtcacg gagaaataca aaattccaaa atgagaatag cagtgtgtaa tgatttccat    13500
gcctcaaaaa aactagacaa caaatcaatt gaagcaaact gcaaatctct tctatcagga    13560
ttaagaatac caataaacaa aaaagagtta aatagacaaa agaaactgtt aacactacaa    13620
agcaatcatt cttccatagc aacagttggc ggaagtaaga ttatagaatc caaatggtta    13680
aagaataaag caagtacaat aattgattgg ttagagcata tcttgaattc tccaaaaggt    13740
gaattaaact atgatttctt tgaagcatta gagaacacat atcccaatat gatcaagctt    13800
atagataacc tgggaaatgc agagataaaa aaactaatca aagttaccgg gtatatgctt    13860
gtgagtgaga agtaataata ataataataa tcaaccataa tctcacacaa ctgagaaaat    13920
gatcatctaa cagtttaatt gaccattagt taattaaaaa ttataaatta gtaactaatt    13980
gataaaaaat aagaaattga aattgaatgt atacggtttt tttgccgt                 14028
```

ATTENUATED VIRUS STRAIN AND USE THEREOF AS A VACCINE

SEQUENCE LISTING

The instant application contains a Sequence Listing which has been submitted in ASCII format via EFS-Web and is hereby incorporated by reference in its entirety. Said ASCII copy, created on Feb. 4, 2021, is named 17262263_Sequence_Listing.txt and is 140,297 bytes in size.

FIELD OF THE INVENTION

The present invention relates to virus strains genetically modified from a new human metapneumovirus strain.

The present invention relates to these modified strains, of which the virulence is attenuated, for the use thereof in the prophylactic or therapeutic treatment of infections with viruses of the Pneumoviridae family, as well as vaccine compositions comprising said modified virus strains.

INTRODUCTION

Acute infections of the lower respiratory tracts are one of the major causes of morbidity and mortality on the global scale. In children less than 5 years old in particular, they represent up to more than 15% of mortality, depending on the countries evaluated, and are thus the second cause of mortality according to the World Health Organisation.

The majority of acute infections of the lower respiratory tracts, associated with variable pathologies ranging from a simple cold to serious pneumonia, are notably caused by viruses, such as those belonging to the following families:
(i) virus of the Orthomyxoviridae family (notably comprising Influenza viruses);
(ii) virus of the Paramyxoviridae family;
(iii) virus of the Adenoviridae family;
(iv) virus of the Picornaviridae family;
(v) virus of the Coronaviridae family and
(vi) virus of the Pneumoviridae family, notably comprising the human syncytial respiratory virus and the human metapneumovirus virus.

The human syncytial respiratory virus (hRSV) and the human metapneumovirus (hMPV) are viruses responsible for acute infections of the respiratory tracts such as bronchiolitis, bronchitis or pneumonias. They mainly affect populations at risk, which are young children less than 5 years old, the elderly and immuno-depressed persons.

The hRSV is the main etiological agent of bronchiolitis and pneumonias in infants less than 1 year old, with an increased incidence below 6 months old. In adults, infection with hRSV is rare and benign, expect in elderly subjects. Transmission essentially takes place by respiratory route, the virus replicating in the respiratory tract.

The hRSV was isolated in 1957. It is a virus with single-stranded RNA of negative polarity, of "enveloped" type, with helical symmetry capsid. It belongs to the family Pneumoviridae and to the genus Orthopneumovirus.

The hMPV is prevalent in bronchiolitis and pneumonias in infants, and particularly severely affects children between 1 and 3 years old.

The main symptoms of infection by hMPV in children comprise rhinorrhoea, coughing, respiratory distress or instead fever. hMPV may also cause infections of the upper respiratory tracts, being able to be associated with ear infections, whereas non-respiratory symptoms, such as diarrhoea, vomiting and the occurrence of erythema, are rarer. hMPV preferentially targets the ciliated cells of the human respiratory tree.

An infection by hMPV induces histo-pathological modifications in the lungs of the host organism, and generates in particular the following physiological effects:
Damage at the level of the respiratory epithelium;
Excessive production of mucus, and
Acute inflammation, notably at the level of the interstitial pulmonary tissues, linked to an important secretion of pro-inflammatory cytokines and chemokines.

In respiratory pathologies in adults, hMPV has been identified in 5 to 10% of adults or older persons having an acute infection of the respiratory tracts, and in 3 to 5% of adults having an exacerbation of a chronic pulmonary pathology or a pneumonia acquired in community.

The hMPV was isolated and described for the first time in 2001 in the Netherlands (van den Hoogen et al., 2001). The following year, several strains of hMPV were isolated in patients located in North America (Peret et al., 2002). hMPV are viruses with negative single-stranded RNA, belonging to the family Pneumoviridae and to the genus Metapneumovirus.

The average age of children hospitalised due to complications of an infection by hMPV is 6 to 12 months, i.e. later than that caused by hRSV, which mainly occurs between 0 and 3 months. However, the epidemiology of hMPV has numerous common points with that of hRSV:
it is present on all continents;
its annual distribution is mainly in winter and spring, overlapping that of hRSV;
its transmission probably also takes place by salivary droplets.

No prophylactic or therapeutic modality that is efficient and specific against infection by the viruses hRSV and hMPV exists today on the market, although active research is underway (Mazur et al., 2018).

For treatment, ribavirin, not exempt from undesirable effects, or intravenous immunoglobulins, very expensive, may be used occasionally in serious cases of infections by hMPV or hRSV.

Other types of treatments are currently being developed such as the use of fusion inhibitor peptides, sulphated glycosaminoglycans, interfering RNAs and certain immunomodulators.

The usual and widely favoured clinical approach today consists in treating especially the symptoms of the infection, while placing patients under respiratory assistance (administration of oxygen or mechanical ventilation) and by administering to them bronchodilators, corticosteroids and/or antibiotics for preventing or treating bacterial superinfections.

Regarding the vaccination, the populations particularly affected by hMPV being infants, young children and the elderly, it is crucial to have rapidly safe and effective vaccines, in order to reduce severe respiratory attacks which have a dramatic impact in these age ranges.

The development of a vaccine against hRSV and hMPV thus represents not only a major health challenge, but also a real socio-economic issue with the objective of reducing the high cost of treatments and hospitalisations associated with these infections, and of decreasing the use of antibiotics in the context of bacterial superinfections, and thus limiting the emergence of resistances.

PRIOR ART

Tables 1, 2 and 3 below list the different approaches under development for obtaining living attenuated vaccines from wild hMPV strains.

Virus strains are considered as being attenuated in vitro when they exhibit decreased replicative capacity compared to the wild type (WT) virus, and/or when these virus strains lead to the more restricted formation of infectious outbreaks, notably of syncytia (adjacent cells fusing following viral infection). In vivo, attenuated virus strains replicate at a lower maximum load and/or induce less severe pathology (in terms of weight loss or inflammatory profile or histo-pathological damage) than the wild virus strain.

TABLE 1

List of living vaccine candidates attenuated on the basis of a strain of hMPV virus having one or more mutations, developed or under development

| Name of the virus | Description | Attenuation in vitro | Attenuation in vivo | Protective neutralising antibodies | Reference |
|---|---|---|---|---|---|
| cp-HMPV M11 (B1/NL/1/99) | Insertion of 11 mutations aa among the 17 induced by passages on Vero cells, temperature decreasing down to 25° C. | ✓ Vero > 39° C. | ✓ H | ✓ H | (Herfst, of Graaf et al. 2008) |
| cp-HMPV HRSV3 (B1/NL/1/99) | 4 mutations cp (cold passaging) of hRSV | ✓ Vero > 37° C. | ✓ H | ✓ H | (Herfst, of Graaf et al. 2008) |
| rhMPV-R329K rhMPV-D331A (A1/NL/1/00) | Mutations in the domain of link to the integrin of the F protein | ✓ LLC-MK2 | ✓ CR | ✓ CR | (Wei, Zhang et al. 2014) |
| HMPV M2 (A1/NL/1/00) | Deletion of the N-glycosylation site (aa 172) of the F protein | ✓ Vero. | ✓ M ✓ M SCID | ✓ M | (Yu, Li et al. 2012) (Liu, Shu et al. 2013) |
| HMPV-MTase (A1/NL/1/00) | Mutations of the methyltransferase site of L polymerase G1696A, G1700A, and D1755A | ✓ LLC-MK2 | ✓ CR | ✓ CR | (Zhang, Wei et al. 2014) |

The term "Vero" designates an African green monkey kidney cell line, widely used in cell culture for testing various viruses.
The term "LLC-MK2" designates a cell line derived from rhesus monkey kidney cells, used for tests of infection by various viruses.
The symbol ✓ indicates that the cells used are liable to viral infection.

The following abbreviations are used for the in vivo study models: M for Mouse; H for Hamster; CR for Cotton Rat; CM for Cynomolgus Macaque; AGM for African Green Monkey; Ch for Chimpanzee; Rh for Rhesus Monkey; and SCID for Severe Combined ImmunoDeficiency.

TABLE 2

List of attenuated living vaccine candidates developed or under development, comprising a hMPV virus strain having complete deletion of at least one gene

| Name of the virus | Description | Attenuation in vitro | Attenuation in vivo | Protective neutralising antibodies | References |
|---|---|---|---|---|---|
| HMPV-ΔSH (A2/CAN97-83) | Deletion of the SH gene | Ø LLC-MK2 | Ø H ✓ Ch | ✓ H ✓ Ch | (Biacchesi, Skiadopoulos et al. 2004) (Biacchesi, Pham et al. 2005) |
| HMPV-ΔG (A2/CAN97-83) | Deletion of the G gene | Ø LLC-MK2 | ✓ H at 3 days Ø H > 3 days ✓ Ch | ✓ H ✓ Ch | (Biacchesi, Skiadopoulos et al. 2004) (Biacchesi, Pham et al. 2005) |
| HMPV-ΔSH/ΔG (A2/CAN97-83) | Deletion of the SH and G genes | Ø LLC-MK2 | ✓ H at 3 days. Ø H > 3 days | ✓ H | (Biacchesi, Skiadopoulos et al. 2004) |
| HMPV- ΔM2-2 (A2/CAN97-83) | Mutations codon initiation + codon stop | Ø Vero | ✓ H ✓ Ch | ✓ H ✓ Ch | (Buchholz, Biacchesi et al. 2005) (Biacchesi, Pham et al. 2005) (Schickli, Kaur et al. 2008) |
| HMPV- ΔM2-1 (A2/CAN97-83) | Mutation codon stop | Ø Vero | Ø H | Ø H | (Buchholz, Biacchesi et al. 2005) |

TABLE 2-continued

List of attenuated living vaccine candidates developed or under development, comprising a hMPV virus strain having complete deletion of at least one gene

| Name of the virus | Description | Attenuation in vitro | Attenuation in vivo | Protective neutralising antibodies | References |
|---|---|---|---|---|---|
| HMPV- ΔM2-1/ ΔM2-2 (A2/CAN97-83) | Deletion of the complete M2 gene | Ø Vero | Ø H | Ø H | (Buchholz, Biacchesi et al. 20051 |

Δ: total deletion of the gene.
Ø = no attenuation or more replicative.
All the attenuated virus strains tested are derived from the wild strain CAN97-83 of the sub-group A2.

TABLE 3

List of attenuated living vaccine candidates developed or under development, based on a chimeric hMPV strain

| Name of the virus | Description | Attenuation in vitro | Attenuation in vivo | Protective neutralising antibodies | Clinical test | Ref. |
|---|---|---|---|---|---|---|
| HMPV-Pa (A2/CAN97-83) | hMPV virus genetic background (SH stabilised) Exchange of the P gene with the homologue aMPV C | Ø Vero | ✓ H ✓ AGM | ✓ H ✓ AGM | Phase 1 NCT01255410 | (Pham, Biacchesi et al. 2005) (Karron, San Mateo et al. 2017) |
| HMPV Na (A2/CAN97-83) | hMPV virus genetic background (SH stabilised) Exchange of the N gene with the homologue aMPV C | Ø Vero | ✓ H at 3 days. Ø H > 3 days ✓ AGM | ✓ H ✓ AGM | | (Pham, Biacchesi et al. 2005) |
| b/hPIV3/ hMPV F2 (A1/NL/1/00) | Bovine PIV-3 genetic background Exchange of the F and HN genes with their homologue hPIV-3 Addition F hMPV in 2$^{nd}$ position on the genome | — | Ø H Ø AGM ✓ Rh seronegative | ✓ H ✓ AGM (hMPV/hPIV) | | (Tang, Schickli et al. 2003) (Tang, Mahmood et al. 2005) |
| SeV-MPV-Ft (A2/CAN00-16) | SeV genetic background Addition F gene hMPV truncated for its TM domain | — | ✓ CR | ✓ CR | | (Russell, Jones et al. 2017) |

The following abbreviations are used: TM = transmembrane domain; PIV = Parainfluenza Virus; SeV = Sendai Virus.

The international application WO 2005/014626 relates to several strains of hMPV, designated by the following denominations: CAN 97-83, CAN 98-75 and HMPV 00-1. This application describes a strain of recombinant hMPV, designated CAN 97-83, genetically modified to attenuate its virulence. The modifications proposed notably relate to the total deletion of the genes encoding for the G and/or SH proteins. The modified virus strains may be used in human therapy, for preventing or treating infections with pneumoviruses. The administration of the wild strain or of these attenuated strains to hamsters makes it possible to protect them against later infection by a CAN 97-83 hMPV. However, WO 2005/014626 makes no mention of complete protective properties, in particular no weight monitoring of the treated animals is carried out. The same experimental results are described in the scientific articles cited in table 2.

With the same attenuated strains, in vivo results were next obtained on a monkey animal model; the recombinant virus strains deleted of SH, G and M2-2 genes continue to replicate in the respiratory tracts of the monkeys; and furthermore induce the production of neutralising antibodies just like the CAN97-83 wild virus strain.

Other isolated hMPV strains have been described in the U.S. Pat. No. 8,841,433, the use thereof for the preparation of vaccines also being proposed.

Vaccines based on the use of attenuated living virus strains have numerous advantages.

On the one hand, vaccines produced from attenuated living viruses have the advantage of inducing a strong immune response from a virus of which the capacity to multiply is considerably reduced, thus making it possible to avoid the occurrence of the pathology while mimicking the natural infection. During the development of these attenuated strains, it is important to find the ideal balance between attenuation and immunogenicity.

On the other hand, these vaccines may be administered by intra-nasal route, and thus mimic the natural entry route of wild viruses, thus inducing an immune response quite similar to the physiological response to an infection.

In addition, this vaccination strategy does not generate an exaggerated inflammatory reaction, as may be the case with inactivated vaccines. Finally, the addition of adjuvant is generally not necessary.

It is thus the optimal vaccinal strategy for prevention in populations at risk such as young children and infants.

DESCRIPTION OF THE INVENTION

The subject-matter of the invention is an attenuated virus strain derived from a particular clinical strain rC-85473 of human metapneumovirus, comprising the genome sequence represented by sequence SEQ ID NO. 1, said attenuated strain comprising one or more genetic modifications of said sequence SEQ ID NO.1 attenuating the virulence of said strain.

The attenuated virus strains according to the invention are notably recombinant strains modified by inactivation or deletion of at least one gene encoding for one of the G and SH accessory proteins, to generate recombinant viruses designated ΔG rC-85473 and ΔSH rC-85473, respectively.

More specifically, the subject-matter of the present invention is an attenuated virus strain derived from a clinical strain of human metapneumovirus, comprising the genome sequence represented by sequence SEQ ID NO. 1, said attenuated strain comprising at least one genetic modification selected from: inactivation of the gene encoding for the accessory G protein, and inactivation of the gene encoding for the accessory SH protein.

These strains were characterised with respect to their infectivity and their viral replication in in vitro (LLC-MK2 cell line) and ex vivo (reconstituted human respiratory epitheliums, cultured at the air-liquid interface) cell models, as well as with respect to viral pathogenesis and their property of vaccinal protection in a murine infection model by hMPV.

The results presented in the experimental section highlight the specific properties of these virus strains ΔG rC-85473 and ΔSH rC-85473, in comparison with those of virus strains modified in a similar manner, also deleted of G or SH genes, but derived from another clinical strain of hMPV (CAN98-75).

The viruses ΔG or ΔSH rC-85473 have in particular:
(i) an attenuated viral character in a murine model, unlike the recombinant virus ΔSH CAN98-75 which is very virulent for its part;
(ii) while conserving their replication capacity in binding cell systems (reference line LLC-MK2) and in suspension, unlike the recombinant viruses CAN98-75 which are much less productive;
(iii) the viruses ΔG or ΔSH C-85473 advantageously have significant protective properties: 100% survival of infected mice, little weight loss, induction of a neutralising antibody response against the homologous virus strain (C-85473, serotype A) and at least against one heterologous strain (CAN98-75, serotype B), as well as reduced pulmonary pathogenesis in the infected animals, vis-à-vis an infectious challenge by a wild hMPV (strain rC-85473), which causes 50% lethality in the non-immunised control groups.

This attenuated virus strain may be used in vivo, ex vivo and in vitro as an expression vector of at least one exogenous gene, in particular a gene encoding for a viral antigen and, above all, viral antigens derived from the human respiratory syncytial virus (hRSV) and in particular its F fusion protein.

The invention also relates to this attenuated virus strain for the use thereof as a medicine, and more particularly for preventing and/or treating infections by viruses of the Pneumoviridae family.

Finally, the invention also relates to a vaccine composition comprising, in a pharmaceutically acceptable vehicle, at least one attenuated virus strain such as defined above, and optionally an adjuvant.

DESCRIPTION OF THE FIGURES

FIG. 1. Recombinant hMPVs generated from the clinical strains C-85473 and CAN98-75.

FIG. 1A Schematic representation of the genome of the recombinant viruses generated by reverse genetics from the clinical strain C-85473, and in which has been cloned the GFP (Green Fluorescent Protein) coding sequence at its end 3'. The virus rC-85473 contains the genome of the wild strain C-85473 expressing in addition the GFP gene. The genomes of the recombinant viruses derived from the strain C-85473 and deleted of SH (ΔSH-rC-85473) or G (ΔG-rC-85473) genes are represented below. The genetically modified viruses are functional and replicative, such as indicated by the images of LLC-MK2 cells infected with a Multiplicity of Infection (MOI) of 0.01 by these viruses, and observed by fluorescence microscopy at three days post-infection.

FIG. 1B Schematic representation of the genome of the recombinant viruses generated by reverse genetics from the clinical strain CAN98-75, and in which has been cloned the GFP (Green Fluorescent Protein) coding sequence. The virus rCAN98-75 contains the genome of the wild strain CAN98-75 expressing in addition the GFP gene at its end 3'. The genomes of the recombinant viruses derived from the strain CAN98-75 and deleted of SH (ΔSH-rCAN98-75) or G (ΔG-rCAN98-75) genes are represented below. The genetically modified viruses are functional and replicative, such as indicated by the images of LLC-MK2 cells infected with 0.01 MOI by these viruses and observed with fluorescence microscopy at three days post-infection.

FIG. 2. In vitro replicative capacities of the virus strains rC-85473 and rCAN98-75 and strains derived therefrom.

p<0.01 and *, p<0.001 (Two-way ANOVA statistical tests).

FIG. 3: In vivo characterisation of the recombinant hMPVs rCAN98-75 and rC-85473 by infection of BALB/c mice: weight curves, and pulmonary viral loads at 5 days post-infection.

FIG. 3A BALB/c mice were infected by intranasal instillation with OptiMem culture medium ("mock" negative control, black triangles) or $2.5\times10^5$ FFU of the recombinant viruses rCAN98-75 (black circles), ΔSH-rCAN98-75 (grey squares) and ΔG-rCAN98-75 (grey triangles). The weight and survival of the mice was monitored daily for 14 days.

FIG. 3B 5 days after infection, 5 mice per group (except negative control group) underwent euthanasia for a measurement of pulmonary infectious viral loads of TCID50/gramme of lung.

FIG. 3C BALB/c mice were infected by intranasal instillation with OptiMem culture medium ("mock" negative control, black diamonds) or $5\times10^5$ TCID50 of the recombinant viruses rC-85473 (black circles), ΔSH-rC-85473 (grey squares) and ΔG-rC-85473 (grey triangles). The weight and the survival of the mice was monitored daily for 14 days.

FIG. 3D 5 days after infection, 5 mice by group (except negative control group) underwent euthanasia for a measurement of pulmonary infectious viral loads of TCID50/gramme of lung.

Statistical tests: Two-way ANOVA tests to compare each virus with the "mock" condition. *, $p<0.05$,  $p<0.01$ and *, $p<0.001$.

FIG. 4: In vivo protective properties of the recombinant hMPVs ΔG-rC-85473 and ΔSH-rC-85473 in a BALB/c murine infectious challenge model.

FIG. 4A Diagram of the immunisation protocol (top) followed by the infectious challenge protocol (bottom). The lethal dose corresponds to $1\times10^6$ $TCID^{50}$.

FIG. 4B Infectious challenge of mice immunised with the virus strains rC-85473 (black circles), ΔSH-rC-85473 (grey squares) or ΔG-rC-85473 (grey triangles), or non-immunised ("mock", black triangles)

21 days after immunisation, the mice were infected by intranasal instillation with a lethal dose ($1\times10^6$ $TCID^{50}$) of the wild virus rC-85473. Their weight was monitored daily for 14 days.

FIG. 4C Post-challenge survival curves of the mice of the different groups of immunised mice.

The "mock" non-immunised mice have only 50% survival; those immunised by the recombinant viruses rC-85473, ΔSH-rC-85473 or ΔG-rC-85473 have 100% survival.

FIG. 4D 5 days after the infectious challenge (i.e. at day 26 post-immunisation), 4 mice of each group underwent euthanasia to measure their pulmonary infection viral loads of TCID50/g of lung. "nd" signifies non-detectable.

FIG. 4E 5 days after the infectious challenge (i.e. at day 26 post-immunisation), 4 mice of each group underwent euthanasia to measure their pulmonary infection viral loads by RTqPCR (N gene).

Statistical tests: Two-way ANOVA to compare each virus with the mock condition. *, $p<0.05$,  $p<0.01$ and *, $p<0.001$.

FIG. 5: In vitro cell binding capacities of the recombinant viruses rC-85473 and rCAN98-75 and deleted versions thereof.

FIG. 5A Percentage of infected LLC-MK2 cells as a function of binding time, with the virus rCAN98-75 (circles) and the attenuated forms thereof ΔSH-rCAN98-75 (squares) and ΔG-rCAN98-75 (triangles).

FIG. 5B Percentage of infected LLC-MK2 cells as a function of binding time, with the virus rC-85473 (circles) and the attenuated forms thereof ΔSH-rC-85473 (squares) and ΔG-rC-85473 (triangles).

FIG. 6: Ex vivo replicative capacities of the recombinant viruses rC-85473 and rCAN98-75 on a reconstituted human respiratory epithelium 3D model and cultured at the air-liquid interface.

FIG. 6A The human respiratory epithelium models in culture were infected with the recombinant viruses rCAN98-75, ΔSH-rCAN98-75 and ΔG-rCAN98-75 (photos of the upper line) or with the recombinant viruses rC-85473 (white), ΔSH-rC-85473 (dark grey) and ΔG-rC-85473 (not determinable) (photos of the lower line).

FIG. 6B Quantification of the measured viral progeny (via the quantification of viral genome) at the apical surface of epitheliums infected with the recombinant viruses rCAN98-75 (WT, white), ΔSH-rCAN98-75 (dark grey) and ΔG-rCAN98-75 (light grey) (left of the dotted line) or with the recombinant viruses rC-85473 (WT), ΔSH-rC-85473 and ΔG-rC-85473 (right of the dotted line).

FIG. 6C Quantification of the viral genome present within epitheliums infected with the recombinant viruses rCAN98-75 (WT, white), ΔSH-rCAN98-75 and ΔG-rCAN98-75 (left of the dotted line) or with the recombinant viruses rC-85473 (WT, white), ΔSH-rC-85473 and ΔG-rC-85473 (right of the dotted line).

FIG. 7. Secretion of cytokines and chemokines induced by infection with the recombinant viruses rC-85473 on a reconstituted human respiratory epithelium 3D model and cultured at the air-liquid interface.

Reconstituted human respiratory epitheliums (MucilAir® HAE, Epithelix) were infected with the recombinant viruses rC-85473, ΔSH-rC-85473 and ΔG-rC-85473 at a MOI of 0.1. After 5 days of infection, the quantity of several cytokines and chemokines is measured by the Luminex technique (BioPlex Pro kit assay, BioRad) from the basal medium of the infected epitheliums:

FIG. 7A Chemokines MCP-1, IP-10, RANTES, IL-8, T lymphocyte attracting G-CSF, monocytes/macrophages, eosinophils and/or neutrophils.

FIG. 7B Quantification of pro-inflammatory Cytokines IFN-γ and TNF-α.

FIG. 7C Quantification of Cytokine IL-7, stimulating the differentiation of T and B lymphocytes.

FIG. 7D Growth factor FGF, involved in tissue repair.

Statistical tests: One-way ANOVA to compare the viruses ΔSH-rC-85473 and ΔG-rC-85473 with the virus rC-85473. *, $p<0.05$,  $p<0.01$ and *, $p<0.001$.

FIG. 8. In vitro viral-induced secretion of the pro-inflammatory cytokines IL-1β and TNF-α in a model of immortalised murine macrophages infected by the recombinant hMPVs rC-85473.

FIG. 8A Evaluated viral load in FFU/ml in the cell supernatants collected each day for the 2 days following infection of an immortalised murine macrophage cell line (BMDM line derived from the bone marrow of wild mice), by the recombinant viruses rC-85473 (black), ΔSH-rC-85473 (dark grey) or ΔG-rC-85473 (light grey) at a MOI of 0.1.

FIG. 8B Quantity of the pro-inflammatory cytokine TNF-α evaluated by ELISA test from the cell supernatants collected each day for the 2 days following infection of immortalised murine macrophage, by the recombinant viruses rC-85473 (black), ΔSH-rC-85473 (dark grey) or ΔG-rC-85473 (light grey) at a MOI of 0.1, in comparison with non-infected "mock" immortalised murine macrophages (white).

Figure 8C:
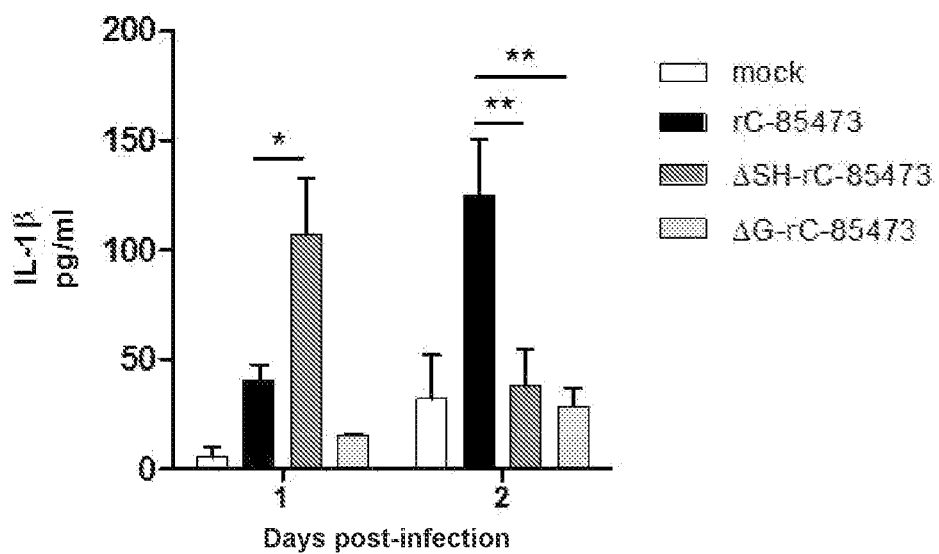

FIG. 8C Quantity of the pro-inflammatory cytokine IL-1β evaluated by ELISA test from the cell supernatants collected each day for the 2 days following infection of immortalised murine macrophages by the recombinant viruses rC-85473 (black), ΔSH-rC-85473 (dark grey) or ΔG-rC-85473 (light grey) at a MOI of 0.1, in comparison with non-infected "mock" immortalised murine macrophages (white).

Statistical tests: Two-way ANOVA to compare the viruses ΔSH-rC-85473 and ΔG-rC-85473 with the virus rC-85473. *, p<0.05 and ** p<0.01.

FIG. 9. Pulmonary inflammation and recruitment of immune cells on the site of the infection in vivo, 5 days after infection of BALB/c mice by the recombinant hMPVs rC-85473, ΔSH-rC-85473 and ΔG-rC-85473 (pulmonary inflammation uniquely for ΔG-rC-85473).

Figure 9A:
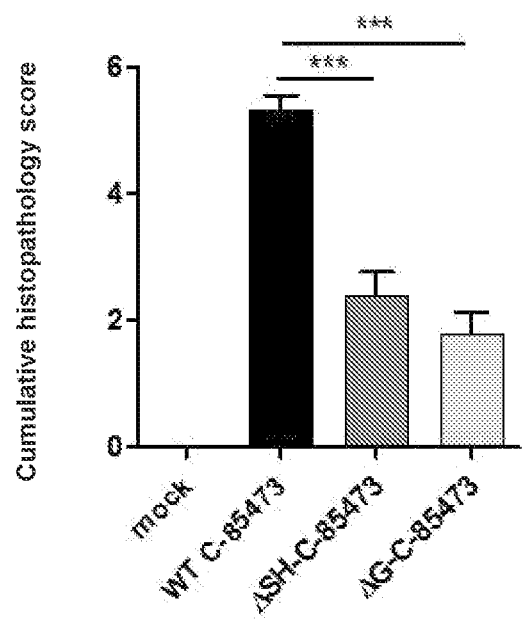

FIG. 9A Cumulative pulmonary histopathology score, calculated according to an evaluation of the intensity of the inflammation of the bronchial/endobronchial, peribronchial, perivascular, interstitial, pleural and intra-alveolar tissues of the lungs of BALB/c mice infected by the viruses rC-85473 (black), ΔSH-rC-85473 (dark grey), ΔG-rC-85473 (light grey) or "mock" non-infected, said tissues being collected and fixed with formaldehyde 5 days after viral infection.

Figure 9B:
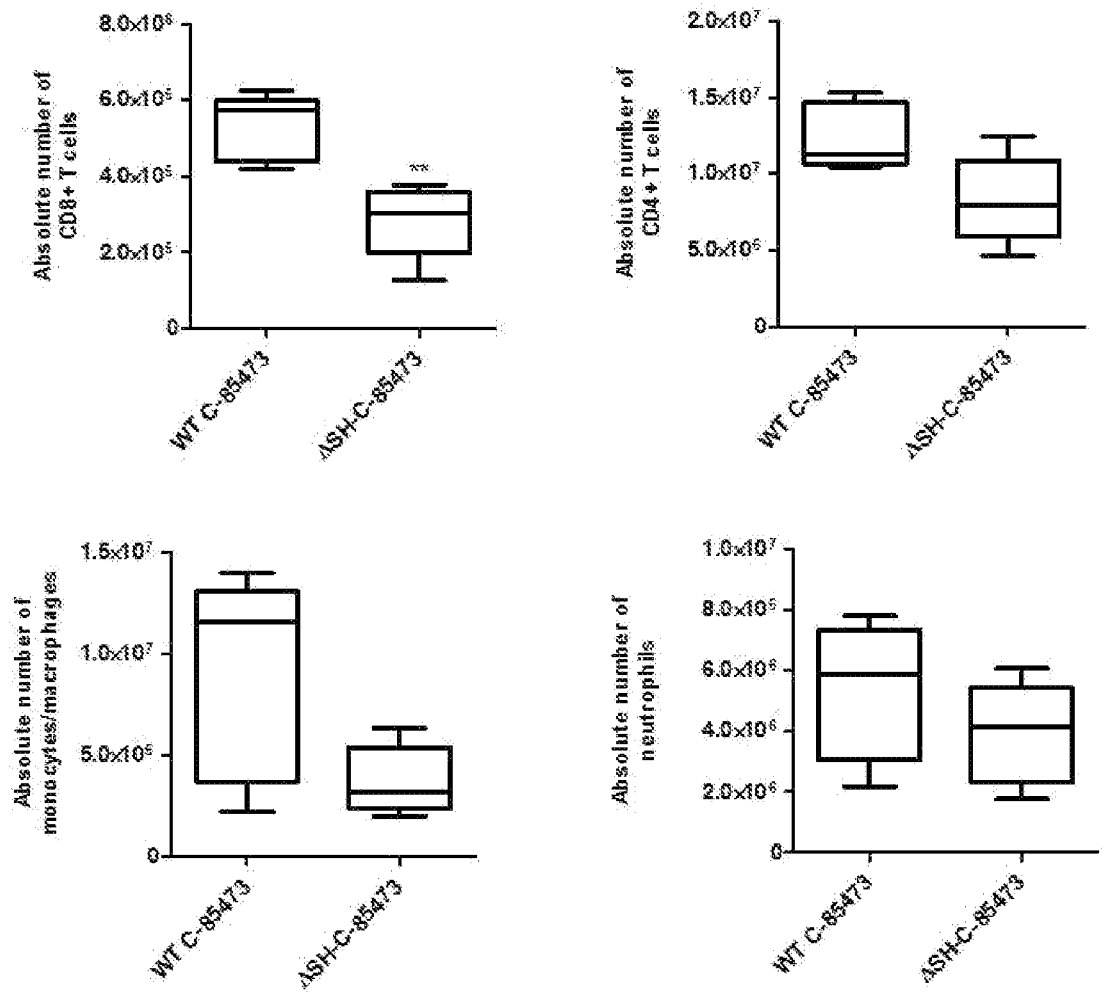

FIG. 9B Phenotyping of immune cells determined by immuno-labelling (anti-CD45, anti-CD11b, anti-CD170, anti-Ly6C, anti-Ly6G, anti-CD11c, anti-CD115, anti-B220, anti-CD3c, anti-CD4, anti-CD8a) by flow cytometry, from lysates of lungs of BALB/c mice infected by the viruses rC-85473 and ΔSH-rC-85473, after 5 days of infection. The recruited immune cells are classified into four categories: CD8+T lymphocytes (CD8+ T cells), CD4+T lymphocytes (CD4+ T cells), monocytes/macrophages, and neutrophils.

Statistical tests: One-way ANOVA to compare the viruses ΔSH-rC-85473 and ΔG-rC-85473 with the virus rC-85473.  p<0.01 and *, p<0.001.

FIG. 10. Characterisation of the in vivo secondary immune response in a BALB/c murine model immunised by the recombinant hMPVs ΔG-C-85473 and ΔSH-C-85473, following an infectious challenge.

Figure 4A:
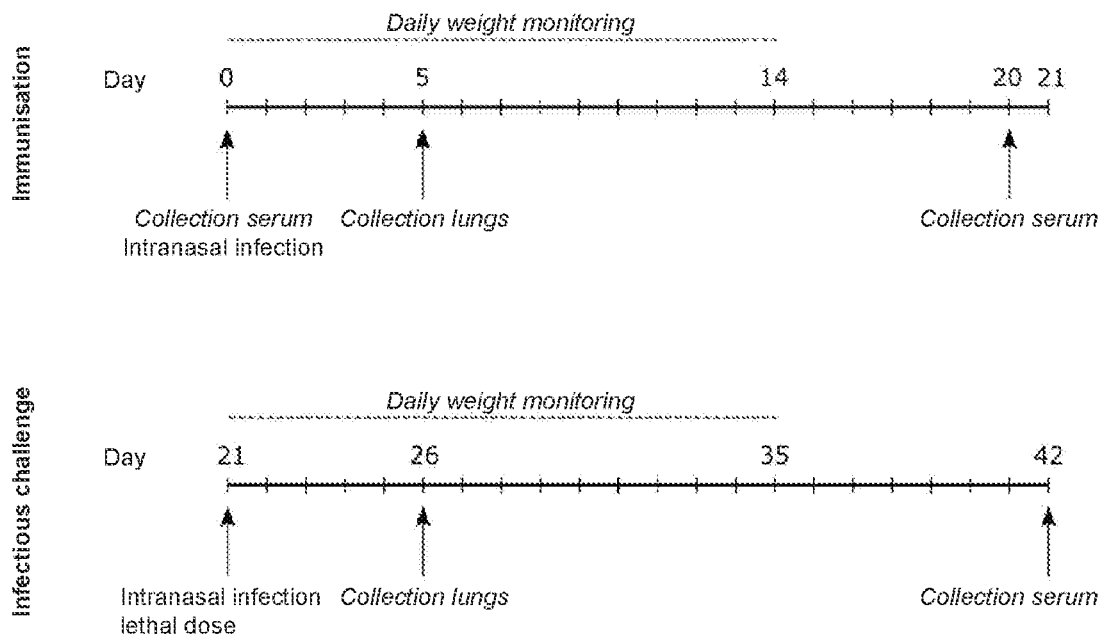
Figure 4B:
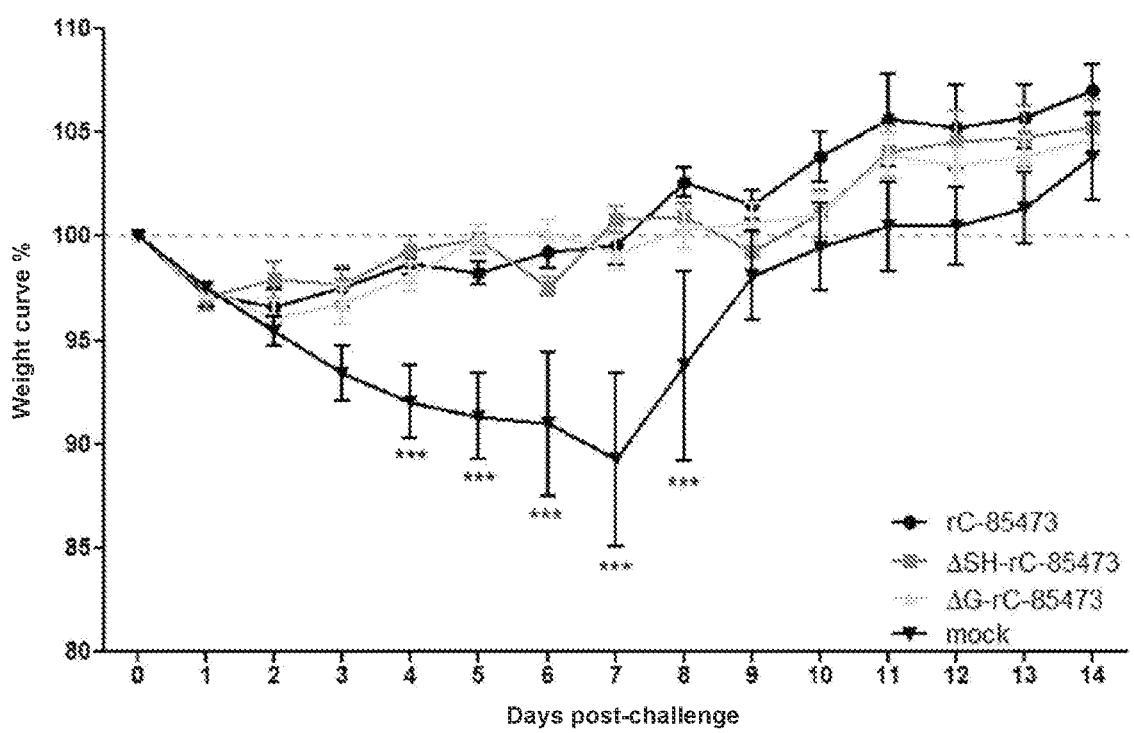
Figures 10A, 10B:
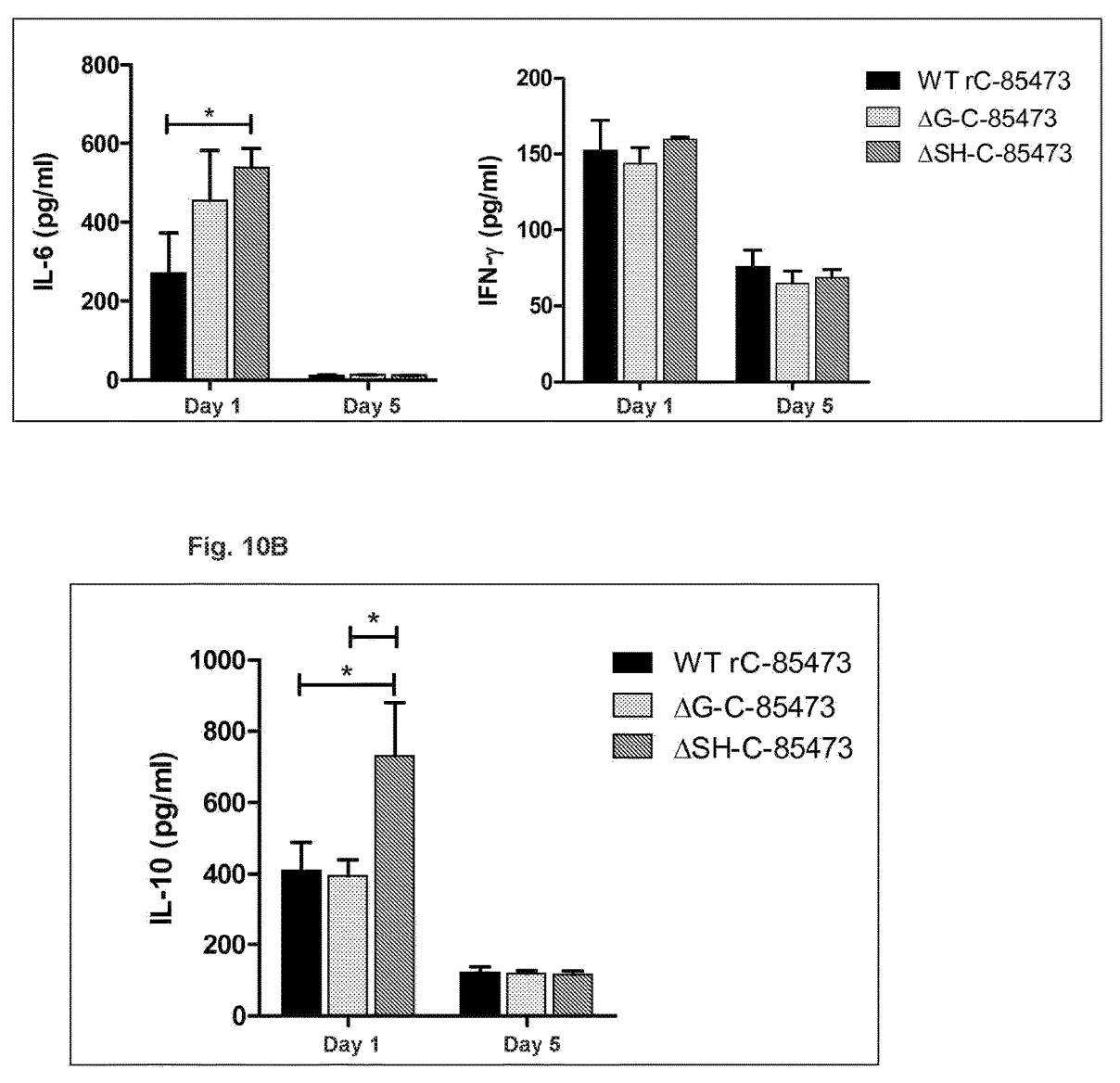
Figure 10C:
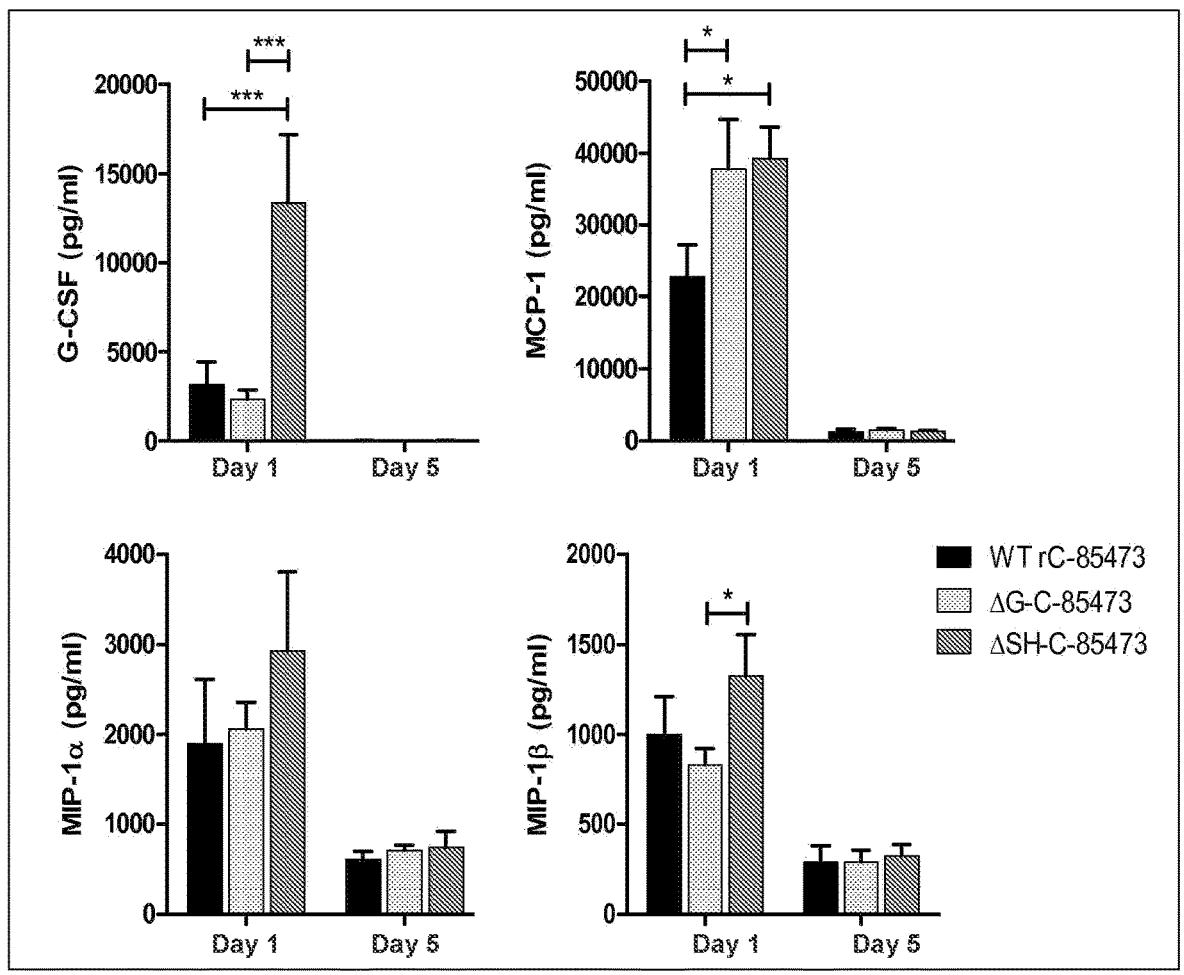
Figure 10D:
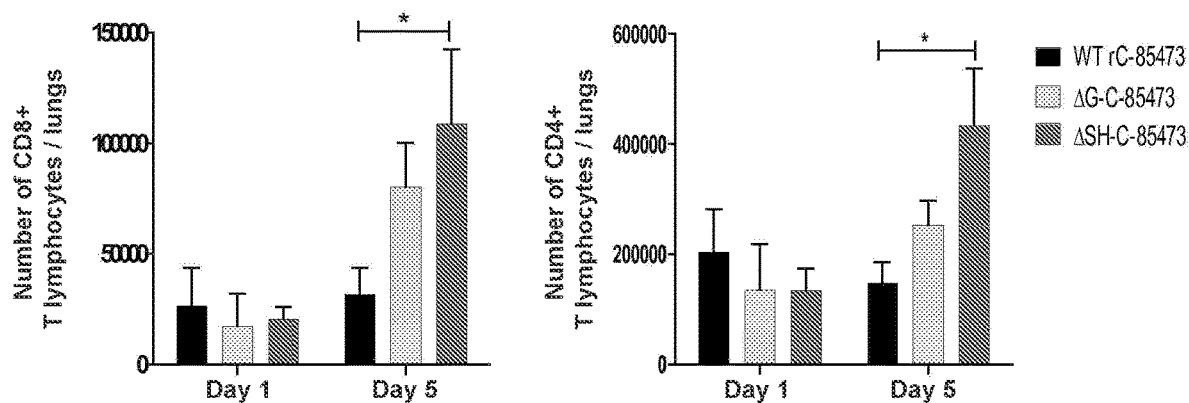
Figure 10E:
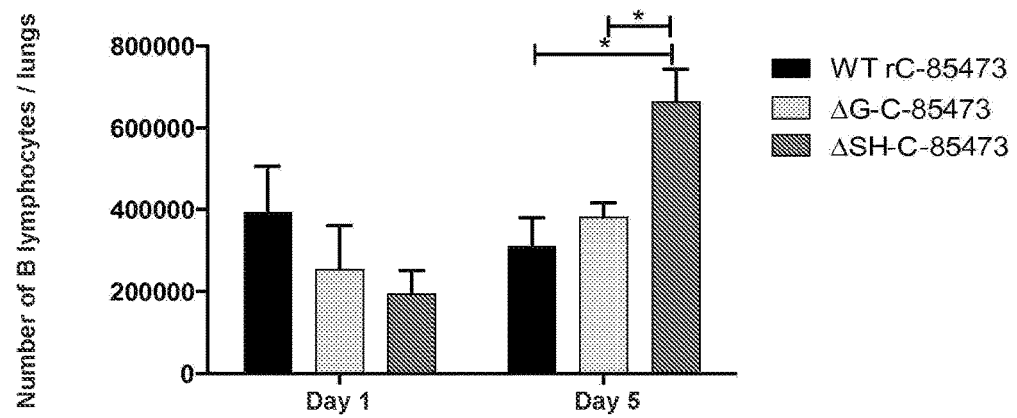
Figure 10F:
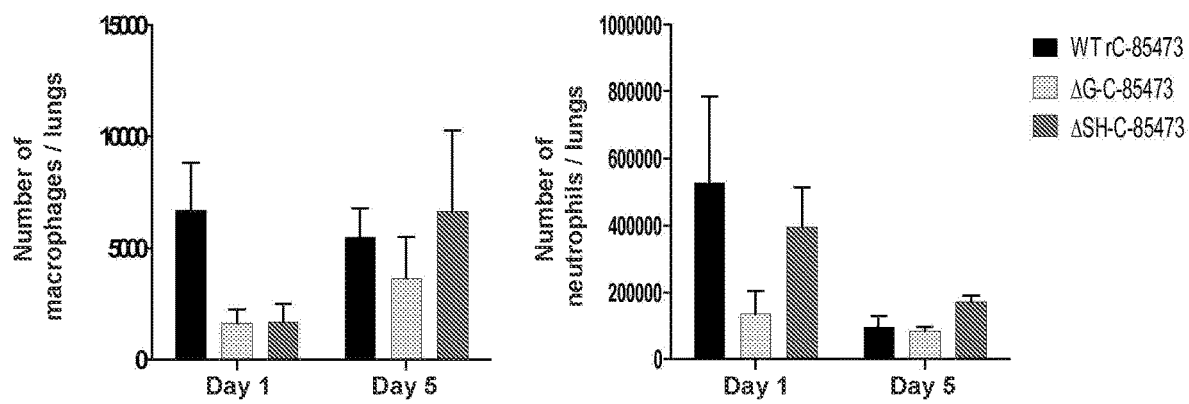
Figure 10G:
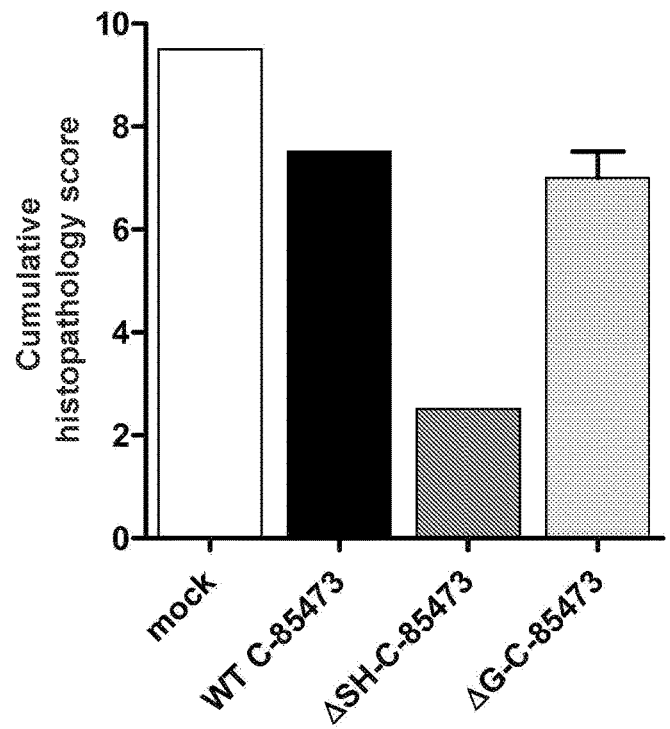

1 and/or 5 days after infectious challenge by the virus WT rC-85473 such as described in FIG. 4A, the quantity of several cytokines and chemokines is measured by the Luminex technique (BioPlex Pro kit assay, BioRad) from lung lysates [FIG. 10A-C]; the phenotyping of the immune cells infiltrated into the pulmonary tissue is determined by immuno-labelling (anti-CD45, anti-Ly6G, anti-CD11 b, anti-CD170/Siglec-F, anti-Ly6C, anti-CD11c, anti-F4/80, anti-B220, anti-CD3c, anti-CD4 and anti-CD8a) by flow cytometry, from lung lysates [FIG. 10D-F]; and the cumulative pulmonary histopathology score is calculated according to an evaluation of the intensity of the inflammation of the bronchial/endobronchial, peribronchial, perivascular, interstitial, pleural and intra-alveolar tissues of the lungs of the mice fixed with formaldehyde [FIG. 10G].

In FIGS. 10A to 10G are represented:
in black, the group of BALB/c mice having been immunised by the virus rC-85473;
in dark grey, the group immunised by the virus ΔSH-C-85473;
in light grey, the group immunised by the virus ΔG-C-85473;
and, if represented, in white the so-called "mock" non-immunised group.

N=2 or 3 mice/group, respectively for the histopathological or secretion of cytokines/cell recruitment analyses.

Statistical tests: Two-way ANOVA to compare each group with each other *, p<0.05,  p<0.01 and *, p<0.001.

FIG. 10A Quantification of the pro-inflammatory cytokines IL-6 and IFN-γ, after 1 and 5 days of infectious challenge.

FIG. 10B Quantification of the anti-inflammatory cytokine IL-10, after 1 and 5 days of infectious challenge.

FIG. 10C Quantification of the attracting chemokines G-CSF, MCP-1, MIP-1α and MIP-1β and stimulating the activation and the differentiation of immune cells, after 1 and 5 days of infectious challenge.

FIG. 10D Quantification of CD8+ and CD4+T lymphocytes infiltrated into the pulmonary tissue of the BALB/c mice, after 1 and 5 days of infectious challenge.

FIG. 10E Quantification of the B lymphocytes infiltrated into the pulmonary tissue of the BALB/c mice, after 1 and 5 days of infectious challenge.

FIG. 10F Quantification of the macrophages and neutrophils infiltrated into the pulmonary tissue of the BALB/c mice, after 1 and 5 days of infectious challenge.

FIG. 10G Cumulative pulmonary histopathology score, after 5 days of infectious challenge.

DETAILED DESCRIPTION OF THE INVENTION

Human Metapneumovirus (hMPV) Virus Strains hMPVs were identified in 2001 as forming part of the Pneumoviridae family.

The genomic organisation of the hMPV is analogous to the hRSV. It is sub-divided into several ORFs (Open Reading Frames) encoding for N, P, M, F, M2 (M2-1 and M2-2), SH, G and L proteins. The general genome structure is represented for the viruses rC-8543 and rCAN98-75 in FIGS. 1A and 1B.

Member viruses of the Pneumoviridae family express at their surface three glycoproteins designated F, G and SH proteins.

The F fusion glycoprotein, highly conserved between the different hMPV sub-groups, is involved in the penetration of the virus into the target cells, and the formation of syncytium, that is to say large multi-nucleated cells derived from the fusion of individual cells following their infection by the virus. The F glycoprotein is also considered as being the major antigen of the viruses hRSV and hMPV, making it possible to induce the production of neutralising antibodies.

The G protein is a type II membrane protein, its C-terminal end being outside of the cell. This protein is non-essential for the assembly of the viral constituents, and for replication in vitro. For hRSV, it has been shown that the deletion of the gene encoding this protein attenuated the virulence of the strain during infection of the respiratory tracts of mice.

The SH protein is also a type II membrane protein, the function of which in the viral cycle is still unknown. In the case of hRSV, the deletion of the gene encoding for the SH protein generates a recombinant virus capable of reproducing in vitro, and the virulence of which is attenuated in the upper respiratory tract of mice, but not in the lower part of said tract.

Genetic analysis of clinical hMPV strains has made it possible to define two major groups (serotypes A and B) and four "minor" sub-groups (A1, A2, B1 and B2), mainly based on the variability of the sequence of surface binding (G) and fusion (F) glycoproteins. It was next shown that these groups could again be sub-divided into sub-lines such as A2a and A2b (Huck et al., 2006).

Among widely studied virus strains may be cited the strain NL 00-1, belonging to the serotype A1; the strain CAN 97-83 belonging to the serotype A2; and the strain CAN 98-75, belonging to the serotype B2.

The present invention is based on a virus strain of human metapneumovirus, designated rC-85473, isolated from a patient sample in Canada, notably referenced in the article (Hamelin et al., 2010).

The use of the F protein of this strain, in combination with the M protein, has been proposed as a vaccinal strategy (Aerts et al., 2015a).

The use of this virus strain rC-85473, inactivated by treatment with formalin, as inactivated living vaccine strain, has been described in the article (Palwithino et al., 2015). A heat inactivated version of the strain rC-85473 has also been tested (Hamelin et al., 2007).

More recently, the strong fusion capacities of this strain have been studied in detail, on the basis of the protein sequence of its F protein (Dubois et al., 2017).

The sequence of the F gene and the M gene of the strain rC-85473 are referenced in GenBank, respectively with the access numbers KM408076.1 and KM408077.1.

The complete genome sequence of this virus strain rC-85473, comprising 13394 nucleotides, is here disclosed for the first time: it is represented in the appended list of sequences, under the reference SEQ ID NO. 1.

Table 4 below shows the identity percentage of this strain rC-85473 with three other virus strains of human metapneumovirus: CAN 97-83, CAN 98-75 and NL 00-1.

According to a preferred embodiment of the present invention, the peptide sequence of the F protein of the attenuated virus strain derived from the strain rC-85473 is not modified, and is thus identical to the peptide sequence of the F protein of the strain rC-85473 such as described in (Dubois et al., 2017).

Reverse Genetics Technology

Reverse genetics technology makes it possible to create, from a nucleic acid sequence, DNA or RNA, and from appropriate host cells, a functional encapsidated virus.

The recombinant strain rC-85473 of human metapneumovirus was thus obtained from a clinical strain designated C-85473, isolated in a patient.

The first reverse genetics system applied to the hMPV was described in 2004 (Biachesi et al., 2004). This technology is also described in the article (Aerts et al., 2015b).

The principle of this technology, which enables the production of recombinant hMPVs, is based on the use of a hamster kidney cell line (BHK-21) modified to express constitutively the RNA polymerase of the T7 bacteriophage (BHK-T7 or BSR-T7/5 cells).

The genome elements are distributed in five plasmid elements: A plasmid encoding the antigenome of hMPV and 4 "satellite" plasmids, encoding for the viral proteins of the transcription machinery (L, P, N and M2-1).

After co-transfection of the antigenomic plasmid hMPV and the four "satellite" plasmids in these cells, an RNA strand corresponding to the viral genomic strand (negative RNA strand), is transcribed by the T7 polymerase from its promoter.

The four proteins involved in the viral transcription of hMPV are also expressed by the transfected host cells to constitute an active RNA-dependent RNA polymerase (RdRP) complex. This functional viral polymerase thus transcribes the genomic RNA into viral mRNA then replicates it into new molecules of viral genomic RNA, via the transcription of matrix strands.

TABLE 4

Nucleotide sequence identity percentage for each ORF (the identity of the sequence of amino acids is indicated in brackets) between the virus rC-85473 and other hMPVs

| ORF | N | P | M | F | M2-1 | M2-2 | SH | G | L |
|---|---|---|---|---|---|---|---|---|---|
| CAN97-83 (A2) | 94 (99) | 91 (95) | 93 (99) | 94 (98) | 94 (96) | 94 (94) | 90 (85) | 81 (68) | 94 (98) |
| CAN98-75 (B2) | 86 (96) | 81 (85) | 85 (97) | 84 (94) | 85 (94) | 85 (88) | 70 (61) | 56 (39) | 84 (93) |
| NL 00-1 (A1) | 98 (99) | 97 (98) | 98 (99) | 97 (99) | 98 (98) | 98 (97) | 97 (96) | 93 (89) | 98 (99) |

With regard to the high sequence homology observed with the strain NL 00-1, it may be concluded that this strain rC-85473 is member of the sub-group A1.

The strain rC-85473 is characterised by considerable fusogenic capacities, enabling it to penetrate into target cells at a high frequency/a high degree of infection. This considerable fusogenic capacity of this strain makes it possible to generate particularly elongated syncytia.

Syncytia are giant multinucleated cells. The virus rC-85473 has a high capacity of inducing cell fusion in vitro, leading to the formation of these very elongated syncytia, constituted of a very large number of cell nuclei.

It has been shown that 5 amino acids of the HRA functional domain of the F protein, amino acids unique among the other known hMPV strains, are in part responsible for this hyperfusogenic phenotype (Aerts et al., 2015b; Dubois et al., 2017).

According to a preferred embodiment of the present invention, the peptide sequence of the F protein of the attenuated virus strain derived from the strain rC-85473 comprises these 5 amino acids of the HRA functional domain such as described in (Dubois et al., 2017).

The translation and the assembly of viral proteins with genomic RNA thus enable the budding of infectious hMPV particles from the cytoplasmic membrane of transfected BHK-T7 cells. Next, amplification of the recombinant viruses is enabled thanks to the addition in co-culture of LLC-MK2 cells (ATCC CCL-7), permissive to infection.

Thus, from a genome sequence of a particular virus strain, it is possible to produce recombinant viruses thanks to these modified cells, which are commercially available.

Attenuated Virus Strain Derived from the Strain rC-85473

The present invention relates to an attenuated virus strain derived from a human metapneumovirus strain comprising the genome sequence represented by sequence SEQ ID NO. 1, said attenuated strain comprising one or more genetic modifications of said sequence SEQ ID NO. 1 attenuating the virulence of said strain.

In the present application, the terms "a virus" and "a virus strain" are used indiscriminately to designate a particular virus strain, such as identified previously.

In the sense of the invention, "derived strain" is taken to mean a recombinant virus strain obtained by the introduction of genetic modifications into the genome of a so-called "original strain" virus strain. The original strain is advantageously a wild strain, for example a clinical isolate.

The genetic modifications introduced into the original strain all have the object of attenuating the virulence of said original strain, and not of modifying the identity of its genome.

In particular, these genetic modifications only concern genes encoding for proteins non-essential for the replication of the virus, in other words "accessory proteins", such as SH and G proteins. In this genetically modified attenuated strain, the peptide sequence of the F protein of the original strain rC-85473 is not modified, and thus has the same peptide sequence as the original strain.

The virulence of a virus strain corresponds to the degree of rapidity of multiplication of a virus in a given organism, thus to its invasion rate. "Attenuating the virulence" is thus taken to mean decreasing the invasion rate of a virus in an organism.

This attenuation may take the form of a decrease in the replication capacities of the virus strain, and/or a decrease in its capacity to infect target cells, and/or instead a decrease in the pathology induced by the viral infection of the organism.

Thus, "attenuated virus strain" is taken to mean, in the sense of the invention, a recombinant virus, the virulence of which is decreased compared to that of the original virus strain, that is to say less than that of the original virus strain.

To measure the virulence of a virus strain, in vitro, ex vivo or in vivo tests may be carried out, such as for example in vitro replicative capacity tests (measured by TCID50/ml titration or quantitative PCR), monitoring by microscopic observation of the evolution of in vitro and ex vivo cytopathic effects, or monitoring of the clinical signs of the pathology, pulmonary histopathological observation and measurement of pulmonary viral loads in an in vivo infection model.

To compare the physiological effects of a wild strain and an attenuated strain, it is also possible to measure/determine different physiological parameters modified at the level of the lung and/or other immune systems of a host organism of the virus.

As is described in examples 7, 8 and 9 of the present application, the following viral-induced effects may be evaluated to compare the physiological effects of attenuated virus strains, either compared with each other or with the wild virus strain:

The secretion of pro-inflammatory cytokines (by the cells of the epithelium and/or by the macrophages);
The secretion of chemokines;
The secretion of growth factors;
The level of pulmonary inflammation (score calculated by evaluation of the intensity of inflammation of the tissues); and
The phenotyping of immune cells recruited on the site of the infection in vivo.

These various measurements make it possible to know in a more precise manner the physiological effect of each virus strain, and to choose as a function of these characteristics which would be the most suited for developing an attenuated living virus vaccine.

Genetic Modifications Introduced into a Virus Strain to Obtain the Attenuation Thereof The present invention relates to an attenuated virus strain derived from a human metapneumovirus strain comprising the genome sequence represented by sequence SEQ ID NO. 1, said attenuated strain comprising one or more genetic modifications of said sequence SEQ ID NO. 1 attenuating the virulence of said strain.

"Genetic modifications attenuating the virulence of said strain" is taken to mean genetic modifications relative to genes encoding for proteins non-essential for the replication of the virus, well known to the person skilled in the art. Among these proteins, G and SH proteins, described above, are notably known.

In other words, the present application relates to an attenuated virus strain derived from a human metapneumovirus strain comprising the genome sequence represented by sequence SEQ ID NO. 1, said attenuated strain having been genetically modified to attenuate its virulence, that is to say that the genetic mutations introduced have been introduced uniquely into genes encoding for proteins non-essential for the replication of the virus.

Various genetic modifications making it possible to attenuate the virulence of a virus strain are known to the person skilled in the art. These modifications may be introduced into the genome of the original strain rC-85473.

Genetic modifications designate, in the sense of the invention, all modifications of an original nucleotide sequence such as the deletion of one or more nucleotides, the addition of one or more nucleotides, and the replacement of one or more nucleotides. These modifications notably comprise all modifications making it possible to shift the genetic reading frame, or to introduce a stop codon into the middle of a coding sequence, or the deletion of all or part of one or more coding sequences.

Among genetic modifications intended to attenuate the virulence of a virus strain, genetic modifications are notably known making it possible to inactivate or even to delete one or more genes encoding for proteins non-essential for the replication of the virus in culture.

For example, attenuated virus strains of human metapneumovirus have been obtained by the inactivation, in particular by the deletion, of genes encoding for accessory SH, G and M2-2 proteins.

However, depending on the characteristics of the original virus strain from which the attenuated strains are derived, the functional characteristics of the attenuated virus strains could be very different, the virulence of the strains depending both on the original genome and on the genetic modifications made.

According to a first aspect of the invention, the attenuated virus strain according to the invention is characterised in that the modifications of the sequence SEQ ID NO.1 comprise the inactivation of the gene encoding for the SH protein.

More particularly, the attenuated virus strain according to the invention is characterised in that the genetic modification of sequence SEQ ID NO.1 attenuating the virulence of said strain consists in an inactivation of the gene encoding for the SH protein.

In the sense of the invention, the inactivation of a gene designates the fact that this gene is modified in such a way that the product of the gene is no longer expressed, or expressed in a non-active form, expressed in such a small amount that the activity of this protein is inexistent. This inactivation of a gene may be carried out by all techniques well known to the person skilled in the art.

In particular, the inactivation of a gene may be obtained by the introduction of a point mutation into the gene, by the partial or total deletion of the coding sequences of the gene, or instead by modification of the gene promoter. These different genetic modifications will be carried out according to any one of the molecular biology techniques well known to the person skilled in the art.

In the sense of the invention, "deletion of a gene" is taken to mean the removal from the genome of the virus strain of a significant part of the coding sequence of this gene, notably:

When it involves a partial deletion, at least 50%, 60%, 70%, 80%, 90% or 95% of said coding sequence;

When it involves a complete deletion, 100% of said coding sequence.

According to a preferred embodiment, in the attenuated virus strain according to the invention, the gene encoding for the SH protein is totally deleted, that is to say that all (100% of) the coding sequence for the SH protein has been removed from the original sequence SEQ ID NO. 1.

In particular, said virus strain comprises the nucleotide sequence such as represented in SEQ ID NO. 2. More specifically, the sequence of said virus strain consists of the nucleotide sequence such as represented in SEQ ID NO. 2.

Figure 7B:
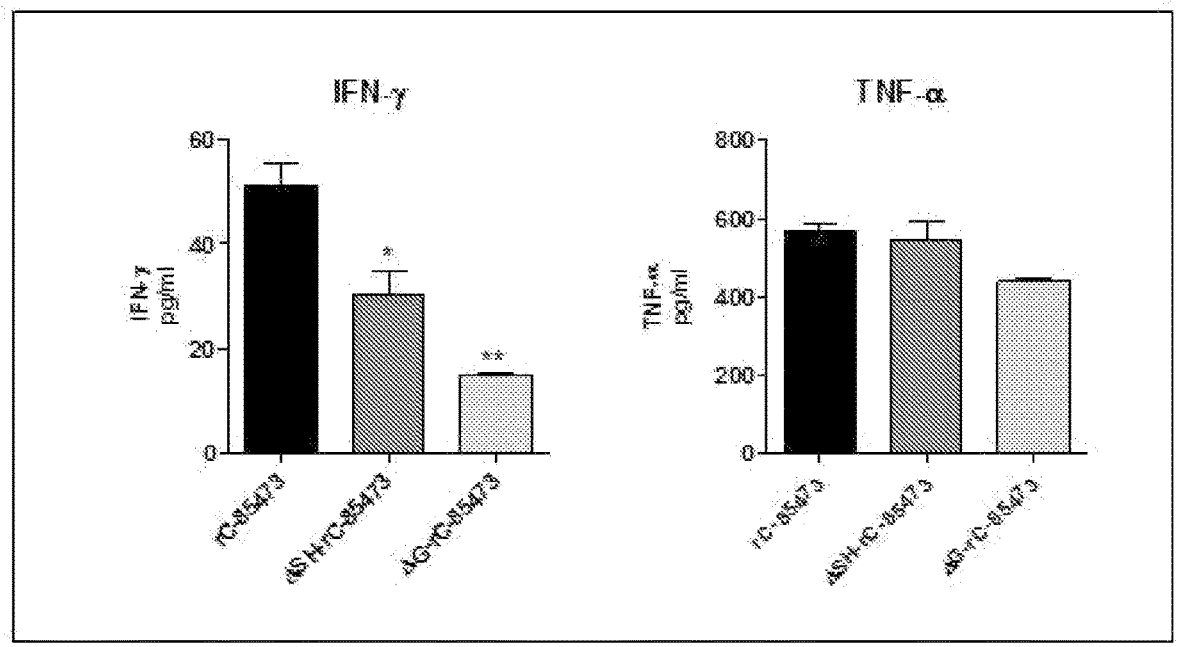

As is illustrated in the examples, this attenuated strain designated ΔSH-rC-85473 has the following characteristics:

In vitro, infection and replication on cells in culture are normal (no difference with the characteristics of the original strain);

In vivo, infection of mice with this recombinant virus ΔSH-rC-85473 only induces very little weight loss, unlike infection with the original strain; survival of the infected mice is 100%, whereas this attenuated virus replicates in the pulmonary tissues;

In vivo, prior immunisation of mice with this attenuated strain protects 100% of the mice challenged by a lethal dose of wild virus rC-85473. This protection is also illustrated by the absence of detection of infectious virus rC-85473 in the lungs 5 days after the challenge; and by a high micro-neutralisation load against the homologous virus strain (C-85473, of serotype A) and against at least one heterologous strain (CAN98-75, of serotype B) of the serums at D+21 after the infectious challenge;

In vitro, the capacity of binding to LLC-MK2 cells in culture and of cell infection is much better for the attenuated virus ΔSH-rC-85473 (around 60% of infected cells) in comparison with those of the virus ΔSH-rCAN98-75 (around 40% of infected cells);

Ex vivo, infection of a respiratory epithelium model by this attenuated strain induces the secretion of cytokines and chemokines in a quantity equivalent to or less than that induced by the wild strain; the inflammatory response is however reduced compared to that induced by the wild strain (FIGS. 7A, 7B);

In vitro, infection of macrophages by this attenuated strain induces the secretion of pro-inflammatory cytokines, but with a different kinetic from that viral-induced by the wild strain (FIGS. 8B, 8C);

In vivo, viral-induced inflammation of the pulmonary tissues is significantly lower following infection by this attenuated strain than with the wild strain (FIG. 9A); however, the recruitment of immune cells is still ensured (FIG. 9B).

According to a second aspect of the invention, the attenuated virus strain according to the invention is characterised in that the modifications of sequence SEQ ID NO.1 comprise the inactivation of the gene encoding for the G protein.

More particularly, the attenuated virus strain according to the invention is characterised in that the genetic modification of sequence SEQ ID NO.1 attenuating the virulence of said strain consists in an inactivation of the gene encoding for the G protein.

According to a preferred embodiment, in the attenuated virus strain according to the invention, the gene encoding for the G protein is totally deleted, that is to say that all (100% of) the coding sequence for the G protein has been removed from the original sequence SEQ ID NO. 1.

In particular, said virus strain comprises the nucleotide sequence such as represented in SEQ ID NO. 3. More specifically, the sequence of said virus strain consists of the nucleotide sequence such as represented in SEQ ID NO. 3.

As is illustrated in the examples, this attenuated strain designated ΔG-rC-85473 has the following characteristics:

In vitro, in the LLC-MK2 cell model, infection and replication on cells in culture are normal (no difference with the characteristics of the original strain);

In vivo, infection of mice infected with this recombinant virus ΔG-rC-85473 only induces very little weight loss; the survival of infected mice is 100%; whereas this virus replicates in the pulmonary tissues;

In vivo, prior immunisation of mice with this attenuated strain protects 100% of the mice challenged by a lethal dose of wild virus rC-85473. This protection is also illustrated by the absence of detection of infectious virus and wild genome rC-85473 in the lungs at D+5 after challenge; and by a high micro-neutralisation load against the homologous virus strain (C-85473, of serotype A) and against at least one heterologous strain (CAN98-75, of serotype B) of the serums at D+21 after infectious challenge;

In vitro, the capacity to bind to LLC-MK2 cells in culture and cell infection is much better for the attenuated virus ΔG-rC-85473 (around 60% of infected cells) compared to those of the virus ΔG-rCAN98-75 (fewer than 20% of infected cells).

Figure 7C:
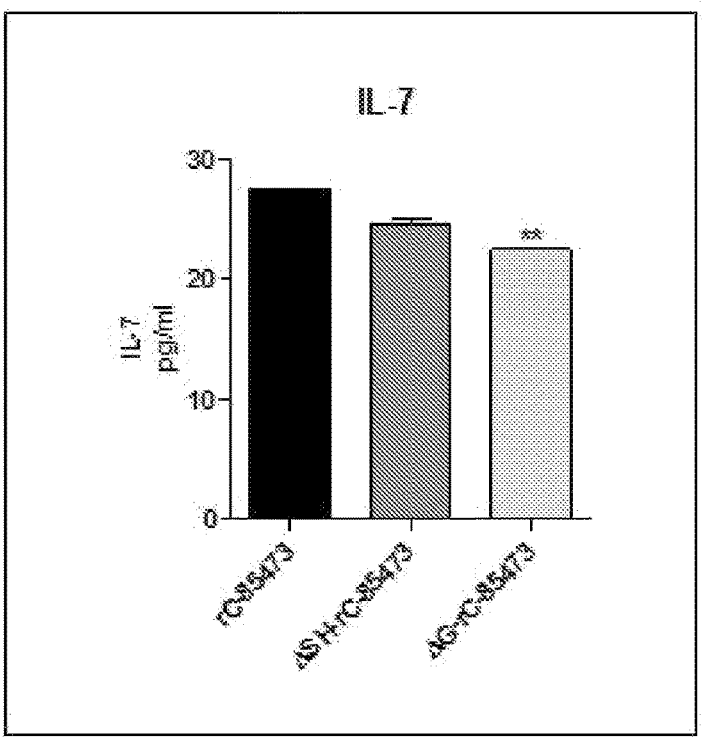

Ex vivo, the infection of a respiratory epithelium model by this attenuated strain induces the secretion of cytokines and chemokines in an amount significantly lower than that induced by the wild strain (FIG. 7);

In vitro, the infection of macrophages by this attenuated strain induces the secretion of TNF-α, in an equivalent manner to the secretion viral-induced by the wild strain; but only induces very slightly the secretion of IL-1β (FIGS. 8B, 8C);

In vivo, viral-induced inflammation of the pulmonary tissues is significantly lower following infection by this attenuated strain, than with the wild strain or than with the attenuated strain ΔSH-rC-85473 (FIG. 9A).

According to a third aspect of the invention, the attenuated virus strain according to the invention is characterised in that the modifications of sequence SEQ ID NO.1 comprise the inactivation of two genes encoding for the G protein and the SH protein.

More particularly, the attenuated virus strain according to the invention is characterised in that the genetic modifications of sequence SEQ ID NO.1 attenuating the virulence of said strain consist in an inactivation of the two genes encoding one for the SH protein and the other for the G protein.

According to a particular embodiment, the inactivation of the two genes corresponds to the complete deletion of one or the other or of the two genes encoding for the G and SH proteins.

In addition, it is understood that any other genetic modification making it possible to attenuate the virulence of the strain rC-85437 could be introduced into the genome of said strain, represented by sequence SEQ ID NO.1.

Introduction of Exogenous Genes into the Genome of the Virus Strain rC-85473

According to an aspect of the invention, the nucleotide sequence of the attenuated virus strain according to the invention could be genetically modified by the introduction of at least one exogenous gene.

Thus, the attenuated virus strain according to the invention has a genome sequence that comprises at least one exogenous gene. This exogenous gene could in particular be a gene encoding for a viral antigen.

In the sense of the invention, "viral antigen" is taken to mean a protein element or an element of another nature, expressed by a virus, which the immunological system of an individual recognises as foreign and which causes a response in said individual by the production of specific antibodies and/or the stimulation of a cell immune response.

Viral antigens could in particular be selected from antigens expressed by at least one influenza virus, or by at least one virus of the Pneumoviridae family, such as the hRSV, or by at least one virus of the Paramyxoviridae family, such as the parainfluenza virus.

More particularly, said viral antigen could be selected from all or part of the F protein of the hRSV, and all or part of the haemagluttinin of the influenza or parainfluenza virus.

This attenuated virus strain will make it possible, during its administration to a patient, to generate a multiple immune response, both against the viral antigen expressed and against hMPV.

Such a strain making it possible to obtain a combined immune response against several viruses, following a single administration, is very advantageous.

In addition, such an attenuated virus strain comprising at least one exogenous gene could be used in vivo, ex vivo or in vitro, as expression vector of at least one exogenous gene in target cells of the human metapneumovirus.

'Target cells of the human metapneumovirus' designates the epithelial cells of the respiratory tract of individuals liable to be infected by this virus. This expression also designates all the cell lines enabling the in vitro replication of said virus.

Attenuated Virus Strain for the Use Thereof as a Medicine

The present invention also relates to an attenuated virus strain such as defined above, for the use thereof as a medicine.

Indeed, this strain may be used, notably, for treating or preventing viral infections.

The term "treat" designates the fact of combatting infection by a virus in a human or animal organism. Thanks to the administration of at least one composition according to the invention, the level of viral infection (infectious load) in the organism is going to decrease, and preferably the virus is going to disappear completely from the organism. The term "treat" also designates the fact of attenuating the symptoms associated with the viral infection (respiratory syndrome, renal failure, fever, etc.).

In the sense of the invention, the term "prevent" designates the fact of avoiding, or at least decreasing the risk of occurrence of an infection in a human or animal organism. Thanks to the administration of at least one attenuated virus strain according to the invention, the human or animal cells of said organism become less permissive to infection, and are thus best placed not to be infected by said virus.

More specifically, the invention relates to an attenuated virus strain such as defined above, for the use thereof for preventing and/or treating infections by viruses of the Pneumoviridae family.

It is understood that this attenuated virus strain will be preferably integrated in a vaccine composition comprising a pharmaceutically acceptable vehicle, suitable for suspending said strain and for the administration thereof.

Said vaccine composition comprises at least one attenuated virus strain according to the invention, making it possible to stimulate in a specific manner the immune system of a human or animal organism.

Thus, this vaccine composition comprises at least one attenuated living virus strain which plays the role of antigen, that is to say of compound inducing a specific immune response in the organism, which will retain the memory thereof.

Such a vaccine composition could be used as a preventive vaccine, that is to say intended to stimulate a specific immune response before infection of an organism by a pathogenic virus.

Such a vaccine composition could also be used as a therapeutic vaccine, that is to say intended to stimulate a specific immune response concomitantly with infection of an organism by said pathogenic virus.

The present invention also relates to a method for preventing and/or treating infections by Pneumoviridae in humans, comprising the administration, to individuals liable to be infected by such viruses, of at least one attenuated virus strain such as described previously.

The present invention also relates to a method for preventing and/or treating infections by Pneumoviridae in humans, comprising the administration, to individuals liable to be infected by such viruses, of at least one vaccine composition comprising at least one attenuated virus strain such as described previously.

According to a specific embodiment of the invention, the infections are infections by human metapneumoviruses.

According to another specific embodiment of the invention, the infections are infections by orthopneumoviruses, such as the human syncytial respiratory virus (hRSV).

The invention also relates to an attenuated virus strain, the sequence of which comprises at least one exogenous gene encoding for a viral antigen, for the use thereof for preventing and/or treating infections by viruses in which at least one viral antigen is expressed by said attenuated virus strain.

According to a particular embodiment, an attenuated virus strain according to the invention comprising, as exogenous viral antigen, the F protein of a hRSV, could be used for preventing and/or treating infections by a hRSV.

According to another particular embodiment, an attenuated virus strain according to the invention comprising, as exogenous viral antigen, the haemagluttinin of an influenza virus, could be used for preventing and/or treating infections by an influenza virus.

Pharmaceutical Composition Comprising at Least One Attenuated Virus Strain

The present invention also relates to a vaccine composition comprising, in a pharmaceutically acceptable vehicle, at least one attenuated virus strain according to the invention, and optionally an adjuvant.

According to the invention, the term "pharmaceutically acceptable vehicle" designates vehicles or excipients, that is to say compounds not having specific action on the infection considered here. These vehicles or excipients are pharmaceutically acceptable, which signifies that they may be administered to an individual or to an animal without risk of significant deleterious effects or prohibitive undesirable effects.

It is understood that the vaccine composition according to the invention comprises at least one effective amount of the attenuated virus strain. "Effective amount" is taken to mean, in the sense of the invention, a quantity of attenuated virus strain sufficient to trigger an immune reaction in the organism to which it is administered.

The vaccine compositions used according to the present invention are suited for oral, sublingual, inhalation, subcutaneous, intramuscular or intravenous administration.

According to a particular embodiment of the invention, the vaccine composition according to the invention is characterised in that it is in a pharmaceutical form intended for administration by inhalation.

Inhalation designates absorption by the respiratory tracts. It is in particular a method for absorption of compounds for therapeutic purposes, of certain substances in the form of gas, micro-droplets or powders in suspension.

The administration of pharmaceutical or veterinary compositions by inhalation, that is to say by the nasal and/or buccal passageways, is well known to the person skilled in the art.

Two types of administration by inhalation are distinguished:
  administration by insufflation, when the compositions are in the form of powders, and
  administration by nebulisation, when the compositions are in the form of aerosols (suspensions) or in the form of solutions, for example pressurised, aqueous solutions. The use of a nebuliser or a spray will then be recommended for administering the pharmaceutical or veterinary composition.

The pharmaceutical form considered here is thus advantageously selected from: a powder, an aqueous suspension of droplets or a pressurised solution.

The population of individuals to vaccinate is mainly a pediatric population, that is to say constituted of individuals less than 18 years old, and more specifically young children less than 5 years old, and infants. Indeed, viruses of the Pneumoviridae family mainly infect these individuals, who have a tendency to have less strong immunity than older individuals.

The invention also relates to a vaccine composition such as described above, for the use thereof for preventing and/or treating infections by viruses of the Pneumoviridae family

EXAMPLES

Example 1: Recombinant hMPVs Generated from the Clinical Strains C-85473 and CAN98-75. 1A The genetic constructions represented in FIGS. 1A and 1B were prepared in order that the viruses are detectable by expression of GFP (Green Fluorescent Protein), and to introduce into the recombinant reference strains rC-85473 and rCAN98-75 the genetic modifications intended to attenuate their virulence:
  The deletion of the gene encoding for the SH protein (ΔSH);
  The deletion of the gene encoding for the G protein (ΔG).

The complete sequences of these genetic constructions are presented in SEQ ID NO. 4 (GFP rC-85473), SEQ ID NO.5 (GFP ΔSH-rC-85473), SEQ ID NO.6 (GFP ΔG-rC-85473) and SEQ ID NO. 8 (GFP rCAN98-75). The sequences of the virus strains derived from rCAN98-75 and coupled to GFP are not represented but are accessible to the person skilled in the art on the basis of the other genetic constructions presented.

As the photos of LLC-MK2 cells infected with a multiplicity of infection (MOI) of 0.01 show, the viruses being visible thanks to GFP, the following generated recombinant viruses: ΔSH-rCAN98-75, ΔG-rCAN98-75, ΔSH-rC-85473 and ΔG-rC-85473 are functional and replicative. The cells are observed by fluorescence microscopy at three days post-infection.

The photos suggest that the recombinant viruses rCAN98-75 seem less infectious and less replicative than the recombinant viruses rC-85473: the intensity of the fluorescence is lower, and the syncytia are of more reduced dimensions.

Example 2: In Vitro Replicative Capacities of the Recombinant Viruses rC-85473 and rCAN98-75

Figure 2A:
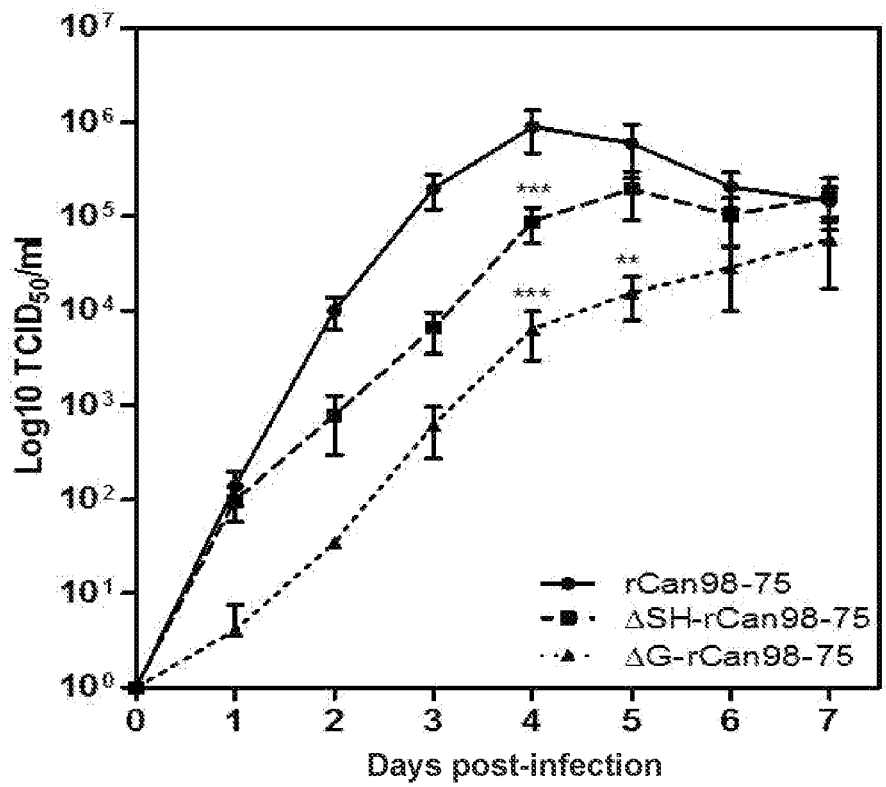
FIG. 2A Viral load evaluated by TCID50/ml in the cell supernatants collected each day for 7 days after infection of LLC-MK2 cells by the recombinant viruses rCAN98-75 (black circles), ΔSH-rCAN98-75 (black squares) and ΔG-rCAN98-75 (black triangles) with a multiplicity of infection (MOI) of 0.01.
Figure 2B:
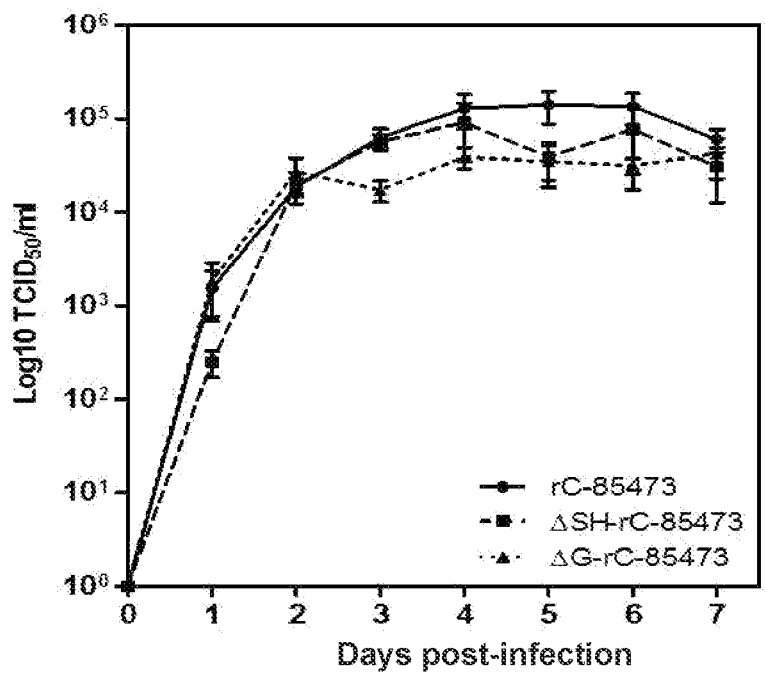
FIG. 2B Viral load evaluated by TCID50/ml in the cell supernatants collected each day for 7 days after infection of LLC-MK2 cells by the recombinant viruses rC-85473 (black circles), ΔSH-rC-85473 (black squares) and ΔG-rC-85473 (black triangles) with a multiplicity of infection of 0.01.
Figure 3A:
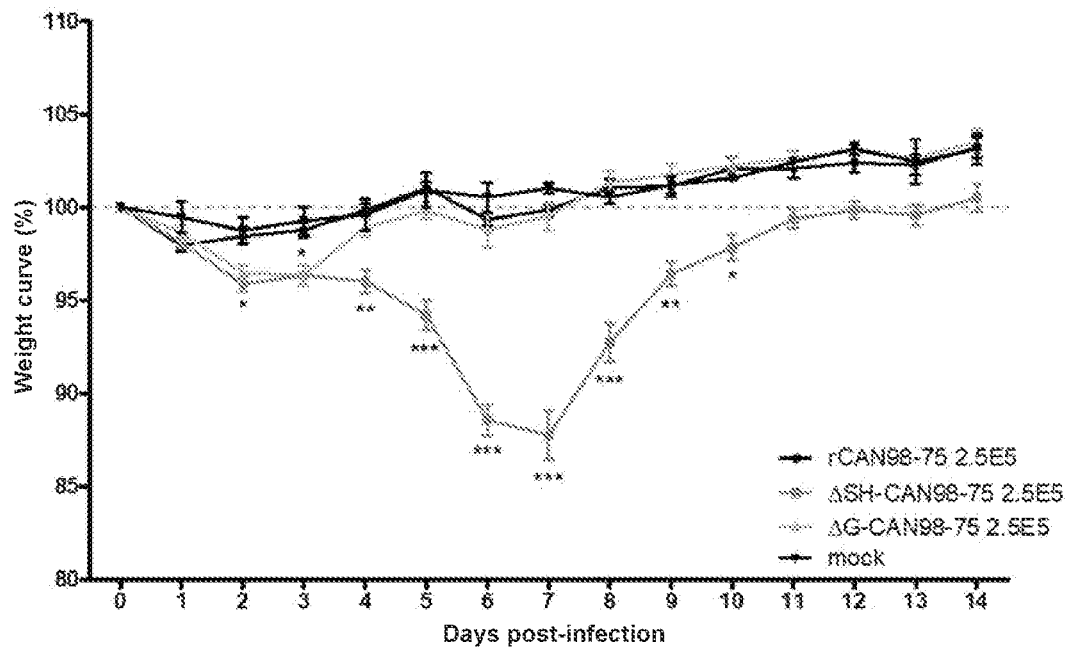
Figure 3B:
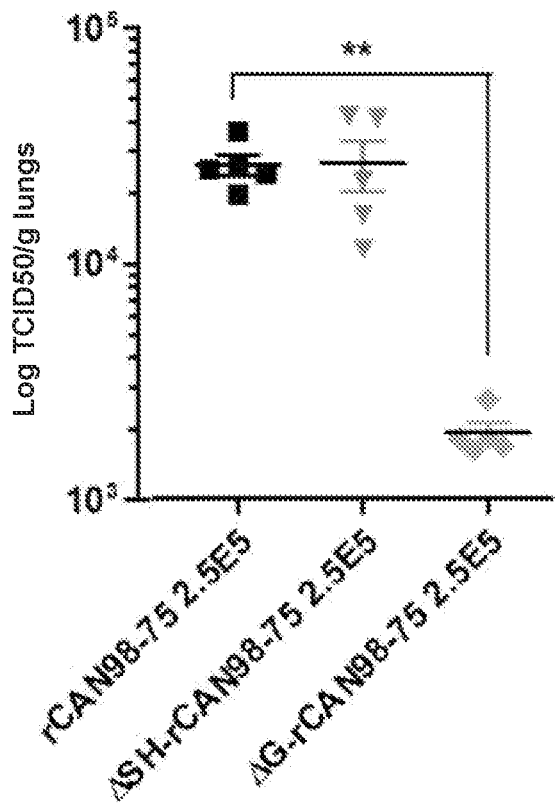
Figure 3C:
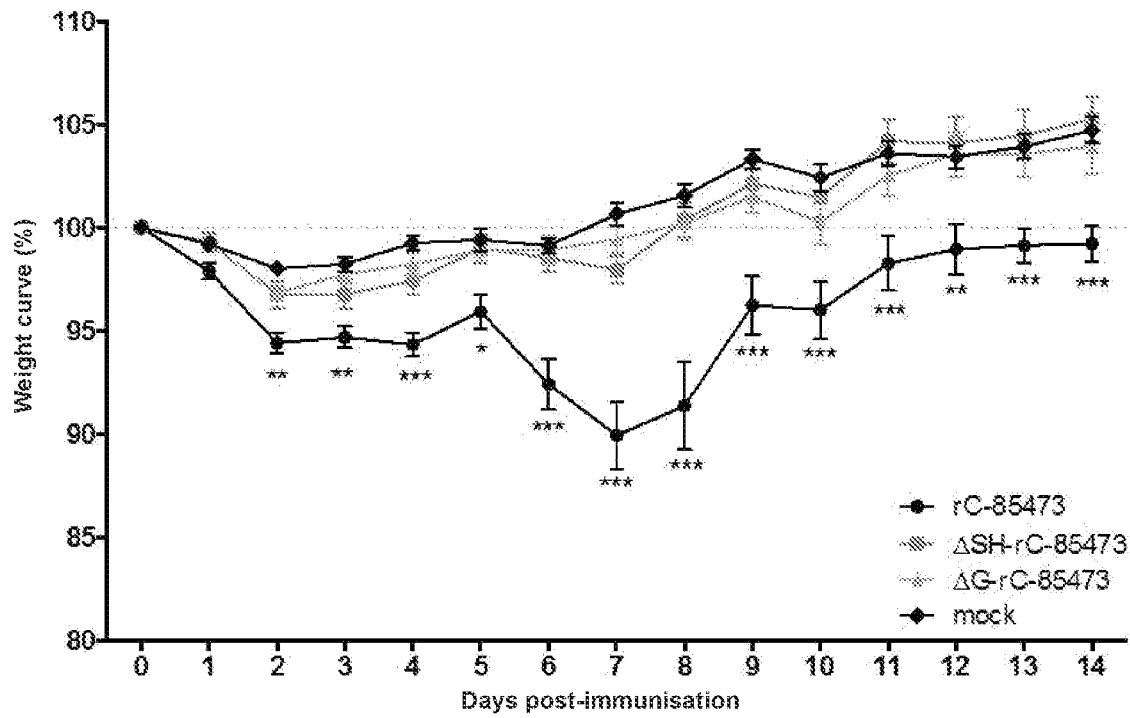
Figure 3D:
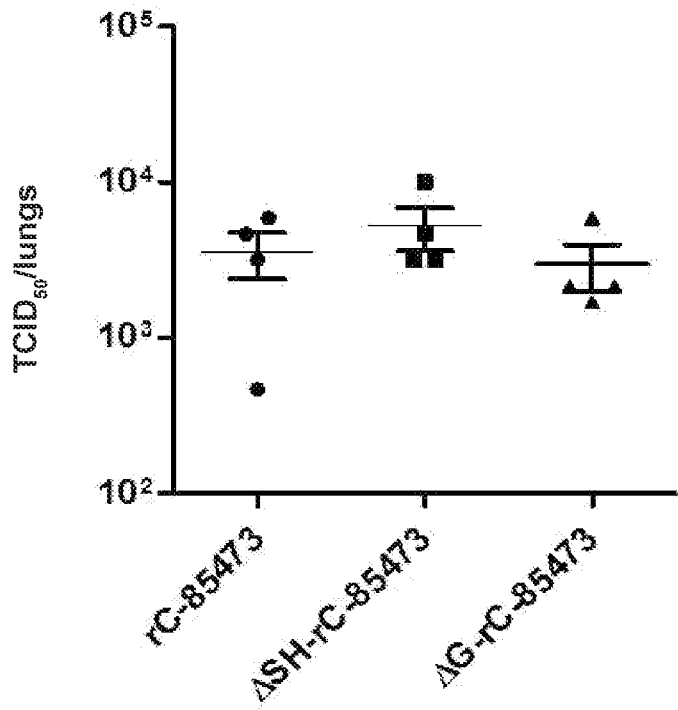

LLC-MK2 cells were infected separately, with a multiplicity of infection of 0.01, by the following recombinant viruses:
  rCAN98-75, ΔSH-rCAN98-75 and ΔG-rCAN98-75 (FIG. 2A)
  rC-85473, ΔSH-rC-85473 and ΔG-rC-85473 (FIG. 2B)

The cell supernatants were collected each day for 7 days, in triplicate, then their viral loads were evaluated in TCID50/ml. Two-way ANOVA statistical tests were carried out to compare each deleted recombinant virus (ΔSH and ΔG) with the wild recombinant virus.

FIGS. 2A and 2B show the results obtained: the replicative and production capacities are different as a function of the nature of the original strain, CAN98-75 or C-85473, for the attenuated recombinant viruses.

The recombinant viruses rC-85473, ΔSH-rC-85473 and ΔG-rC-85473 have replicative and production capacities much better than those of the viruses rCAN98-75, ΔSH-rCAN98-75 and ΔG-rCAN98-75. The viruses ΔSH-rCAN98-75 and ΔG-rCAN98-75 are the least efficient, whereas the viruses ΔSH-rC-85473 and ΔG-rC-85473 have the best production capacities in culture on LLC-MK2 cells.

In the tables below are represented the average loads of the viral stocks produced and concentrated for each recombinant virus rCAN98-75, ΔSH-rCAN98-75 and ΔG-rCAN98-75 (tableau 5) and rC-85473, ΔSH-rC-85473 and ΔG-rC-85473 (table 6).

The viral loads are counted in "TCID50" units which represents the final viral dilution at which 50% of the cell tissue is destroyed by the infection, or shows visible cytopathic effects (50% Tissue Culture Infective Dose).

TABLE 5

| Recombinant viruses | Average load of the concentrated stock (TCID50/ml) |
| --- | --- |
| rCAN98-75 | 4.37E+07 |
| ΔSH -rCAN98-75 | 2.77E+07 |
| ΔG -rCAN98-75 | 8.65E+06 |

TABLE 6

| Recombinant viruses | Average load of the concentrated stock (TCID50/ml) |
| --- | --- |
| rC-85473 | 3.92E+07 |
| ΔSH -rC-85473 | 1.81E+08 |
| ΔG -rC-85473 | 2.04E+08 |

These viral loads confirm the preceding results, namely that the attenuated virus strains derived from C-85437 have satisfactory replication capacities, not diminished compared to those of the original strain.

Example 3: In Vivo Characterisation of the Recombinant hMPVs rCAN98-75 and rC-85473 on a BALB/c Mice Viral Infection Model BALB/c mice were infected by intranasal instillation with:

OptiMem culture medium (mock) or $2.5\times10^5$ Fluorescent Focal Units (FFU) of recombinant viruses expressing GFP: rCAN98-75, ΔSH-rCAN98-75 and ΔG-rCAN98-75, or $5\times10^5$ TCID50 of viruses not expressing GFP: rC-85473, ΔSH-rC-85473 and ΔG-rC-85473.

The two virus doses used are equivalent (the wild viruses produce equivalent effects in the mice after infection).

The weight and the survival of the mice was monitored daily for 14 days (weight average over 10 mice±SEM).

In addition, 5 days after the infection, 5 mice by group underwent euthanasia for a measurement of pulmonary infection viral loads in TCI D50.

Statistical tests were carried out (two-way ANOVA) to compare each virus with the mock condition. $*p<0.05$, $$ $p<0.01$ and $*$, $p<0.001$.

FIGS. 3A and 3B show the results obtained with the viruses rCAN98-75, ΔSH-rCAN98-75 and ΔG-rCAN98-75; FIGS. 3C and 3D show the results obtained with the viruses rC-85473, ΔSH-rC-85473 and ΔG-rC-85473.

These results indicate that the recombinant viruses ΔSH-rC-85473 or ΔG-rC-85473 only induce very little weight loss; in fact these groups of mice behave like the non-infected group of mice.

Furthermore, the pulmonary viral loads (FIG. 3D) are similar to those observed in the group infected by the virus rC-85473, indicating pulmonary replication of the deleted attenuated viruses.

The results are different with the recombinant viruses ΔSH-rCAN98-75 and ΔG-rCAN98-75: the virus ΔSH-rCAN98-75 induces a very great weight loss (FIG. 3A); whereas the virus ΔG-rCAN98-75 only induces a very slight decrease in weight (FIG. 3A), on account of its low capacity for replicating in the lungs (FIG. 3B).

Example 4: In Vivo Protective Properties of the Recombinant hMPVs ΔG-rC-85473 and ΔSH-rC-85473 in a BALB/c Murine Model Following an Infectious Challenge by the Wild Virus rC-85473

The immunisation and infectious challenge protocol is shown in FIG. 4A.

BALB/c mice were immunised by intranasal instillation with of the OptiMem culture medium ("mock" negative control) or $5\times10^5$ $TCID^{50}$ of the recombinant viruses rC-85473, ΔSH-rC-85473 or ΔG-rC-85473.

21 days after immunisation, the mice were infected (infectious challenge) by intranasal instillation of a lethal dose ($1\times10^6$ $TCID^{50}$) of the wild virus rC-85473.

The weight and survival of the mice was monitored daily for 14 days (weight average over 10 mice±SEM, FIG. 4B).

The survival of the mice was monitored daily for 14 days post-challenge, for the mice of the different groups (mock with 50% survival and immunised by the recombinant viruses rC-85473, ΔSH-rC-85473 or ΔG-rC-85473, exhibiting 100% survival). The results are shown in FIG. 4C.

5 days after the infectious challenge (i.e. at day 26 post-immunisation), 4 mice of each group underwent euthanasia to measure their pulmonary infection viral loads in TCID50 (FIG. 4D) and RTqPCR (N gene, FIG. 4E).

Statistical tests: Two-way ANOVA to compare each virus with the mock condition. $*p<0.05$, $$ $p<0.01$ and $*$, $p<0.001$.

These results confirm that the recombinant viruses ΔSH-rC-85473 or ΔG-rC-85473 only induce very little weight loss (the groups of mice behave like the group of non-infected mice) and that, in these experimental conditions, protect 100% of the mice challenged by a lethal dose of wild virus rC-85473. This protection is also illustrated by the absence of detection of infectious virus and wild genome rC-85473 (nd) in the lungs at D+5 after challenge and a high micro-neutralisation load of the serums at D+21 after challenge (>160) of mice immunised beforehand by the recombinant viruses ΔSH-rC-85473 and ΔG-rC-85473.

Table 7 below shows the results of micro-neutralisation tests, carried out from serums taken from mice of the different groups at D+20 (1 day before the infectious challenge) and at D+42 (21 days after the infectious challenge).

After inactivation for 30 minutes at 56° C. and dilution of the serums, they were incubated with 100 TCID50 (that is to say 100 infectious units such as determined according to the TCDI50/ml) of virus rC-85473 or virus rCAN98-75 for 2 hours at 37° C. This mix was next applied to the LLC-MK2 cells for a determination of the neutralisation load.

The neutralising antibody load is determined by the greatest dilution of serum at which LLC-MK2 cells, incubated with the serum+virus mix, do not show cytopathic effects, that is to say are considered negative for infection (on the basis of tests carried out in duplicate).

TABLE 7

| Serums | Micro-neutralisation test Day 20 before infectious challenge | Day 42, 21 days after infectious challenge (strain C-85473) | Day 42, 21 days after infectious challenge (strain CAN98-75, serotype B) |
|---|---|---|---|
| Mock | ≤5 | 10 | 10 |
| rC-85473 | 5 | ≥160 | 80 |
| ΔSH rC-85473 | 5-10 | ≥160 | ≥160 |
| ΔG rC-85473 | 5-10 | ≥160 | 80 |

The figures represent the dilution of the serums tested at which the specific antibody loads efficiently neutralise the viral infection (micro-neutralisation load).

A result of 5 or 10 is representative of a primary immune response (first encounter with the virus). A result greater than or equal to 160 is characteristic of a maximum immune response, and signifies that the organism had already encountered the virus previously and thus was immunised.

The virus strains derived from the original strain rC-85473 make it possible to obtain a satisfactory neutralising humoral response against hMPV C-85473 (serotype A) and at least against the virus CAN98-75 (serotype B), after prior immunisation by the attenuated strains.

Example 5: In Vitro Cellular Binding Capacities of the Recombinant Viruses rC-85473 and rCAN98-75

Figure 5A:
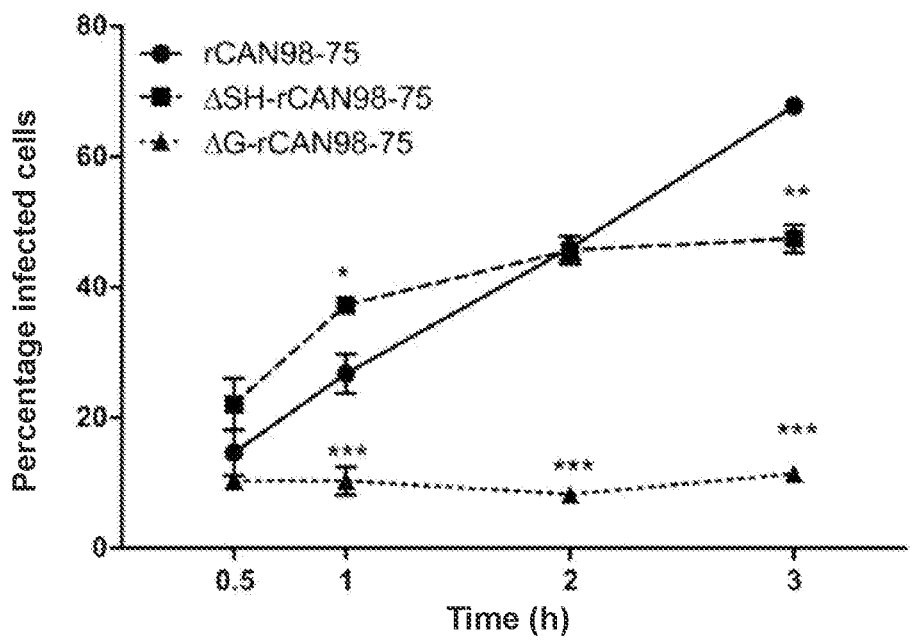
Figure 5B:
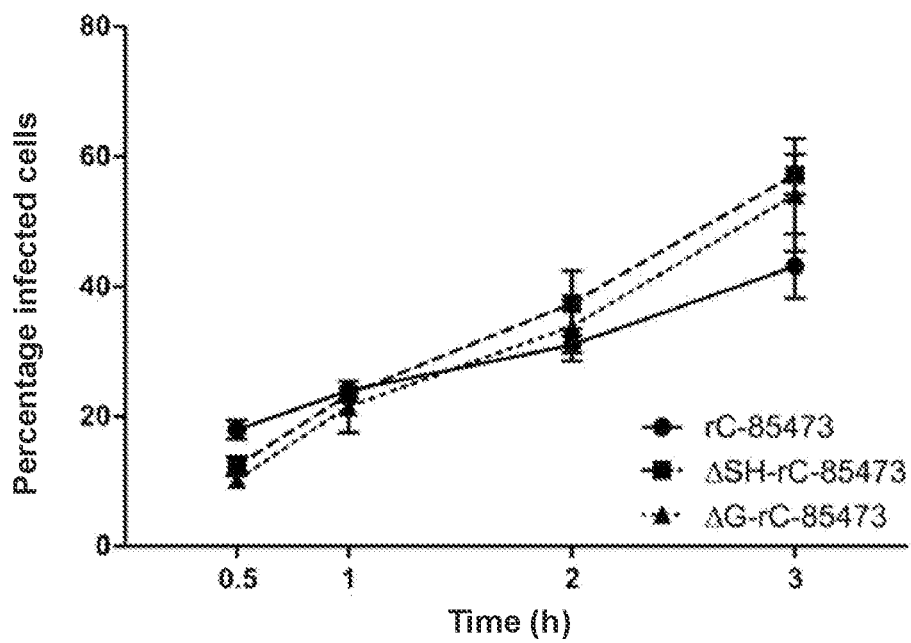
Figure 6A:
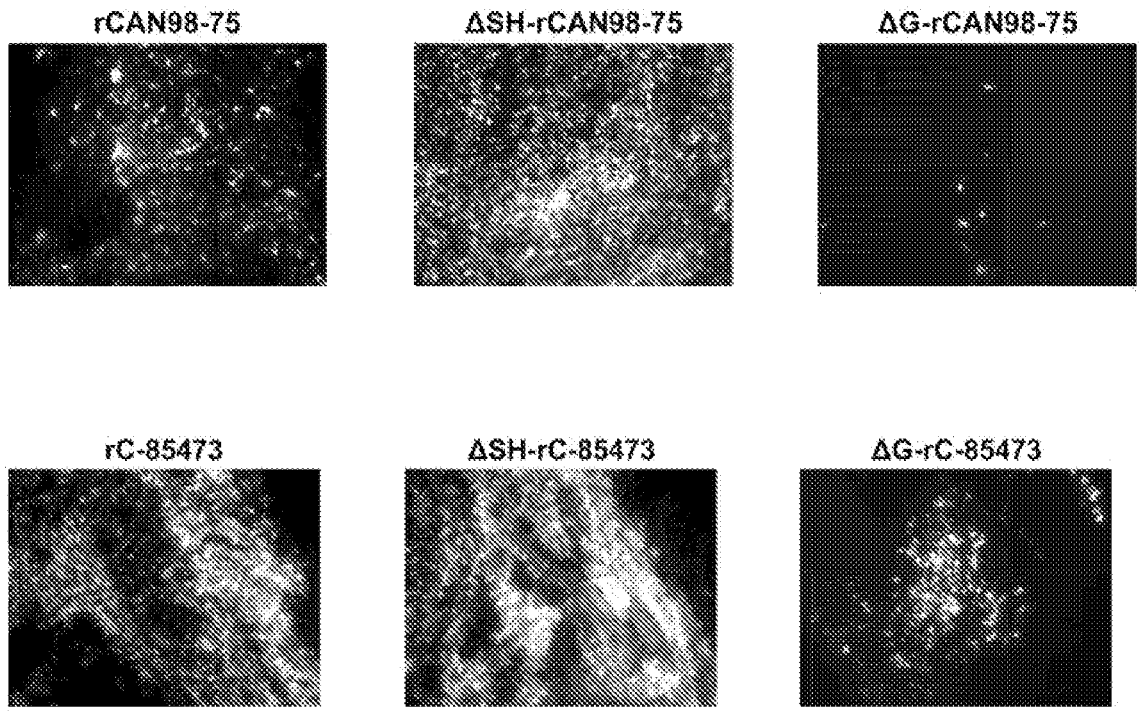
Figure 6B:
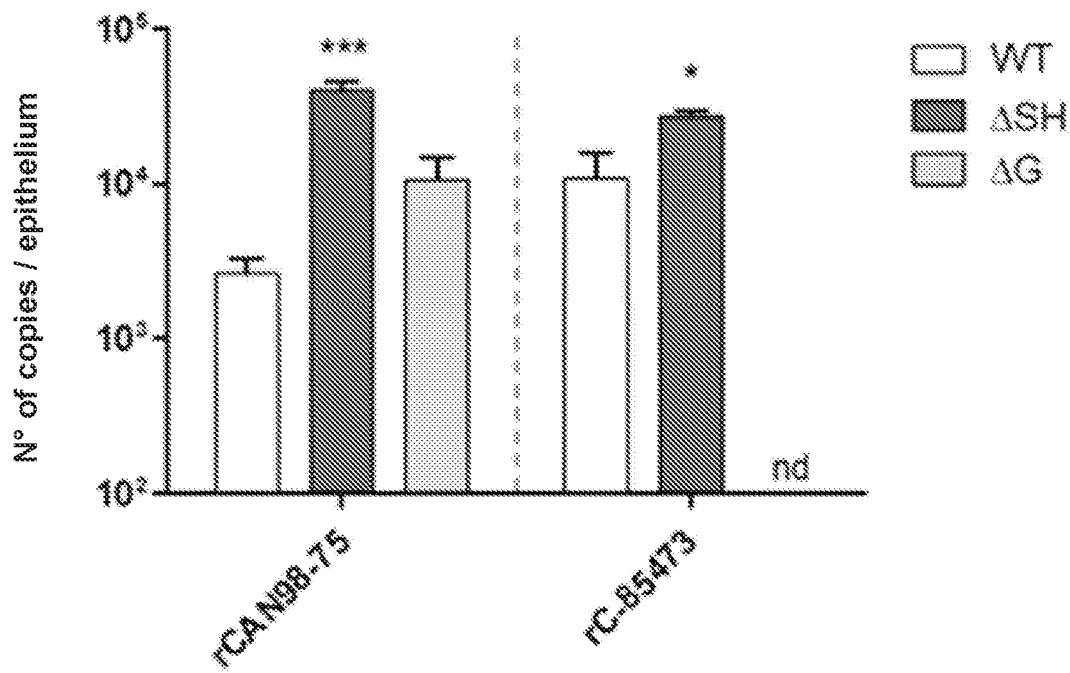
Figure 6C:
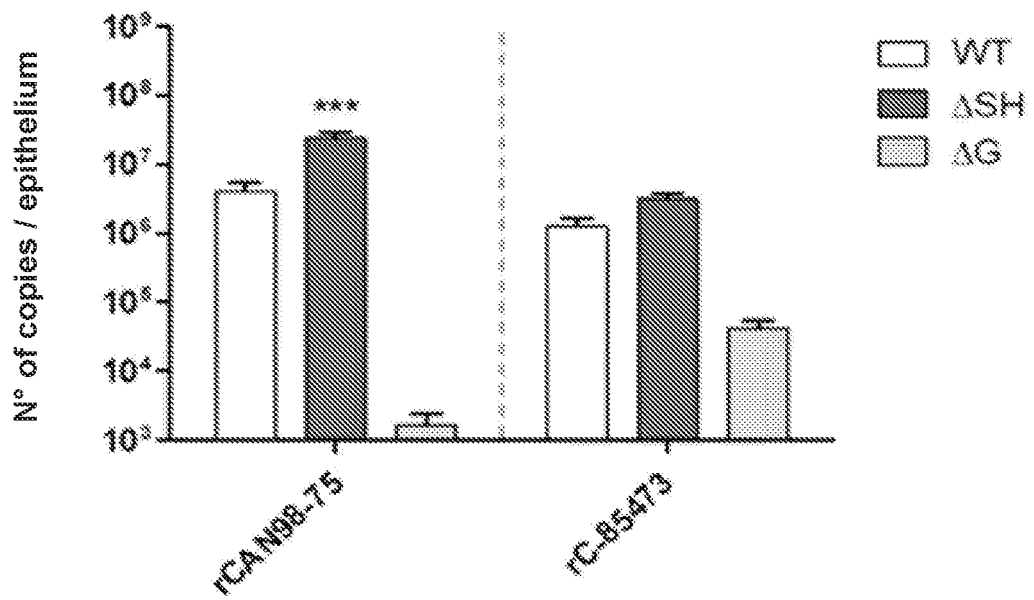

LLC-MK2 cells were infected (t=0) with:
the virus rCAN98-75 and the attenuated forms thereof ΔSH-rCAN98-75 and ΔG-rCAN98-75 (FIG. 5A);
the virus rC-85473 and the attenuated forms thereof ΔSH-rC-85473 and ΔG-rC-85473 (FIG. 5B);
The cells were infected on ice, for 0.5, 1, 2 or 3 h in order to vary the time of binding the viruses to the cells, before being washed then incubated at 37° C. for 24 h.

The percentage of cells infected measured at 24 h post-infection is representative of the quantity of virus capable of binding to the cells within the allocated time (0.5, 1, 2 or 3 h).

The results indicate different capacities of binding to LLC-MK2 cells in culture (and thus infection capacities) for the recombinant viruses as a function of the origin of their genome CAN98-75 or C-85473.

The results show much better cell binding and cell infection capacity for the attenuated viruses ΔSH-rC-85473 and ΔG-rC-85473 (around 60% of infected cells) in comparison to those of the viruses ΔSH-rCAN98-75 (40%) and ΔG-rCAN98-75 (fewer than 20% of infected cells).

Example 6: Ex Vivo Replicative Capacities of the Recombinant Viruses rC-85473 and rCAN98-75 in a Reconstituted Human Respiratory Epithelium 3D Model and Cultured at the Air-Liquid Interface Reconstituted human respiratory epitheliums (MucilAir® HAE, Epithelix) and maintained in culture at the air-liquid interface according to the instructions of the supplier Epithelix, were used to carry out these ex vivo experiments.

The photos shown in FIG. 6A indicate that the recombinant viruses rCAN98-75 appear less infectious and less replicative than the recombinant viruses rC-85473 (lower intensity of fluorescence and more reduced dimensions of the sites of infection).

The results of quantification of viral genome in the epitheliums (FIG. 6C) confirm the replicative capacities of the recombinant viruses rC-85473, ΔSH-rC-85473 and ΔG-rC-85473, as well as the recombinant viruses rCAN98-75 and ΔSH-rCAN98-75, unlike the virus ΔG-rCAN98-75 which is very weakly replicative.

The results of quantification of viral genome at the surface of the apical pole of the epitheliums (FIG. 6B) indicate production of recombinant viruses rCAN98-75, ΔSH-rCAN98-75, ΔG-rCAN98-75, rC-85473 and ΔSH-rC-85473.

On the other hand, no genome of the virus ΔG-rC-85473 is detected, indicating the absence of viral progeny production. A hypothesis is that the virus ΔG-rC-85473 could have lost the capacity to bud at the surface of the cells infected in this complex and pluri-stratified ex vivo system.

These differences could be of a nature to further argue in favour of the inventive character of our invention, focusing on the different properties between recombinant viruses of different origins in terms of hMPV virus strain, for the protection of our attenuated living vaccine candidates ΔSH-rC-85473 and ΔG-rC-85473.

Example 7: Secretion of Cytokines and Chemokines Induced by Infection with the Recombinant Viruses rC-85473 on a Reconstituted Human Respiratory Epithelium 3D Model and Cultured at the Air-Liquid Interface Reconstituted human respiratory epitheliums (MucilAir® HAE, Epithelix) maintained in culture at the air-liquid interface, according to the instructions of the supplier Epithelix, were used to carry out these ex vivo experiments.

The quantification of a selection of cytokines and chemokines secreted in the basal medium of the infected epitheliums reflects the induction of a cell response that differs as a function of the recombinant viruses rC-85473 evaluated (FIG. 7).

a) the virus ΔG-rC-85473 induces the secretion of a significantly lower quantity of the different cytokines and chemokines tested, in comparison with the wild strain rC-85473, with the exception of the pro-inflammatory cytokine TNF-α. These results are consistent with those shown in FIG. 6, which show that the infectivity of this virus in reconstituted human respiratory epithelium is significantly reduced compared to the infectivity of the wild strain.

b) the virus ΔSH-rC-85473, even though its capacity for infection and replication in the reconstituted human respiratory epithelium model is increased compared to that of the wild recombinant virus rC-85473 (FIG. 6), induces the secretion of an equivalent or lower amount of the panel of cytokines and chemokines evaluated compared to that viral-induced by the wild virus.

The levels of secreted chemokines MCP-1, IP-10, RANTES, IL-8, G-CSF and pro-inflammatory cytokines IFN-γ and TNF-α seem to indicate that epithelial cells infected by this virus ΔSH-rC-85473 are able to recruit the T lymphocyte, monocyte/macrophage, eosinophil and/or neutrophil immune cells necessary for putting in place an innate immune response and adaptive response of the host.

In addition, the virus ΔSH-rC-85473 leads to the secretion of IL-7, a cytokine inducing the differentiation of inactive lymphocytes into active T and B lymphocytes, and FGF, a growth factor involved in the repair of organic tissues, in amounts similar to the wild virus rC-85473.

Thus, infection by the virus ΔSH-rC-85473 enables epithelial cells to put in place the primary defence response to the infection, while being associated with a more reduced inflammatory response of the host, in comparison with that induced by the wild virus.

These differences would thus be in favour of the use of recombinant viruses derived from the strain rC-85473 as attenuated living vaccine, and preferentially from the attenuated strain ΔSH-rC-85473.

Example 8: Viral Replication and Secretion of the Pro-Inflammatory Cytokines IL-1β and TNF-α In Vitro of the Recombinant hMPVs rC-85473 on an Immortalised Murine Macrophage Model An immortalised line of mice macrophages was used to evaluate the replication and induction capacity of pro-inflammatory cytokines by the recombinant viruses rC-85473, ΔSH-rC-85473 and ΔG-rC-85473.

Macrophages form part of the first cells of the immune system recruited on the site of infection (in the present case, the respiratory epithelium). Macrophages contribute to the inflammatory response, to the innate response and to the stimulation of the adaptive response of the host.

The macrophages were infected by the recombinant viruses rC-85473, ΔSH-rC-85473 or ΔG-rC-85473 and their cell supernatants were collected each day for 2 days. The results are shown in FIG. 8.

a) the viral loads measured in FFU/ml demonstrate that the virus ΔSH-rC-85473 has a decreased replicative capacity on the macrophages, compared to the wild recombinant virus, whereas the virus ΔG-rC-85473 shows a viral replication similar to the wild virus (FIG. 8A). Two-way ANOVA statistical tests were carried out to compare the kinetic of replication of the deleted virus ΔSH-rC-85473 with that of the wild recombinant virus.

b) the secretion of the pro-inflammatory cytokines TNF-α (FIG. 8B) and IL-1β (FIG. 8C) was next measured in the supernatant of the infected macrophages.

The virus ΔSH-rC-85473 leads to a cytokine profile significantly different from that of the wild virus rC-85473 with an earlier secretion peak after 1 day post-infection, in comparison with the wild virus which is associated with a secretion peak at 2 days post-infection, concerning these two cytokines.

The virus ΔG-rC-85473 induces the secretion of cytokine TNF-α at levels comparable to the wild virus, but does not induce the secretion of cytokine IL-1β during the 2 first days of infection.

These results demonstrate that the virus ΔSH-rC-85473 conserves the capacity to infect murine macrophages, and especially to lead to the secretion of pro-inflammatory cytokines, despite a modified kinetic.

The virus ΔG-rC-85473 efficiently infects murine macrophages, but induces more weakly the secretion of pro-inflammatory cytokines, as has been observed on the reconstituted human respiratory epithelium model.

Example 9: Pulmonary Inflammation and Recruitment of Immune Cells on the Site of the Infection In Vivo Induced after 5 Days of Infection of BALB/c Mice by the Recombinant hMPVs rC-85473, ΔG-rC-85473 and ΔSH-rC-85473

BALB/c mice were infected by intranasal instillation with:
OptiMem (mock) culture medium
$5 \times 10^5$ TCID$^{50}$ of the recombinant viruses rC-85473, ΔSH-rC-85473 or ΔG-rC-85473.

After 5 days of infection, 5 mice per group underwent euthanasia and their lungs taken for a histo-pathological analysis and a measurement of the inflammation scores resulting from infection (FIG. 9A).

Statistical tests were carried out (two-way ANOVA) to compare each condition with each other: $*p<0.05$, $ p<0.01$ and $*, p<0.001$.

FIG. 9A shows that the wild virus rC-85473 induces a strong pulmonary inflammation in the infected mice, whereas the viruses ΔSH-rC-85473 and ΔG-rC-85473 lead to an inflammation that is significantly lower than the wild virus, in adequation with the reduced severity of the pathology with the attenuated strains demonstrated previously in FIG. 3.

Furthermore, at 5 days post-infection, 5 mice per group underwent euthanasia and their lungs taken for the absolute quantification of the CD4+, CD8+ lymphocyte, neutrophil and macrophage immune cells infiltrated into the pulmonary tissue following infection (FIG. 9B).

Statistical tests were carried out (one-way ANOVA) to compare the condition ΔSH-rC-85473 with the condition rC-85473: $** p<0.01$.

FIG. 9B demonstrates that the different populations of immune cells (CD4+T, CD8+T, neutrophils and macrophages) are recruited on the site of the infection after 5 days of inoculation of the viruses rC-85473 and ΔSH-rC-85473, but in lower quantity for the attenuated strain, notably as regards CD4+ lymphocytes.

Thus, it would seem that the virus ΔSH-rC-85473 leads to reduced pulmonary inflammation, in coherence with the attenuation of the pathology viral-induced in a murine model (FIG. 3) and the decrease in the secretion of cytokines by the infected epithelial cells (FIG. 7), while ensuring efficient recruitment of the different immune cells on the site of the infection.

These different results (FIGS. 7 to 9) show the different properties between wild recombinant rC-85473 and deleted viruses with regard to their post-infection physiological effects.

The attenuated strain ΔSH-rC-85473 seems particularly promising for the development of an attenuated living vaccine, with regard to its properties from the point of view of (i) the secretion of inflammatory cytokines and chemokines by epithelial and macrophagic cells, (ii) the induction of pulmonary inflammation in vivo and (iii) the infiltration in vivo of immune cells into the infected organ. Indeed, infection of a host by this attenuated strain is associated both with an efficient primary immune response (equivalent to that observed with the wild virus) and with a reduced inflammatory response.

Example 10: Secretion of Cytokines/Chemokines, Recruitment of Immune Cells on the Site of the Infection In Vivo and Pulmonary Inflammation in a BALB/c Murine Model Immunised by the Recombinant hMPVs r ΔG-C-85473 and ΔSH-C-85473, Following an Infectious Challenge Following a viral infection, a complex inflammatory and immune response is put in place on the site of the infection thanks to the secretion of cytokines and chemokines by infected epithelial cells (see FIG. 7) and resident immune cells (FIG. 8). Firstly, the effector cells of the innate response (non-specific) are recruited and activated then, secondly, the effector cells of the adaptive response (specific). When the infected individual has been immunised or vaccinated beforehand, the adaptive response is all the more rapid, important and specific the more efficient the memory response. It is the characterisation of this immune response, called secondary, which is described in this example.

BALB/c mice were immunised by intranasal instillation with OptiMem culture medium ("mock" negative control) or $5 \times 10^5$ TCID$^{50}$ of the recombinant viruses rC-85473, ΔSH-C-85473 or ΔG-C-85473.

21 days after immunisation, the mice were infected (infectious challenge) by intranasal instillation of a lethal dose ($1 \times 10^6$ TCID$^{50}$) of the wild virus rC-85473. The immunisation and infectious challenge protocol is shown in FIG. 4A.

1 or 5 days after the infectious challenge (i.e. at days 22 or 26 post-immunisation respectively), 3 mice of each group underwent euthanasia to quantify a selection of cytokines and chemokines secreted in the pulmonary tissue: the results are shown in FIGS. 10A, 10B and 10C. These results demonstrate the induction of a local immune response that differs as a function of the recombinant viruses rC-85473 used for the immunisation of the BALB/c mice:

The groups immunised by the viruses ΔG-C-85473 and ΔSH-C-85473 show a stronger secretion of the pro-inflammatory cytokine IL-6 and the chemokine MCP-1 than the group immunised by the virus WT rC-85473, rapidly 1 day after the infectious challenge.

In addition, the group immunised by the virus ΔSH-C-85473 also shows a significant increase in the secretion of the anti-inflammatory cytokine IL-10 and the chemokines G-CSF and MIP-1β, compared to the group immunised by the virus WT and/or by the virus ΔG-C-85473

After 5 days, all the cytokines/chemokines tested were in sharp decrease compared to the levels measured on day 1 post-challenge, which demonstrates a resorption of the cytokine and inflammatory response induced by the challenge.

These results suggest that immunisation by the attenuated viruses ΔG-C-85473, and more particularly ΔSH-C-85473, leads to the local putting in place of a cytokine response different to that induced by immunisation by the corresponding non-attenuated virus WT.

To evaluate the recruitment of immunity cells on the site of the infection, the amount of main populations of immune cells that infiltrate into the pulmonary tissue to combat against the infection was measured; the results are shown in FIGS. 10D, 10E and 10F.

Thus, the recruitment of T lymphocytes (CD8+ cytotoxic and CD4+ helpers) and B lymphocytes is significantly increased following immunisation with the virus ΔSH-C-85473, compared to the group immunised by the virus WT rC-85473, and compared to the group immunised by the virus ΔG-C-85473 (significant difference uniquely for B lymphocytes, FIG. 10E), 5 days after the infectious challenge.

The populations of recruited macrophages and neutrophils do not show significant differences between the different viruses tested (FIG. 10F).

The group of mice immunised by the virus ΔG-C-85473 shows a cell recruitment profile similar to that of the group immunised by the virus WT, which suggests that the virus ΔG-C-85473 is as efficient for the induction of immune response as a wild virus (WT). Conversely, when the mice were immunised beforehand with the virus ΔSH-C-85473, the adaptive immune response in response to the infectious challenge is more important, while remaining balanced, whereas the innate response does not seem to be affected, which suggests that the virus ΔSH-C-85473 would not induce a more efficient memory immune response.

Finally, 5 days after the challenge, 2 mice per group underwent euthanasia to measure the pulmonary inflammation scores resulting from the challenge of each immunised and "mock" non-immunised group; the results are shown in FIG. 10G.

Figure 4C:
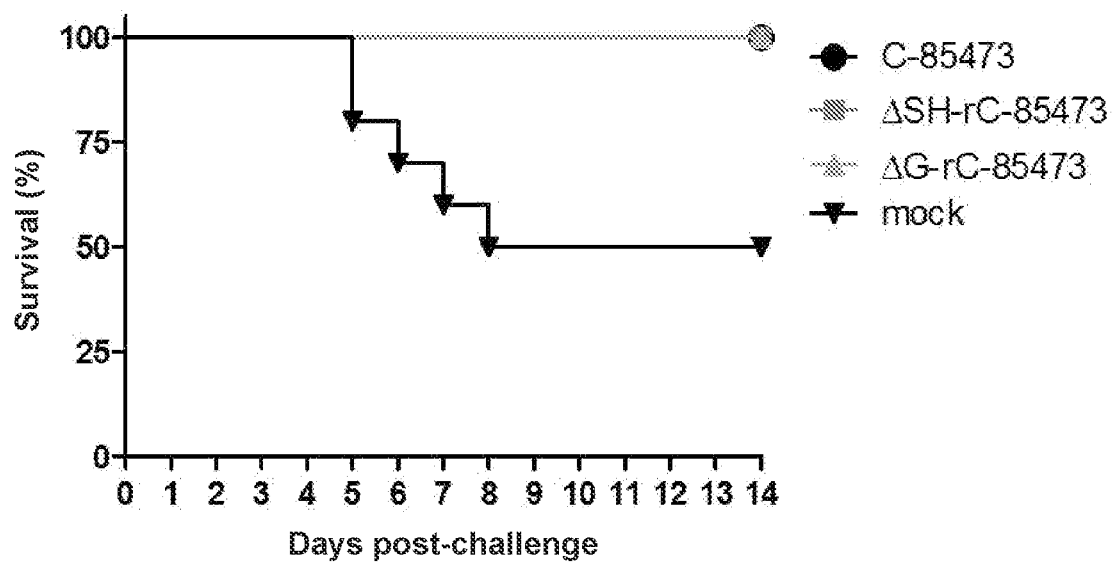
Figure 4D:
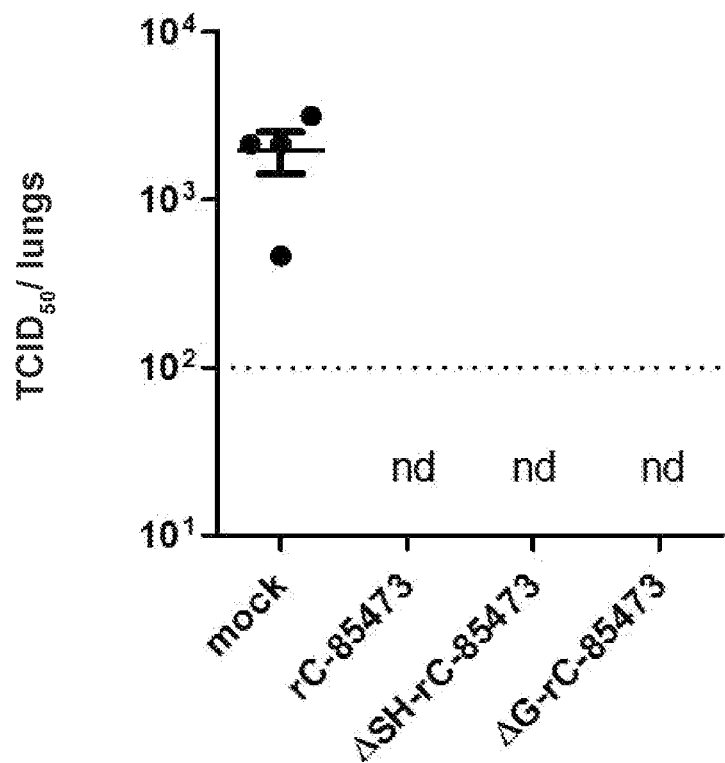
Figure 4E:
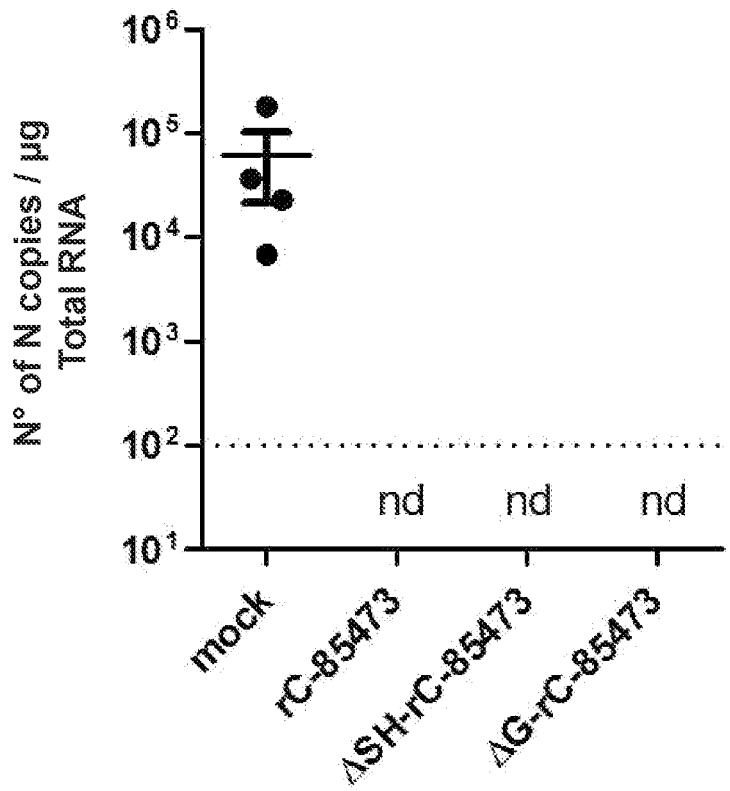

As expected with the use of a lethal inoculum of virus WT rC-85473, which corresponds to 50% mortality of the population [see FIG. 4C], the cumulative inflammation score of the mock-immunised group is very high. As previously, the inflammation scores of the groups immunised by the virus WT rC-85473 or ΔG-C-85473 are very comparable with each other, and slightly decreased compared to the mock-immunised even though the mice of these groups do not demonstrate any mortality [FIG. 4C].

The results of FIG. 10 show that mice immunised by the virus ΔSH-C-85473 put in place a very reduced inflammatory response following the infectious challenge, which suggests that pulmonary attacks would be reduced in this group. Similarly, the pulmonary functionalities would be conserved during infection.

Thus, the attenuated virus ΔSH-C-85473 could enable better pulmonary recruitment of immune cells, in quantity and in quality, in response to a secondary infection, and thus contribute to limiting physiopathology and pulmonary inflammation of the infected host. This more efficient response of the host could also reflect a better memory immune response against the hMPV virus.

In conclusion, this attenuated virus ΔSH-C-85473 has the following characteristics:

(i) it induces greater quantities of pro-inflammatory, anti-inflammatory cytokines and chemokines than the other viruses tested;
(ii) this enabling a more important, but balanced, recruitment of immune cells (CD8+/CD4+T lymphocytes and B lymphocytes) on the site of the infection,
(iii) while generating limited pulmonary inflammation

TABLE 8

Summary of sequences presented in the sequence listing

| | Description |
|---|---|
| SEQ ID NO. 1 | Complete genome sequence of the wild strain of hMPV C-85473 |
| SEQ ID NO. 2 | Complete sequence of the recombinant hMPV ΔSH-rC-85473 |
| SEQ ID NO. 3 | Complete sequence of the recombinant hMPV ΔG-rC-85473 |
| SEQ ID NO. 4 | Complete sequence of the wild recombinant hMPV v rC-85473 coupled to the GFP sequence |
| SEQ ID NO. 5 | Complete sequence of the recombinant hMPV ΔSH-rC-85473 coupled to the GFP sequence |
| SEQ ID NO. 6 | Complete sequence of the recombinant hMPV ΔG-rC-85473 coupled to the GFP sequence |
| SEQ ID NO. 7 | Complete sequence of the wild genome HMPV CAN98-75 |
| SEQ ID NO. 8 | Complete sequence of the wild recombinant hMPV CAN98-75 coupled to the GFP sequence |

REFERENCES

Patents

WO 2005/014626
U.S. Pat. No. 8,841,433

BIBLIOGRAPHIC REFERENCES BY ORDER OF CITATION IN THE TEXT van den Hoogen B G, of Jong J C, Groen J, Kuiken T, of Groot R, Fouchier R A, et al. *A newly discovered human pneumovirus isolated from young children with respiratory tract disease*. Nat Med. 2001; 7(6):719-24

Peret T C, Boivin G, Li Y, Couillard M, Humphrey C, Osterhaus A D, Erdman D D, Anderson L J. *Characterization of human metapneumoviruses isolated from patients in North America*. J Infect Dis. 2002 Jun. 1; 185(11):1660-3.

Mazur N I, Higgins D, Nunes M C, Melero J A, Langedijk A C, Horsley N, Buchholz U J, Openshaw P J, McLellan J S, Englund J A, Mejias A, Karron R A, Simões E A, Knezevic I, Ramilo O, Piedra P A, Chu H Y, Falsey A R, Nair H, Kragten-Tabatabaie L, Greenough A, Baraldi E, Papadopoulos N G, Vekemans J, Polack F P, Powell M, Satav A, Walsh E E, Stein R T, Graham B S, Bont L J; Respiratory Syncytial Virus Network (ReSViNET) Foundation. *The respiratory syncytial virus vaccine landscape: lessons from the graveyard and promising candidates*. Lancet Infect Dis. 2018 Jun. 15. pii: S1473-3099(18) 30292-5.

Herfst S, of Graaf M, Schrauwen E J, Sprong L, Hussain K, van den Hoogen B G, Osterhaus A D, Fouchier R A. *Generation of temperature-sensitive human metapneumovirus strains that provide protective immunity in hamsters*. J Gen Virol. 2008 July; 89(Pt 7):1553-62.

Wei Y, Zhang Y, Cai H, Mirza A M, Iorio R M, Peeples M E, Niewiesk S, Li J. Roles of the putative integrin-binding motif of the human metapneumovirus fusion (f) protein in cell-cell fusion, viral infectivity, and pathogenesis. J Virol. 2014 April; 88(8):4338-52.

Yu C M, Li R P, Chen X, Liu P, Zhao X D. *Replication and pathogenicity of attenuated human metapneumovirus F mutants in severe combined immunodeficiency mice*. Vaccine. 2012 Jan. 5; 30(2):231-6.

Liu P, Shu Z, Qin X, Dou Y, Zhao Y, Zhao X. *A live attenuated human metapneumovirus vaccine strain provides complete protection against homologous viral infection and cross-protection against heterologous viral infection in BALB/c mice*. Clin Vaccine Immunol. 2013 August; 20(8):1246-54.

Zhang Y, Wei Y, Zhang X, Cai H, Niewiesk S, Li J. *Rational design of human metapneumovirus live attenuated vaccine candidates by inhibiting viral mRNA cap methyltransferase*. J Virol. 2014 October; 88(19):11411-29

Biacchesi S, Skiadopoulos M H, Tran K C, Murphy B R, Collins P L, Buchholz U J. *Recovery of human metapneumovirus from cDNA: optimization of growth in vitro and expression of additional genes*. Virology. 2004; 321 (2):247-59

Biacchesi S, Skiadopoulos M H, Yang L, Lamirande E W, Tran K C, Murphy B R, Collins P L, Buchholz U J. *Recombinant human Metapneumovirus lacking the small hydrophobic SH and/or binding G glycoprotein: deletion of G yields a promising vaccine candidate*. Journal of Virology. 2004 December; 78(23):12877-87.

Biacchesi S, Pham Q N, Skiadopoulos M H, Murphy B R, Collins P L, Buchholz U J. *Infection of nonhuman primates with recombinant human metapneumovirus lacking the SH, G, or M2-2 protein categorizes each as a nonessential accessory protein and identifies vaccine candidates*. Journal of virology. 2005; 79(19):12608-13.

Buchholz U J, Biacchesi S, Pham Q N, Tran K C, Yang L, Luongo C L, Skiadopoulos M H, Murphy B R, Collins P L. *Deletion of M2 gene open reading frames 1 and 2 of human metapneumovirus: effects on RNA synthesis, attenuation, and immunogenicity*. J Virol. 2005 June; 79(11):6588-97.

Schickli J H, Kaur J, Macphail M, Guzzetta J M, Spaete R R, Tang R S. *Deletion of human metapneumovirus M2-2 increases mutation frequency and attenuates growth in hamsters*. Virol J. 2008 Jun. 3; 5:69.

Pham Q N, Biacchesi S, Skiadopoulos M H, Murphy B R, Collins P L, Buchholz U J. *Chimeric recombinant human metapneumoviruses with the nucleoprotein or phosphoprotein open reading frame replaced by that of avian metapneumovirus exhibit improved growth in vitro and attenuation in vivo*. J Virol. 2005 December; 79(24): 15114-22.

Tang R S, Schickli J H, MacPhail M, Fernandes F, Bicha L, Spaete J, Fouchier R A, Osterhaus A D, Spaete R, Haller A A. *Effects of human metapneumovirus and respiratory syncytial virus antigen insertion in two 3′ proximal genome positions of bovine/human parainfluenza virus type 3 on virus replication and immunogenicity*. J Virol. 2003 October; 77(20):10819-28.

Tang R S, Mahmood K, Macphail M, Guzzetta J M, Haller A A, Liu H, Kaur J, Lawlor H A, Stillman E A, Schickli J H, Fouchier R A, Osterhaus A D, Spaete R R. *A host-range restricted parainfluenza virus type 3 (PIV3) expressing the human metapneumovirus(hMPV) fusion protein elicits protective immunity in African green monkeys*. Vaccine. 2005 Feb. 25; 23(14):1657-67.

Russell C J, Jones B G, Sealy R E, Surman S L, Mason J N, Hayden R T, Tripp R A, Takimoto T, Hurwitz J L. *A Sendai recombinant virus vaccine expressing a gene for truncated human metapneumovirus (hMPV) fusion protein protects cotton rats from hMPV challenge*. Virology. 2017 September; 509:60-66.

Huck B, Scharf G, Neumann-Haefelin D, Puppe W, Weigl J, Falcone V. *Novel human metapneumovirus sublineage*. Emerg Infect Dis. 2006 January; 12(1):147-50.

Aerts L, Rhéaume C, Carbonneau J, Lavigne S, Couture C, Hamelin M È, Boivin G. *Adjuvant effect of the human metapneumovirus (HMPV) matrix protein in HMPV subunit vaccines*. J Gen Virol. 2015 April; 96(Pt 4):767-74.

Dubois J, Cavanagh M H, Terrier O, Hamelin M E, Lina B, Shi R, et al. *Mutations in the fusion protein heptad repeat domains of human metapneumovirus impact on the formation of syncytia*. The Journal of general virology. 2017; 98(6):1174-80.

Aerts L, Cavanagh M H, Dubois J, Carbonneau J, Rheaume C, Lavigne S, et al. *Effect of in vitro syncytium formation on the severity of human metapneumovirus disease in a murine model*. PloS one. 2015; 10(3):e0120283.

Hamelin M E, Gagnon C, Prince G A, Kiener P, Suzich J, Ulbrandt N, Boivin G. *Prophylactic and therapeutic benefits of a monoclonal antibody against the fusion protein of human metapneumovirus in a mouse model*. Antiviral Res. 2010 October; 88(1):31-7.

Palwithino C E, Cespedes P F, Lay M K, Riedel C A, Kalergis A M, Bueno S M. *Understanding Lung Immunopathology Caused by the Human Metapneumovirus: Implications for Rational Vaccine Design*. Crit Rev Immunol. 2015; 35(3):185-202. Review.

Hamelin M E, Couture C, Sackett M K, Boivin G. *Enhanced lung disease and Th2 response following human metapneumovirus infection in mice immunised with the inactivated virus*. J Gen Virol. 2007 December; 88(Pt 12):3391-400. PubMed PMID: 18024909.

The invention claimed is:

1. An attenuated human metapneumovirus strain comprising one or more genetic modifications of sequence SEQ ID NO. 1 attenuating the virulence of said strain, wherein the genetic modifications of said sequence SEQ ID NO.1 consist of the inactivation of the gene encoding for the SH protein and/or the inactivation of the gene encoding for the G protein.

2. The attenuated human metapneumovirus strain according to claim 1, wherein the genetic modifications of said sequence SEQ ID NO.1 consist of the inactivation of the gene encoding for the SH protein.

3. The attenuated human metapneumovirus strain according to claim 2, wherein said strain comprises sequence SEQ ID NO.2.

4. The attenuated human metapneumovirus strain according to claim 1, wherein the genetic modifications of said sequence SEQ ID NO.1 consist of the inactivation of the gene encoding for the G protein.

5. The attenuated human metapneumovirus strain according to claim 4, wherein said strain comprises sequence SEQ ID NO.3.

6. The attenuated human metapneumovirus strain according to claim 1, wherein the genetic modifications of sequence SEQ ID NO.1 consist of the inactivation of both genes encoding for the G protein and the SH protein.

7. The attenuated human metapneumovirus strain according to claim 1, wherein the sequence of the strain further comprises at least one exogenous gene.

8. A method for expressing at least one exogenous gene in target cells of human metapneumovirus, comprising the introduction of an attenuated human metapneumovirus strain according to claim 7 into said target cells.

9. A method for preventing and/or treating infections by viruses of the Pneumoviridae family, comprising the administration to individuals susceptible to be infected or infected by such viruses, of at least one attenuated human metapneumovirus strain according to claim 1.

10. The method according to claim 9, wherein said viruses of the Pneumoviridae family are human metapneumoviruses.

* * * * *

UNITED STATES PATENT AND TRADEMARK OFFICE
CERTIFICATE OF CORRECTION

| | | |
|---|---|---|
| PATENT NO. | : 11,504,424 B2 | Page 1 of 1 |
| APPLICATION NO. | : 17/262263 | |
| DATED | : November 22, 2022 | |
| INVENTOR(S) | : Rosa-Calatrava et al. | |

It is certified that error appears in the above-identified patent and that said Letters Patent is hereby corrected as shown below:

On the Title Page

Under abstract "10 Claims, 19 Drawing Sheets" should read --16 Claims, 19 Drawing Sheets--.

In the Claims

In Column 126, Line 21, after Claim 10, please insert the following:

--11. The method according to claim 9, wherein said viruses of the Pneumoviridae family are orthopneumoviruses.

12. A method for preventing and/or treating infections by viruses of the Pneumoviridae family, comprising the administration to individuals susceptible to be infected or infected by such viruses of an attenuated human metapneumovirus strain according to claim 7,
wherein said attenuated human metapneumovirus strain expresses at least one viral antigen of said viruses.

13. A vaccine composition comprising, in a pharmaceutically acceptable vehicle, at least one attenuated human metapneumovirus strain according to claim 1, and optionally an adjuvant.

14. The vaccine composition according to claim 13, wherein it is in a pharmaceutical form intended for administration by inhalation.

15. The attenuated human metapneumovirus strain according to claim 7, wherein the at least one exogenous gene codes for a viral antigen.

16. The method according to claim 11, wherein said orthopneumovirus is the human syncytial respiratory virus.--.

Signed and Sealed this
Fourth Day of April, 2023

*Katherine Kelly Vidal*

Katherine Kelly Vidal
*Director of the United States Patent and Trademark Office*